US012797614B2

(12) United States Patent
Gill et al.

(10) Patent No.: US 12,797,614 B2
(45) Date of Patent: Nov. 17, 2026

(54) SYSTEMS AND METHODS FOR STIMULATING TWO OR MORE NERVE BRANCHES

(71) Applicant: Texas Medical Center, Houston, TX (US)

(72) Inventors: Kirt Gill, Houston, TX (US); Laura Ortiz-Velez, Pearland, TX (US); Joseph Upchurch, Houston, TX (US)

(73) Assignee: Texas Medical Center, Houston, TX (US)

( * ) Notice: Subject to any disclaimer, the term of this patent is extended or adjusted under 35 U.S.C. 154(b) by 220 days.

(21) Appl. No.: 18/486,840

(22) Filed: Oct. 13, 2023

(65) Prior Publication Data

US 2024/0042203 A1 Feb. 8, 2024

Related U.S. Application Data

(63) Continuation of application No. PCT/US2022/024988, filed on Apr. 15, 2022.

(Continued)

(51) Int. Cl.

*A61N 1/36* (2006.01)
*A61B 5/026* (2006.01)
*A61N 1/04* (2006.01)

(52) U.S. Cl.

CPC .......... *A61N 1/36025* (2013.01); *A61B 5/026* (2013.01); *A61N 1/0456* (2013.01); *A61N 1/0484* (2013.01); *A61N 1/36034* (2017.08)

(58) Field of Classification Search

None

See application file for complete search history.

(56) References Cited

U.S. PATENT DOCUMENTS 7,149,574 B2 12/2006 Yun et al.
7,636,597 B2 12/2009 Gross et al.

(Continued)

FOREIGN PATENT DOCUMENTS

CA 3137936 A1 10/2020
CN 102858404 B 8/2015

(Continued)

OTHER PUBLICATIONS

PCT/US2023/071740 International Search Report and Written Opinion mailed Jan. 19, 2024.

(Continued)

*Primary Examiner* — Michael W Kahelin
(74) *Attorney, Agent, or Firm* — Resonance IP Law, PC

(57) ABSTRACT

Disclosed herein are devices, systems, and methods for treating a medical condition through a coordinated stimulation of two or more target nerves. In some embodiments, the stimulation comprises electrical stimulation delivered to a patient. In some embodiments, the coordinated stimulation comprises the two or more target nerves being stimulated in parallel, in series, a combination thereof, or any coordinated temporal sequence. In some embodiments, the stimulation delivery is contingent on an electrode placement confirmation via one or more electrode monitors. In some embodiments, the delivered electrical stimulation comprises one or more stimulation parameters configured to be adjusted based on feedback from the patient. In some embodiments, the one or more stimulation parameters are automatically randomized over a normal distribution.

25 Claims, 17 Drawing Sheets

Related U.S. Application Data

(60) Provisional application No. 63/242,785, filed on Sep. 10, 2021, provisional application No. 63/176,099, filed on Apr. 16, 2021.

(56) References Cited

U.S. PATENT DOCUMENTS

| | | | | |
|---|---|---|---|---|
| 7,983,762 | B2 | 7/2011 | Gliner et al. | |
| 8,055,347 | B2 | 11/2011 | Lamensdorf et al. | |
| 8,190,248 | B2 | 5/2012 | Besio et al. | |
| 8,406,869 | B2 | 3/2013 | Lamensdorf et al. | |
| 8,606,361 | B2 | 12/2013 | Gliner et al. | |
| 8,676,330 | B2 | 3/2014 | Simon et al. | |
| 8,688,220 | B2 | 4/2014 | DeGiorgio et al. | |
| 8,702,584 | B2 | 4/2014 | Rigaux et al. | |
| 8,755,892 | B2 | 6/2014 | Amurthur et al. | |
| 8,843,210 | B2 | 9/2014 | Simon et al. | |
| 8,914,114 | B2 | 12/2014 | Tracey et al. | |
| 8,918,178 | B2 | 12/2014 | Simon et al. | |
| 8,958,881 | B2 | 2/2015 | Lamensdorf et al. | |
| 9,014,823 | B2 | 4/2015 | Simon et al. | |
| 9,020,598 | B2 | 4/2015 | Simon et al. | |
| 9,043,001 | B2 | 5/2015 | Simon et al. | |
| 9,089,691 | B2 | 7/2015 | Libbus et al. | |
| 9,119,953 | B2 | 9/2015 | Simon et al. | |
| 9,174,066 | B2 | 11/2015 | Simon et al. | |
| 9,186,510 | B2 | 11/2015 | Gliner et al. | |
| 9,233,245 | B2 | 1/2016 | Lamensdorf et al. | |
| 9,233,246 | B2 | 1/2016 | Simon et al. | |
| 9,272,157 | B2 | 3/2016 | Borsody | |
| 9,333,347 | B2 | 5/2016 | Simon et al. | |
| 9,358,381 | B2 | 6/2016 | Simon et al. | |
| 9,399,134 | B2 | 7/2016 | Simon et al. | |
| 9,468,763 | B2 | 10/2016 | Simon et al. | |
| 9,662,269 | B2 | 5/2017 | Brown et al. | |
| 9,782,584 | B2 | 10/2017 | Cartledge et al. | |
| 9,808,627 | B2 | 11/2017 | Gliner et al. | |
| 9,839,577 | B2 | 12/2017 | Brown et al. | |
| 10,010,479 | B2 | 7/2018 | Brown et al. | |
| 10,039,928 | B2 | 8/2018 | Hyde et al. | |
| 10,058,704 | B2 | 8/2018 | Degiorgio et al. | |
| 10,105,549 | B2 | 10/2018 | Borsody | |
| 10,130,809 | B2 | 11/2018 | Cartledge et al. | |
| 10,279,178 | B2 | 5/2019 | Cartledge et al. | |
| 10,286,211 | B2 | 5/2019 | Simon et al. | |
| 10,293,158 | B2 | 5/2019 | Goodall et al. | |
| 10,322,062 | B2 | 6/2019 | Brown et al. | |
| 10,363,415 | B2 | 7/2019 | Simon et al. | |
| 10,384,059 | B2 | 8/2019 | Simon et al. | |
| 10,384,061 | B2 | 8/2019 | Simon et al. | |
| 10,441,780 | B2 | 10/2019 | Simon et al. | |
| 10,507,325 | B2 | 12/2019 | Simon et al. | |
| 10,537,728 | B2 | 1/2020 | Simon et al. | |
| 10,537,729 | B2 | 1/2020 | Cook et al. | |
| 10,576,279 | B2 | 3/2020 | Muller et al. | |
| 10,688,274 | B1 * | 6/2020 | Jovanov | A61M 21/02 |
| 10,695,568 | B1 | 6/2020 | Covalin | |
| 10,773,080 | B2 | 9/2020 | Rigaux | |
| 10,828,461 | B2 | 11/2020 | Cartledge et al. | |
| 11,260,229 | B2 | 3/2022 | Manogue | |
| 11,351,370 | B2 | 6/2022 | Covalin et al. | |
| 2007/0049814 | A1 | 3/2007 | Muccio | |
| 2014/0135886 | A1 | 5/2014 | Cook et al. | |
| 2015/0142082 | A1 | 5/2015 | Simon et al. | |
| 2017/0028198 | A1 | 2/2017 | Degiorgio et al. | |
| 2017/0151433 | A1 | 6/2017 | Simon et al. | |
| 2017/0340260 | A1 * | 11/2017 | Chowdhury | A61B 5/4064 |
| 2017/0368329 | A1 | 12/2017 | Tyler et al. | |
| 2018/0064935 | A1 | 3/2018 | Leonhardt et al. | |
| 2018/0200522 | A1 | 7/2018 | Taca, Jr. | |
| 2018/0359332 | A9 | 12/2018 | Gliner et al. | |
| 2019/0022389 | A1 | 1/2019 | Leonhardt | |
| 2019/0046794 | A1 | 2/2019 | Goodall et al. | |
| 2019/0111255 | A1 | 4/2019 | Errico et al. | |
| 2019/0134393 | A1 | 5/2019 | Wong et al. | |
| 2019/0151604 | A1 | 5/2019 | Harper et al. | |
| 2019/0201684 | A1 * | 7/2019 | Williams | A61N 1/36132 |
| 2019/0201694 | A1 | 7/2019 | Hsu et al. | |
| 2019/0223747 | A1 | 7/2019 | Chou | |
| 2019/0262229 | A1 | 8/2019 | Brown et al. | |
| 2019/0275322 | A1 | 9/2019 | Cartledge et al. | |
| 2019/0351230 | A1 | 11/2019 | Cartledge et al. | |
| 2019/0374771 | A1 | 12/2019 | Simon et al. | |
| 2020/0001083 | A1 | 1/2020 | Simon et al. | |
| 2020/0038653 | A1 * | 2/2020 | Sitaram | A61B 5/055 |
| 2020/0046976 | A1 | 2/2020 | Simon et al. | |
| 2020/0078589 | A1 | 3/2020 | Simon et al. | |
| 2020/0086108 | A1 | 3/2020 | Simon et al. | |
| 2020/0094040 | A1 | 3/2020 | Ganzer | |
| 2020/0094055 | A1 | 3/2020 | Manogue | |
| 2020/0179689 | A1 | 6/2020 | Rigaux | |
| 2020/0197707 | A1 | 6/2020 | Covalin | |
| 2020/0222695 | A1 | 7/2020 | Simon et al. | |
| 2020/0246615 | A1 | 8/2020 | Simon et al. | |
| 2020/0246617 | A1 | 8/2020 | Errico et al. | |
| 2020/0261722 | A1 | 8/2020 | Alataris et al. | |
| 2020/0269046 | A1 | 8/2020 | Page et al. | |
| 2020/0298001 | A1 | 9/2020 | Muller et al. | |
| 2020/0353240 | A1 | 11/2020 | Simon et al. | |
| 2020/0368527 | A1 | 11/2020 | Asirvatham | |
| 2020/0368541 | A1 | 11/2020 | Perryman et al. | |
| 2020/0398043 | A1 | 12/2020 | Simon et al. | |
| 2021/0031026 | A1 | 2/2021 | Simon et al. | |
| 2021/0113834 | A1 | 4/2021 | Wong et al. | |
| 2021/0154474 | A1 * | 5/2021 | Narayan | A61N 1/0504 |
| 2021/0322718 | A1 * | 10/2021 | DiLorenzo | A61N 1/36025 |
| 2021/0346711 | A1 | 11/2021 | Ansari et al. | |
| 2022/0088374 | A1 * | 3/2022 | Ackermann | A61N 1/36064 |
| 2022/0233860 | A1 * | 7/2022 | Hamner | A61N 1/36031 |
| 2022/0339443 | A1 * | 10/2022 | Schobben | A61N 1/36017 |
| 2025/0381397 | A1 | 12/2025 | Gill et al. | |

FOREIGN PATENT DOCUMENTS

| | | | |
|---|---|---|---|
| DE | 102015002589 | B4 | 4/2017 |
| EP | 1843814 | B1 | 5/2008 |
| EP | 2026872 | B1 | 9/2009 |
| EP | 3277369 | B1 | 12/2019 |
| EP | 3693053 | A1 | 8/2020 |
| JP | 5858920 | B2 | 2/2016 |
| JP | 6606270 | B2 | 11/2019 |
| WO | WO-2016155773 | A1 | 10/2016 |
| WO | WO-2020079218 | A1 | 4/2020 |
| WO | WO-2020185601 | A1 | 9/2020 |
| WO | WO-2020219072 | A1 | 10/2020 |
| WO | 2021011165 | A1 | 1/2021 |
| WO | WO-2022221644 | A2 | 10/2022 |
| WO | 2024031086 | A1 | 2/2024 |

OTHER PUBLICATIONS

PCT/US2022/024988 International Search Report and Written Opinion mailed Nov. 7, 2022.

Adair, Devin et al. Electrical stimulation of cranial nerves in cognition and disease. Brain stimulation 13(3):717-750 (2020).

EP22788999.5 Extended European Search Report dated Jan. 31, 2025.

PCT/US2022/024988 Invitation to Pay Additional Fees dated Sep. 9, 2022.

PCT/US2023/071740 Invitation to Pay Additional Fees dated Nov. 29, 2023.

* cited by examiner

SYSTEMS AND METHODS FOR STIMULATING TWO OR MORE NERVE BRANCHES

CROSS-REFERENCE

This application is a continuation of International Application No. PCT/US2022/024988, filed Apr. 15, 2022, which claims priority to U.S. Provisional Application No. 63/242,785, filed Sep. 10, 2021, and U.S. Provisional Application No. 63/176,099, filed Apr. 16, 2021, the contents of which are incorporated herein by reference.

BACKGROUND

Nerve stimulation is known in the art to provide certain physiological effects on a patient. Different types of nerve stimulation include electrical nerve stimulation, chemical nerve stimulation, thermal nerve stimulation, and mechanical nerve stimulation. Electrical stimulation can be delivered as transcutaneously or percutaneously. Nerve stimulation is commonly used to alleviate pain experienced by a patient.

Cardiovascular disease is a leading cause of death globally and is responsible for about 25% of deaths in the United States. One in every 6 cardiovascular disease deaths is due to stroke, and more than 795,000 people in the United States have a stroke annually. About 87% of all strokes are ischemic strokes, in which blood flow to the brain is blocked. Stroke is a leading cause of serious long-term disability, as stroke reduces mobility in more than half of stroke survivors age 65 and over due to brain damage resulting from the stroke. Stroke-related costs in the United States came to nearly $46 billion between 2014 and 2015. Presently, there are few commercially available treatments available to treat or mitigate an ischemic stroke prior to administration of a reperfusion therapy.

The following references may be of relevance: WO2020079218A1, WO2020185601A1, WO2020219072A1, U.S. Pat. Nos. 7,149,574B2, 7,636,597B2, 7,983,762B2, 8,055,347B2, 8,190,248B2, 8,676,330B2, 8,702,584B2, 8,755,892B2, 8,843,210B2, 8,914,114B2, 8,918,178B2, 8,958,881B2, 9,089,691B2, 9,119,953B2, 9,174,066B2, 9,233,245B2, 9,272,157B2, 9,333,347B2, 9,358,381B2, 9,399,134B2, 9,468,763B2, 9,782,584B2, 10,058,704B2, 10,105,549B2, 10,130,809B2, 10,286,211B2, 10,293,158B2, 10,039,928B2, 10,441,780B2, 10,537,728B2, 10,537,729B2, 10,576,279B2, 10,695,568B1, 10,773,080B2, US20150142082A1, US20170028198A1, US20170151433A1, US20180064935A1, US20180200522A1, US20190022389A1, US20190046794A1, US20190111255A1, US20190134393A1, US20190151604A1, US20190201694A1, US20190262229A1, US20200046976A1, US20200086108A1, US20200094040A1, US20200094055A1, US20200261722A1, US20200269046A1, US20200298001A1, US20200368527A1, US20210154474A1, JP5858920B2, EP1843814B1, EP2026872B1, EP3693053A1, DE102015002589B4, and CN102858404B.

SUMMARY

The lack of commercially available treatments available to treat or mitigate an ischemic stroke prior to administration of a reperfusion therapy increases the severity of an ischemic stroke due to prolonged lack of oxygen to the region of the ischemic stroke, and the resulting brain damage. A non-invasive therapy which could increase the flow of blood or oxygen to the brain and which could be administered shortly following diagnosis and before a reperfusion therapy is administered would serve to significantly improve the treatment of ischemic stroke, improve patient outcomes, and reduce stroke-related costs. For instance, prolonged lack of oxygen to the penumbral tissue region of an ischemic stroke results in increased infarct core formation, increased brain damage. These are common negative patient outcomes because of the prolonged time between stroke diagnosis and administration of a reperfusion therapy. Similarly, the rapid reoxygenation of the penumbral tissue following administration of a reperfusion therapy may also result in a reperfusion injury, contributing to negative patient outcomes and high stroke-related costs.

It is appreciated by the inventors that nerve stimulation may be used to increase a flow of blood and oxygen to the brain, and such an application may be useful in treating an ischemic stroke, and that nerve stimulation may be applied quickly following diagnosis of stroke well before a reperfusion therapy can be administered. It is similarly appreciated by the inventors that nerve stimulation may be used to decrease a flow of blood and oxygen to the brain, and such an application may be useful in treating, mitigating, or preventing a reperfusion injury resulting from a reperfusion therapy administered in conjunction with the treatment for an ischemic stroke. Disclosed herein are methods and systems for stimulation of the trigeminal nerve and vagal nerve which may be used for increasing or decreasing a flow of blood to the brain, treating an ischemic stroke and/or a reperfusion injury, which may serve to improve stroke-related patient outcomes, and reduce high stroke-related costs.

Aspects disclosed herein provide a method of stimulating a plurality of target nerves in a subject to treat a medical condition, the method comprising: transcutaneously delivering a first stimulation energy to a supraorbital branch of a trigeminal nerve; transcutaneously delivering a second stimulation energy to an auricular branch of a vagal nerve, wherein the first and second stimulation energies are delivered in combination to treat the medical condition. In some embodiments, the medical condition is one or more of ischemic stroke, cerebral brain damage due to ischemic stroke, hemorrhagic stroke, cerebral brain damage due to hemorrhagic stroke, a reperfusion injury, traumatic brain injury, subarachnoid hemorrhage, a hematoma, a hemorrhage, a subarachnoid hemorrhage, inflammation, hypertension, or hypotension. In some embodiments, one or more of the first or second stimulation energies are delivered by one or more of a wearable or adherable stimulation device. In some embodiments, one or more of the first or second stimulation energies are electrical. In some embodiments, one or more of the first or second stimulation energies are one or more of electrical, mechanical, vibratory, acoustic, optical, or thermal. In some embodiments, one or more of the first or second stimulation energies are provided at a frequency between 0.2 and 500 Hz. In some embodiments, one or more of the first or second stimulation energies are provided at an amplitude of between 0.1 and 200 mA. In some embodiments, wherein one or more of the first or second stimulation energies are provided at a pulse width between 1 us and 2 s. In some embodiments, one or more of the first or second stimulation energies provide a charge of between 0.5 mC to 200 mC. In some embodiments, one or more of the first or second stimulation energies are biphasic. In some embodiments, one or more of the first or second stimulation energies are delivered with one or more randomized stimulation parameters, the one or more stimulation parameters comprising one or more of pulse width; frequency; amplitude; pulse train duration; a delay between pulse trains; interphase duration; time between biphasic pulses; ratio of a recovery pulse to a depolarization pulse; an amount of time between altering a parameter; or a relative. In some embodiments, the first and second stimulation energies are delivered within 24 hours of an insult to the subject, or within 3-5 days of the insult to the subject. In some embodiments, the insult is a stroke. In some embodiments, the first and second stimulation energies are delivered at a first ratio of first to second stimulation energy for a first time period, wherein the first and second stimulation energies are delivered at a second ratio of first to second stimulation energy for a second time period, wherein the first and second ratios are different, and wherein the second time period is after the first time period. In some embodiments, further comprising determining whether reperfusion has occurred in the subject. In some embodiments, changing a rate of delivering one or more of the first or second stimulation energies in response to an occurrence of reperfusion in the subject. In some embodiments, the method includes transcutaneously delivering a first stimulation energy to a supraorbital branch of a trigeminal nerve comprises delivering the stimulation energy to the supratrochlear branch of the trigeminal nerve. In some embodiments, the method includes delivering a first stimulation energy to a supratrochlear branch of the trigeminal nerve. In some embodiments, the method includes transcutaneously delivering a second stimulation energy to an auricular branch of a vagal nerve comprises delivering the stimulation energy to the auriculotemporal branch of the trigeminal nerve. In some embodiments, the method includes delivering a first stimulation energy an auricular branch of a vagal nerve.

Aspects disclosed herein provide a device for stimulating a plurality of target nerves in a subject to treat a medical condition, the device comprising: a housing configured to be one or more of worn by or adhered to the subject; a first stimulation element coupled to the housing and configured to be positioned over skin of the subject adjacent a supraorbital branch of the trigeminal nerve when the housing is worn by or adhered to the subject; a second stimulation element coupled to the housing and configured to be positioned over skin of the subject adjacent an auricular branch of the vagal nerve when the housing is worn by or adhered to the subject; and a controller coupled to the first and second stimulation elements and configured to cause the first and second stimulation elements to in combination deliver a first stimulation energy to the branch of the trigeminal nerve and a second stimulation energy to the branch of the vagal nerve. In some embodiments, the first or second stimulation energies are delivered simultaneously, or sequentially. In some embodiments, the housing comprises one or more of a helmet, head strap, band, or belt. In some embodiments, the housing comprises an ear clip. In some embodiments, the first stimulation element comprises a first plurality of stimulation electrodes. In some embodiments, the second stimulation element comprises a second plurality of stimulation electrodes. In some embodiments, one or more of the first or second stimulation elements are configured to provide one or more of electrical, mechanical, vibratory, acoustic, optical, or thermal stimulation. In some embodiments, the controller is configured to provide one or more of the first or second electrical stimulation energies with a frequency between 0.2 and 500 Hz. In some embodiments, the controller is configured to provide one or more of the first or second electrical stimulation energies with an amplitude of between 0.1 and 200 mA. In some embodiments, the controller is configured to provide one or more of the first or second stimulation energies with a pulse width between 1 us and 2 s. In some embodiments, one or more of the first or second stimulation energies provide a charge of between 0.5 mC to 200 mC. In some embodiments, the controller is configured to provide one or more of the first or second stimulation energies as a biphasic stimulation signal. In some embodiments, the controller is configured to provide one or more of the first or second stimulation energies with one or more randomized stimulation parameters, the one or more stimulation parameters comprising one or more of pulse width; frequency; amplitude; pulse train duration; a delay between pulse trains; interphase duration; time between biphasic pulses; ratio of a recovery pulse to a depolarization pulse; an amount of time between altering a parameter; or a relative. In some embodiments, the controller is configured to provide the first and second stimulation energies at a first ratio of first to second stimulation energy for a first time period and the first and second stimulation energies at a second ratio of first to second stimulation energy for a second time period, wherein the first and second ratios are different, and wherein the second time period is after the first time period.

Aspects disclosed herein provide a method of stimulating a plurality of target nerves in a subject to slow progression of brain damage due to ischemic stroke, the method comprising: transcutaneously delivering a first stimulation energy to a branch of a trigeminal nerve; transcutaneously delivering a second stimulation energy to a branch of a vagal nerve, wherein the first and second stimulation energies are delivered in combination to slow progression of brain damage due to ischemic stroke. In some embodiments, the branch of the trigeminal nerve comprises a supraorbital branch of the trigeminal nerve. In some embodiments, the branch of the vagal nerve comprises a auricular branch of the vagal nerve. In some embodiments, one or more of the first or second stimulation energies are delivered by one or more of a wearable or adherable stimulation device. In some embodiments, one or more of the first or second stimulation energies are electrical. In some embodiments, one or more of the first or second stimulation energies are one or more of electrical, mechanical, vibratory, acoustic, optical, or thermal. In some embodiments, one or more of the first or second stimulation energies are provided at a frequency between 0.2 and 500 Hz. In some embodiments, one or more of the first or second stimulation energies are provided at an amplitude of between 0.1 and 200 mA. In some embodiments, one or more of the first or second stimulation energies are provided at a pulse width between 1 us and 2 s. In some embodiments, one or more of the first or second stimulation energies provide a charge of between 0.5 mC to 200 mC. In some embodiments, one or more of the first or second stimulation energies are biphasic. In some embodiments, one or more of the first or second stimulation energies are delivered with one or more randomized stimulation parameters, the one or more stimulation parameters comprising one or more of pulse width; frequency; amplitude; pulse train duration; a delay between pulse trains; interphase duration; time between biphasic pulses; ratio of a recovery pulse to a depolarization pulse; an amount of time between altering a parameter; or a relative. In some embodiments, the first and second electrical stimulation energies are delivered within 24 hours of an insult to the subject, or within 3-5 days of the insult to the subject. In some embodiments, the insult is a stroke. In some embodiments, the first and second stimulation energies are delivered at a first ratio of first to second stimulation energy for a first time period, wherein the first and second stimulation energies are delivered at a second ratio of first to second stimulation energy for a second time period, wherein the first and second ratios are different, and wherein the second time period is after the first time period. In some embodiments, determining whether reperfusion has occurred in the subject. In some embodiments, changing a rate of delivering one or more of the first or second stimulation energies in response to an occurrence of reperfusion in the subject.

Aspects disclosed herein provide a device for stimulating a plurality of target nerves in a subject to slow progression of brain damage due to ischemic stroke, the device comprising: a housing configured to be one or more of worn by or adhered to the subject; a first stimulation element coupled to the housing and configured to be positioned over skin of the subject adjacent a branch of the trigeminal nerve when the housing is worn by or adhered to the subject; a second stimulation element coupled to the housing and configured to be positioned over skin of the subject adjacent a branch of the vagal nerve when the housing is worn by or adhered to the subject; and a controller coupled to the first and second stimulation elements and configured to cause the first and second stimulation elements to in combination deliver a first stimulation energy to the branch of the trigeminal nerve and a second stimulation energy to the branch of the vagal nerve. In some embodiments, the first or second stimulation energies are delivered simultaneously, or sequentially. In some embodiments, the housing comprises one or more of a helmet, head strap, band, or belt. In some embodiments, the housing is configured to position the first stimulation element adjacent a supraorbital branch of the trigeminal nerve. In some embodiments, the housing comprises an ear clip. In some embodiments, the housing is configured to position the second stimulation element adjacent an auricular branch of the vagal nerve. In some embodiments, the first stimulation element comprises a first plurality of stimulation electrodes. In some embodiments, the second stimulation element comprises a second plurality of stimulation electrodes. In some embodiments, one or more of the first or second stimulation elements are configured to provide one or more of electrical, mechanical, vibratory, acoustic, optical, or thermal stimulation. In some embodiments, the controller is configured to provide one or more of the first or second stimulation energies with a frequency between 0.2 and 500 Hz. In some embodiments, the controller is configured to provide one or more of the first or second stimulation energies with an amplitude of between 0.1 and 200 mA. In some embodiments, the controller is configured to provide one or more of the first or second stimulation energies with a pulse width between 1 us and 2 s. In some embodiments, one or more of the first or second stimulation energies provide a charge of between 0.5 mC to 200 mC. In some embodiments, the controller is configured to provide one or more of the first or second stimulation energies as a biphasic stimulation signal. In some embodiments, the controller is configured to provide one or more of the first or second stimulation energies with one or more randomized stimulation parameters, the one or more stimulation parameters comprising one or more of pulse width; frequency; amplitude; pulse train duration; a delay between pulse trains; interphase duration; time between biphasic pulses; ratio of a recovery pulse to a depolarization pulse; an amount of time between altering a parameter; or a relative. In some embodiments, the controller is configured to provide the first and second stimulation energies at a first ratio of first to second stimulation energy for a first time period and the first and second stimulation energies at a second ratio of first to second stimulation energy for a second time period, wherein the first and second ratios are different, and wherein the second time period is after the first time period.

Aspects disclosed herein provide a method of stimulating a plurality of target nerves in a subject to treat a medical condition, the method comprising: transcutaneously delivering a first stimulation energy to a supraorbital branch of a trigeminal nerve; transcutaneously delivering a second stimulation energy to an auricular branch of a vagal nerve, wherein the first and second stimulation energies are delivered simultaneously to treat the medical condition.

Aspects disclosed herein provide a method of stimulating a plurality of target nerves in a subject to treat a medical condition, the method comprising: transcutaneously delivering a first stimulation energy to a supraorbital branch of a trigeminal nerve; transcutaneously delivering a second stimulation energy to an auricular branch of a vagal nerve, wherein the first and second stimulation energies are delivered sequentially to treat the medical condition.

In some embodiments, the stimulation energy may be provided at a variety of amounts of charge per unit pulse, for example, between 0.5 mC to 200 mC or any range in between, including, but not limited to a sub-range of 1, 2, 3, 4, 5, 10, 20, 30, 40, 50, 75, 100, 150, 200 mC, to name a few, anywhere in between the 0.5 mC to 200 mC. In some embodiments, stimulation energy may be provided at a variety of pulse widths and pulse width ranges, for example, between 1 us to 2 s or any range in between, including, but not limited to a sub-range of 1 us, 2 us, 3 us, 4 us, 5 us, 10 us, 20, us, 30 us, 40 us, 50 us, 75 us, 100 us, 150 us, 200 us, 250 us, 300 us, 350 us, 400 us, 450 us, 500 us, 600 us, 700 us, 800 us, 900 us, 1 ms, 2 ms, 2 ms, 3 ms, 4 ms, 5 ms, 10 ms, 25 ms, 50 ms, 100 ms, 150 ms, 200 ms, 250 ms, 300 ms, 350 ms, 400 ms, 450 ms, 500 ms, 600 ms, 700 ms, 800 ms, 900 ms, is, 1.1 s, 1.2 s, 1.3 s, 1.4 s, 1.5 s, 1.6 s, 1.7 s, 1.8 s, 1.9 s, to name a few, anywhere in between the 1 us-2 s range, for example 100 to 1000 us. In some embodiments, stimulation energy may be provided at a variety of amplitudes and amplitude ranges, for example, between 0.1-200 mA or any range in between, including, but not limited to a sub-range of 1, 2, 3, 4, 5, 10, 20, 30, 40, 50, 75, 100, 150 mA, to name a few, anywhere in between the 0.1-200 mA range, for example 1 to 10 mA. In some embodiments, stimulation energy may be provided at a variety of frequencies and frequency ranges, for example, between 0.2-500 Hz or any range in between, including, but not limited to a sub-range of 1, 2, 3, 4, 5, 10, 20, 30, 40, 50, 75, 100, 150, 200, 250, 300, 350, 400, 450 Hz, to name a few, anywhere in between the 0.2-500 Hz range, for example 10 to 100 Hz.

Disclosed herein, in one aspect, is a device assembly for neural stimulation of a plurality of target nerves in a patient, the device comprising: a) a power source; b) a first neural stimulator configured to deliver a first stimulation to a first target nerve of the plurality of target nerves, the first neural stimulator in operative communication with the power source; c) a second neural stimulator configured to deliver a second stimulation to a second target nerve of the plurality of target nerve, the second neural stimulator in operative communication with the power source, wherein the first target nerve is different from the second target nerve; d) a controller in operative communication with the power source, the first neural stimulator, and the second neural stimulator, wherein the controller is configured to deliver one or both of the first stimulation and the second stimulation, wherein delivery of the first stimulation is based on a first set of stimulation parameters and delivery of the second stimulation is based on a second set of stimulation parameters, wherein the controller is configured to deliver the first stimulation and second stimulation according to a pre-determined temporal sequence; and e) one or more structures configured to hold the power source, first neural stimulator, and the second neural stimulator, wherein the first neural stimulator is spaced apart from the second neural stimulator.

In some embodiments, one of the first target nerve and the second target nerve comprises a vagus nerve, a trigeminal nerve, a facial nerve, an auditory nerve, an auricular nerve, or neural ganglion (ganglia) or nucleus (nuclei), a sympathetic nerve, a parasympathetic nerve, a sensory nerve, or a combination thereof. In some embodiments, the vagus nerve comprises an auricular branch, a pharyngeal nerve, a superior laryngeal nerve, superior cervical cardiac branches of the vagus nerve, or a combination thereof. In some embodiments, the trigeminal nerve comprises an auriculotemporal branch, a supratrochlear branch, a supraorbital branch, a maxillary branch, an ophthalmic branch, an infraorbital branch, or a combination thereof. In some embodiments, the neural ganglion (ganglia) or nucleus (nuclei)comprises sphenopalatine ganglion, *geniculate* ganglion, otic ganglion, ciliary ganglion, nucleus ambiguous, spinal trigeminal nucleus, solitary nucleus, trigeminal ganglion, or a combination thereof.

In some embodiments, one or both of the first neural stimulator and second neural stimulator comprises an electrode. In some embodiments, each electrode is configured to be in contact with a patient skin, such that the delivery of one or both of the first stimulation and second stimulation is transcutaneous. In some embodiments, each electrode is configured to be disposed beneath a patient skin, such that the delivery of one or both of the first stimulation and second stimulation is percutaneous.

In some embodiments, the device assembly further comprises a feedback device in operative communication with the controller, wherein the feedback device is disposed with the one or more structures, wherein the feedback device provides an activation interlock for one or both of the first neural stimulator and the second neural stimulator. In some embodiments, the feedback device comprises an electrode monitor. In some embodiments, the feedback device comprises a first electrode monitor corresponding to the first neural stimulator, and a second electrode monitor corresponding to the second neural stimulator. In some embodiments, the first electrode monitor is integrated with the first neural stimulator and/or the second electrode monitor is integrated with the second neural stimulator. In some embodiments, the activation interlock comprises a signal corresponding to a placement status of the first neural stimulator and/or the second neural stimulator, wherein the controller is configured to prevent delivery of the first neural stimulator and/or the second neural stimulator based on the signal.

In some embodiments, 1) the first stimulation is based on receiving a first electric current from the controller, and 2) the second stimulation is based on receiving a second electric current from the controller. In some embodiments, one or both of the first electric current and the second electric current comprises a pulse profile, sine wave profile, square wave profile, triangular wave profile, sawtooth up or down profiles, a constant current, random values selected (randomized current delivered to the electrodes), or a combination thereof. In some embodiments, the first set of stimulation parameters correspond to the first electric current, and wherein the second set of stimulation parameters correspond to the second electric current. In some embodiments, one or both of the first set of stimulation parameters and the second set of parameters comprises an amplitude, frequency, total duration of electric current cycle to be delivered, frequency of durations of electric current cycle to be delivered, minimum pulse width, duty cycle, total number of cycles of to deliver, or a combination thereof. In some embodiments, the pre-determined temporal sequence comprises delivering the first stimulation and the second stimulation simultaneously, sequentially, a combination thereof, or any coordinated temporal manner. In some embodiments, the one or more structures is configured to be wearable by the patient. In some embodiments, the one or more structures comprises a visor, a hat, goggles, or other wearable device for a patient's face or head. In some embodiments, the one or more structures comprises a fastening means to secure the device housing to the patient. In some embodiments, the fastening means comprises a strap, a band, a belt, or a combination thereof. In some embodiments, the fastening means is adjustable, thereby enabling a positioning of the device housing against the patient to be tightened or loosened. In some embodiments, the one or more structures comprises a first electrode housing configured to hold one or both of the first neural stimulator and the second neural stimulator, wherein the first neural stimulator comprises a first electrode, and the second neural stimulator comprises a second electrode. In some embodiments, the first electrode is configured to contact a first skin site of the patient corresponding to the first target nerve, wherein the second electrode is configured to contact a second skin site of the patient corresponding to the second target nerve. In some embodiments, the first electrode housing is flexible, so as to ensure secure contact between the first electrode and the first skin site, and to ensure secure contact between the second electrode and the second skin site. In some embodiments, the first electrode housing is detachably coupled to the fastening means. In some embodiments, the first electrode housing is rotatably coupled to the fastening means. In some embodiments, the one or more structures comprises a second electrode housing coupled to the first electrode housing, wherein the first electrode housing holds the first electrode, and the second electrode housing holds the second electrode. In some embodiments, the second electrode housing is coupled to the first electrode housing via a wired connection. In some embodiments, one or more of the first or second stimulations are one or more of electrical, mechanical, vibratory, acoustic, optical, or thermal. In some embodiments, one or more of the first or second stimulations are provided at a frequency between 0.2 and 200 Hz. In some embodiments, one or more of the first or second stimulations are provided at a current of between 0.1 and 10 mA. In some embodiments, one or more of the first or second stimulations are provided at a pulse width between 1 us and 2 s. In some embodiments, one or more of the first or second stimulation are biphasic.

In some embodiments, the device assembly further comprising an interface for receiving 1) the first set of stimulation parameters corresponding to the first stimulation, and/or 2) the second set of stimulation parameters corresponding to the second stimulation, wherein the interface is in operative communication with the controller, wherein the interface is disposed with the one or more structures. In some embodiments, the interface comprises a graphical user interface (GUI).

Disclosed herein, in another aspect, is a method for stimulating a plurality of target nerves in a patient, the method comprising: a) selecting 1) a first set of stimulation parameters for a first stimulation targeting a first target nerve of the plurality of target nerves, and 2) a second set of stimulation parameters for a second stimulation targeting a second target nerve of the plurality of target nerves, wherein the first target nerve is different from the second target nerve; b) providing a temporal coordination for a delivery of the first stimulation and a delivery of the second stimulation to obtain a desired physiological effect on the patient; c) delivering the first stimulation and the second stimulation according to the temporal coordination, wherein the first stimulation is delivered through a first neural stimulator coupled to the patient, and the second stimulation is delivered through a second neural stimulator coupled to the patient and spaced apart from the first neural stimulator; and d) adjusting one or both of the first set of stimulation parameters and the second set of stimulation parameters based on a patient feedback. Disclosed herein, in another aspect, is a method comprising: selecting 1) a first set of stimulation parameters for a first stimulation targeting a first target nerve of the plurality of target nerves, and 2) a second set of stimulation parameters for a second stimulation targeting a second target nerve of the plurality of target nerves, wherein the first target nerve is different from the second target nerve; providing a temporal coordination for a delivery of the first stimulation and a delivery of the second stimulation to obtain a desired physiological effect on the patient; and delivering the first stimulation and the second stimulation according to the temporal coordination, wherein the first stimulation is delivered through a first neural stimulator coupled to the patient, and the second stimulation is delivered through a second neural stimulator coupled to the patient and spaced apart from the first neural stimulator. In some embodiments, the method further includes adjusting one or both of the first set of stimulation parameters and the second set of stimulation parameters based on a patient feedback.

In some embodiments, the adjusting of one or both of the first set of stimulation parameters and the second set of stimulation parameters is via a controller, wherein the controller is in operative communication with the first neural stimulator and the second neural stimulator. In some embodiments, the selecting of one or both of the first set of stimulation parameters and the second set of stimulation parameters is via an interface in operative communication with the controller. In some embodiments, the patient feedback comprises a patient tolerability, a physiological parameter, or both. In some embodiments, the physiological parameter comprises a muscle contraction, a blood oxygenation level, or both. In some embodiments, the temporal coordination comprises the delivery of the first stimulation and the second stimulation according to a pre-determined sequence. In some embodiments, the pre-determined sequence comprises delivering the first stimulation and the second stimulation simultaneously, sequentially, a combination thereof, or in any coordinated manner.

In some embodiments, the physiological effect comprises a change to a physiological parameter as compared to prior to delivering one or both of the first stimulation and the second stimulation, wherein the change in a physiological parameter comprises an increased cerebral blood flow comp, down-regulating an immune response, modulation a nitric oxide expression, interrupting an ischemic depolarization, or a combination thereof. In some embodiments, the physiological effect comprises the innervation at the nucleus tractus solitarius (NTS) sensory nuclei in the brainstem, the spinal trigeminal nucleus, the superior salivatory nucleus, and/or the rostral ventromedial medulla.

In some embodiments, the first neural stimulator comprises a first electrode, and the second neural stimulator comprises a second electrode. In some embodiments, 1) the first stimulation is based on a first electric current delivered to the first electrode, and 2) the second stimulation is based on a second electric current delivered to the second electrode. In some embodiments, one or both of the first electric current and the second electric current comprises a pulse profile, sine wave profile, square wave profile, triangular wave profile, sawtooth up or down profiles, a constant current, random values selected (randomized current delivered to the electrodes), or a combination thereof. In some embodiments, the first set of stimulation parameters correspond to the first electric current, and wherein the second set of stimulation parameters correspond to the second electric current. In some embodiments, one or both of the first set of stimulation parameters and the second set of parameters comprises an amplitude, frequency, total duration of electric current cycle to be delivered, frequency of durations of electric current cycle to be delivered, minimum pulse width, duty cycle, total number of cycles of to deliver, or a combination thereof. In some embodiments, for any method described herein, further comprising any ES device described herein. In some embodiments, one or more of the first or second stimulations are one or more of electrical, mechanical, vibratory, acoustic, optical, or thermal. In some embodiments, one or more of the first or second stimulations are provided at a frequency between 0.2 and 200 Hz. In some embodiments, one or more of the first or second stimulations are provided at a current of between 0.1 and 200 mA. In some embodiments, one or more of the first or second stimulations are provided at a pulse width be-tween 1 us and 2 s. In some embodiments, one or more of the first or second stimulation energies provide a charge of between 0.5 mC to 200 mC. In some embodiments, one or more of the first or second stimulation are biphasic. In some embodiments, one or more of the first or second stimulations are provided with one or more randomized stimulation parameters, the one or more stimulation parameters comprising one or more of pulse width, frequency, or amplitude. In some embodiments, the first and second electrical stimulation are delivered within 24 hours of an insult to the subject. In some embodiments, the insult is a stroke. In some embodiments, the first and second stimulation energies are delivered at a first ratio of first to second stimulation energy for a first time period, wherein the first and second stimulation energies are delivered at a second ratio of first to second stimulation energy for a second time period, wherein the first and second ratios are different, and wherein the second time period is after the first time period. In some embodiments, the method further includes determining whether reperfusion has occurred in the subject. In some embodiments, the method further includes changing a rate of delivering one or more of the first or second stimulation energies in response to an occurrence of reperfusion in the subject.

Disclosed herein, in another aspect, is a method for stimulating a plurality of target nerve branches in a patient, the method comprising: a) providing a temporal coordination for a delivery of a first stimulation and a delivery of a second stimulation to obtain a desired physiological effect on the patient; and b) delivering the first stimulation and the second stimulation according to the temporal coordination, wherein the first stimulation is delivered through a first neural stimulator coupled to the patient, and the second stimulation is delivered through a second neural stimulator coupled to the patient and spaced apart from the first neural stimulator, wherein the first stimulation is delivered according to a first set of stimulation parameters for targeting a first target nerve of the plurality of target nerves, and wherein the second stimulation is delivered according to a second set of stimulation parameters for targeting a second target nerve of the plurality of target nerves.

Disclosed herein, in another aspect, is a method for slowing cerebral brain damage due ischemic stroke, the method comprising: a) selecting 1) a first set of stimulation parameters for a first stimulation targeting a first target nerve of the plurality of target nerves, and 2) a second set of stimulation parameters for a second stimulation targeting a second target nerve of the plurality of target nerves, wherein the first target nerve branch is different from the second target nerve branch; b) providing a temporal coordination for a delivery of the first stimulation and a delivery of the second stimulation to obtain a desired physiological effect on the patient; c) delivering the first stimulation and the second stimulation according to the temporal coordination, wherein the first stimulation is delivered through a first neural stimulator coupled to the patient, and the second stimulation is delivered through a second neural stimulator coupled to the patient and spaced apart from the first neural stimulator; and d) adjusting one or both of the first set of stimulation parameters and the second set of stimulation parameters based on a patient feedback.

Disclosed herein, in another aspect, is a method for mitigating traumatic brain injury, the method comprising: a) selecting 1) a first set of stimulation parameters for a first stimulation targeting a first target nerve of the plurality of target nerves, and 2) a second set of stimulation parameters for a second stimulation targeting a second target nerve of the plurality of target nerves, wherein the first target nerve branch is different from the second target nerve branch; b) providing a temporal coordination for a delivery of the first stimulation and a delivery of the second stimulation to obtain a desired physiological effect on the patient; c) delivering the first stimulation and the second stimulation according to the temporal coordination, wherein the first stimulation is delivered through a first neural stimulator coupled to the patient, and the second stimulation is delivered through a second neural stimulator coupled to the patient and spaced apart from the first neural stimulator; and d) adjusting one or both of the first set of stimulation parameters and the second set of stimulation parameters based on a patient feedback.

Disclosed herein, in another aspect, is a method for treating subarachnoid hemorrhage, the method comprising: a) selecting 1) a first set of stimulation parameters for a first stimulation targeting a first target nerve of the plurality of target nerves, and 2) a second set of stimulation parameters for a second stimulation targeting a second target nerve of the plurality of target nerves, wherein the first target nerve branch is different from the second target nerve branch; b) providing a temporal coordination for a delivery of the first stimulation and a delivery of the second stimulation to obtain a desired physiological effect on the patient; c) delivering the first stimulation and the second stimulation according to the temporal coordination, wherein the first stimulation is delivered through a first neural stimulator coupled to the patient, and the second stimulation is delivered through a second neural stimulator coupled to the patient and spaced apart from the first neural stimulator; and d) adjusting one or both of the first set of stimulation parameters and the second set of stimulation parameters based on a patient feedback.

Disclosed herein, in another aspect, is a method for treating inflammation, the method comprising: a) selecting 1) a first set of stimulation parameters for a first stimulation targeting a first target nerve of the plurality of target nerves, and 2) a second set of stimulation parameters for a second stimulation targeting a second target nerve of the plurality of target nerves, wherein the first target nerve branch is different from the second target nerve branch; b) providing a temporal coordination for a delivery of the first stimulation and a delivery of the second stimulation to obtain a desired physiological effect on the patient; c) delivering the first stimulation and the second stimulation according to the temporal coordination, wherein the first stimulation is delivered through a first neural stimulator coupled to the patient, and the second stimulation is delivered through a second neural stimulator coupled to the patient and spaced apart from the first neural stimulator; and d) adjusting one or both of the first set of stimulation parameters and the second set of stimulation parameters based on a patient feedback.

Disclosed herein, in another aspect, is a method for treating hypotension, the method comprising: a) selecting 1) a first set of stimulation parameters for a first stimulation targeting a first target nerve of the plurality of target nerves, and 2) a second set of stimulation parameters for a second stimulation targeting a second target nerve of the plurality of target nerves, wherein the first target nerve branch is different from the second target nerve branch; b) providing a temporal coordination for a delivery of the first stimulation and a delivery of the second stimulation to obtain a desired physiological effect on the patient; c) delivering the first stimulation and the second stimulation according to the temporal coordination, wherein the first stimulation is delivered through a first neural stimulator coupled to the patient, and the second stimulation is delivered through a second neural stimulator coupled to the patient and spaced apart from the first neural stimulator; and d) adjusting one or both of the first set of stimulation parameters and the second set of stimulation parameters based on a patient feedback.

Disclosed herein, in another aspect, is a method for modulating the blood brain barrier, the method comprising: a) selecting 1) a first set of stimulation parameters for a first stimulation targeting a first target nerve of the plurality of target nerves, and 2) a second set of stimulation parameters for a second stimulation targeting a second target nerve of the plurality of target nerves, wherein the first target nerve branch is different from the second target nerve branch; b) providing a temporal coordination for a delivery of the first stimulation and a delivery of the second stimulation to obtain a desired physiological effect on the patient; c) delivering the first stimulation and the second stimulation according to the temporal coordination, wherein the first stimulation is delivered through a first neural stimulator coupled to the patient, and the second stimulation is delivered through a second neural stimulator coupled to the patient and spaced apart from the first neural stimulator; and d) adjusting one or both of the first set of stimulation parameters and the second set of stimulation parameters based on a patient feedback.

Disclosed herein, in another aspect, is a method for modulating the glial-lymphatic or glymphatic flow pathways, the method comprising: a) selecting 1) a first set of stimulation parameters for a first stimulation targeting a first target nerve of the plurality of target nerves, and 2) a second set of stimulation parameters for a second stimulation targeting a second target nerve of the plurality of target nerves, wherein the first target nerve branch is different from the second target nerve branch; b) providing a temporal coordination for a delivery of the first stimulation and a delivery of the second stimulation to obtain a desired physiological effect on the patient; c) delivering the first stimulation and the second stimulation according to the temporal coordination, wherein the first stimulation is delivered through a first neural stimulator coupled to the patient, and the second stimulation is delivered through a second neural stimulator coupled to the patient and spaced apart from the first neural stimulator; and d) adjusting one or both of the first set of stimulation parameters and the second set of stimulation parameters based on a patient feedback.

Disclosed herein, in another aspect, is a method for stimulating a plurality of target nerve branches in a patient, the method comprising: a) providing any device described herein; b) providing patient information to the device via an interface; c) based on the patient information, determining via a pre-determined algorithm in communication with the controller one or more of i) the first set of stimulation parameters, ii) the second set of stimulation parameters, and iii) the pre-determined temporal sequence; and d) delivering the first stimulation and/or the second stimulation according to the pre-determined temporal sequence. In some embodiments, the determining in (c) is automatically determined based on the patient information. In some embodiments, the patient information comprises time elapsed since onset of a symptom, national institutes of health stroke scale level (NIHSS), age, stroke history, blood pressure, blood flow, stroke location, stroke location vessel size, collateral score, past medical history, injury type, or any combination thereof. In some embodiments, the stroke location comprises a side of an occluded vessel, and/or a side for cases in which contralateral or ipsilateral stimulation is used or desirable. In some embodiments, the past medical history comprises whether the patient has received or will receive thrombolysis or thrombectomy. In some embodiments, the injury type comprises hemorrhagic stroke, ischemic stroke, traumatic brain injury, and/or other injuries. In some embodiments, the pre-determined temporal sequence comprises delivering the first stimulation and the second stimulation simultaneously, sequentially, in an alternating manner, any combination thereof, or any coordinated temporal manner.

Disclosed herein, in another aspect, is a method of stimulating a plurality of target nerves in a subject to treat a medical condition, the method comprising: transcutaneously delivering a first stimulation energy to a supraorbital branch of a trigeminal nerve; transcutaneously delivering a second stimulation energy to an auricular branch of a vagal nerve, wherein the first and second stimulation energies are delivered simultaneously to treat the medical condition. Disclosed herein, in another aspect, is a method of stimulating a plurality of target nerves in a subject to treat a medical condition, the method comprising: transcutaneously delivering a first stimulation energy to a supraorbital branch of a trigeminal nerve; transcutaneously delivering a second stimulation energy to an auricular branch of a vagal nerve, wherein the first and second stimulation energies are delivered sequentially to treat the medical condition. In some embodiments, the method further includes adjusting one or both of the first set of stimulation parameters and the second set of stimulation parameters based on a patient feedback.

Disclosed herein, in another aspect, is a method of stimulating a plurality of target nerves in a subject to treat a medical condition, the method comprising: transcutaneously delivering a first stimulation energy to a supratrochlear branch of a trigeminal nerve; and transcutaneously delivering a second stimulation energy to an auriculotemporal branch of a trigeminal nerve, wherein the first and second stimulation energies are delivered in combination to treat the medical condition.

Disclosed herein, in another aspect, is a method for modulating mild cognitive impairment, the method comprising: selecting 1) a first set of stimulation parameters for a first stimulation targeting a first target nerve of the plurality of target nerves, and 2) a second set of stimulation parameters for a second stimulation targeting a second target nerve of the plurality of target nerves, wherein the first target nerve branch is different from the second target nerve branch; providing a temporal coordination for a delivery of the first stimulation and a delivery of the second stimulation to obtain a desired physiological effect on the patient; and delivering the first stimulation and the second stimulation according to the temporal coordination, wherein the first stimulation is delivered through a first neural stimulator coupled to the patient, and the second stimulation is delivered through a second neural stimulator coupled to the patient and spaced apart from the first neural stimulator. In some embodiments, the method includes, adjusting one or both of the first set of stimulation parameters and the second set of stimulation parameters based on a patient feedback.

Disclosed herein, in another aspect, is a method of stimulating a plurality of target nerves in a subject to treat a medical condition, the method comprising: transcutaneously delivering a first stimulation energy to a supratrochlear branch of a trigeminal nerve; and transcutaneously delivering a second stimulation energy to an auriculotemporal branch of a trigeminal nerve, wherein the first and second stimulation energies are delivered in combination to treat the medical condition.

BRIEF DESCRIPTION OF THE DRAWINGS

For a more complete understanding of the present invention, including features and advantages, reference is now made to the detailed description of the invention along with the accompanying figures.

DETAILED DESCRIPTION

Figure 1:
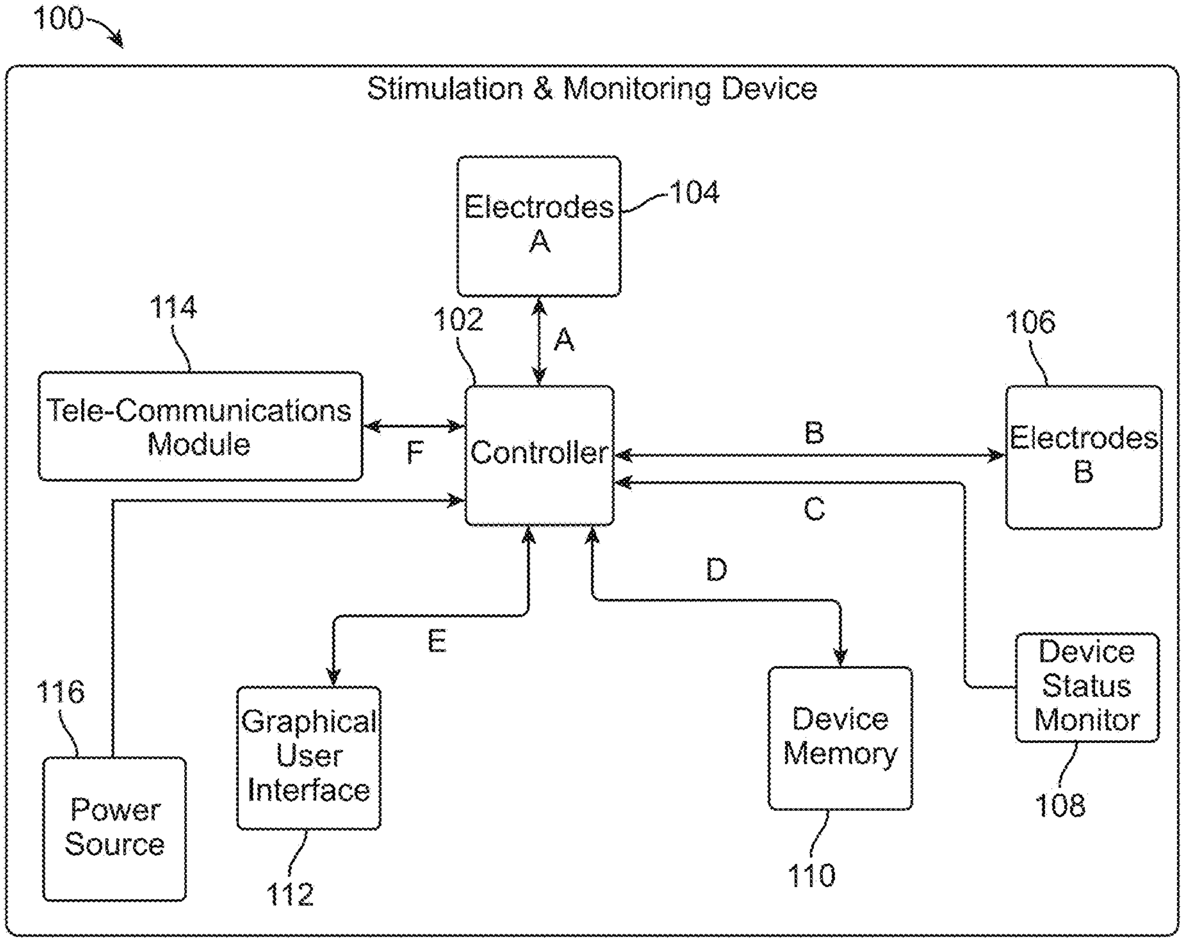
FIG. 1 provides an exemplary functional diagram for components of an embodiment of a stimulation device disclosed herein.

Provided herein are devices, systems, and methods for treating a medical condition through a coordinated stimulation of two or more target nerves. In some embodiments, the stimulation comprises electrical stimulation delivered to a patient. In some embodiments, the coordinated stimulation comprises the two or more target nerves being stimulated in parallel, in series, a combination thereof, or any coordinated temporal sequence. In some embodiments, the stimulation delivery is contingent on an electrode placement confirmation via one or more electrode monitors. In some embodiments, the delivered electrical stimulation comprises one or more stimulation parameters configured to be adjusted based on feedback from the patient. In some embodiments, the feedback comprises automatic detection of a patient physiological parameter or other patient response (e.g. muscle spasm or contraction detection). In some embodiments, the feedback comprises patient provided input, such as verbally or visually (e.g., facial expression, gestures). In some embodiments, the one or more stimulation parameters are automatically randomized over a normal distribution.

In some embodiments, disclosed herein, are systems, devices, and methods configured for combined transcutaneous and/or minimally invasive stimulation of the auricular branch of the vagus nerve and branches of the trigeminal nerve to slow cerebral brain damage by increasing cerebral blood flow, down-regulating the immune response, modulating nitric oxide expression, and/or interrupting ischemic depolarization, in the setting of ischemic stroke. In some embodiments, a physiological monitoring system comprising an electroencephalogram (EEG), near-infrared spectroscopy, or other technology is capable of detecting cerebral blood flow, and/or any other key vital to monitor and provide safe stimulation ranges.

Medical Condition

As described herein, the devices, systems and methods are configured for treating a medical condition through a coordinated stimulation of two or more targeted nerves. In some embodiments, the medical condition comprises ischemic stroke, traumatic brain injury, intracranial hemorrhage (e.g., subarachnoid hemorrhage, subdural hematoma, epidural hematoma, intracerebral hemorrhage, etc.), vasospasm, cardiac arrhythmia, other conditions that involve loss of blood flow or ischemia, inflammatory diseases, conditions that can be managed through inflammatory modulation (e.g., rheumatoid arthritis, irritable bowel syndrome, sepsis, renal ischemia, trauma/hemorrhagic shock, acute lung injury, hyperinflammation, etc.), hypotension, disorders of consciousness, headache or other facial pain, other diseases that cause pain, neurological conditions (e.g., Alzheimer's Disease, Mild Cognitive Impairment, etc.), ocular conditions, infectious diseases, auditory deficits, hypoxia, or a combination thereof. In some embodiments, the devices, systems, and methods described herein are configured to help ease intraprocedural complications and/or help regulate homeostasis in the central nervous system (CNS).

Target Nerves

In some embodiments, target nerve, as used herein, refers to any of the following: 1) a single target nerve corresponding to one or more locations on a single branch of the target nerve; 2) a single target nerve corresponding to one or more locations on two different branches of the target nerve. For example, the supraorbital nerve comprises nerve branches located on both sides of a patient head, wherein systems and methods described herein may be configured to stimulate one or both branches.

In some embodiments, the target nerve(s) comprises a vagus nerve, a trigeminal nerve, a facial nerve, an auricular nerve, or a combination thereof. In some embodiments, the target nerve(s) consists of neural ganglion (ganglia) or nucleus (nuclei) comprising sphenopalatine ganglion, geniculate ganglion, otic ganglion, ciliary ganglion, nucleus ambiguous, spinal trigeminal nucleus, solitary nucleus, trigeminal ganglion, or some combination thereof. In some embodiments, the vagus nerve comprises an auricular branch, a pharyngeal nerve, a superior laryngeal nerve, superior cervical cardiac branches of the vagus nerve, or a combination thereof. In some embodiments, the trigeminal nerve comprises an auriculotemporal branch, a supratrochlear branch, a supraorbital branch, a maxillary branch, an ophthalmic branch, infraorbital branch, or a combination thereof. In some embodiments, the facial nerve comprises the greater petrosal nerve, nerve to the stapedius, chorda tympani, posterior auricular nerve, temporal branch, zygomatic branch, buccal branch, marginal mandibular branch, cervical branch, or a combination thereof. In some embodiments, an auricular nerve comprises the anterior branch of the greater auricular nerve, the posterior branch of the greater auricular nerve, a cutaneous branch, the nerve origin at the cervical plexus, or any combination thereof. In some embodiments, the target nerve(s), nucleus (nuclei), ganglion (ganglia), or some combination thereof comprises a sympathetic nerve, a parasympathetic nerve, a sensory nerve, a motor nerve, or a combination thereof. In some embodiments, the target nerve(s) comprises of sensory nerve fiber(s) Aα, Aβ, Aδ, C, or a combination thereof. In some embodiments, the target nerve fiber(s) comprise of diameters range from 0.2 to 25 μm.

In some embodiments, systems and methods described herein are configured to target a nucleus (e.g., nucleus tractus solitarius (NTS) sensory nuclei in the brainstem, spinal trigeminal nucleus, the superior salivatory nucleus, and/or the rostral ventromedial medulla). In some embodiments, targeting a nucleus comprises 1) appropriate charge density at a required depth, 2) minimally invasive approach, and/or 3) indirect activation through downstream stimulation (via peripheral nerves).

Nerve Stimulation

As described herein, in some embodiments, systems, devices, and methods are configured to stimulate two or more target nerves to treat a medical condition. In some embodiments, the target nerves are stimulated via electrical stimulation, thermal stimulation, mechanical stimulation, chemical stimulation, or a combination thereof. In some embodiments, electrical stimulation comprises delivering an electric current (e.g., electric impulses) to a patient to stimulate the respective target nerves. In some embodiments, the electric delivery is transcutaneous. In some embodiments, the electric delivery is percutaneous. In some embodiments, the electric delivery is subcutaneous. In some embodiments, chemical stimulation comprises delivering one or more pharmaceuticals, a menthol, and/or capsaicin to one or more target nerves. In some embodiments, thermal stimulation comprises delivering one or more laser pulses to one or more target nerves, and/or using a thermoelectric heat pump.

Stimulation Device

As described herein, in some embodiments, a device is configured to stimulate two or more target nerves so as to treat a medical condition. In some embodiments, the target nerves are stimulated via electrical stimulation, thermal stimulation, mechanical stimulation, chemical stimulation, or a combination thereof. In some embodiments, electrical stimulation comprises delivering an electric current (e.g., electric impulses) to a patient to stimulate the respective target nerves.

In some embodiments, the device comprises an electrical stimulation device ("ES device"), which comprises a current controller, a power source, a user interface for receiving user input, a programming unit, and/or one or more electrodes. In some embodiments, electric current is delivered to the user by the ES device through a transcutaneous approach and/or through a percutaneous approach. In some embodiments, one or more electrodes are configured for transcutaneous stimulation of a target nerve via an electric current delivered to the one or more electrodes. In some embodiments, one or more electrodes are configured for percutaneous stimulation of a target neve via an electric current delivered to the one or more electrodes. In some embodiments, the ES device further comprises one or more electrode monitors configured to monitor the placement of the electrodes on a patient, as described herein.

In some embodiments, the user interface comprises a graphical user interface (GUI). In some embodiments, the device does not comprise a user interface, but only an activation trigger to turn the device on/off. In some embodiments, the device is configured to be in a constant state of activation. In some embodiments, the ES device further comprises telecommunication hardware for communication with another computing device, a server, a cloud network, and/or another stimulation device. In some embodiments, the ES device further comprises and/or is in communication with one or more physiological monitors, each physiological monitor configured to provide information relating to a physiological characteristic.

In some embodiments, the ES device comprises an ES device housing configured to hold/support the components of the ES device. In some embodiments, the ES device housing enables the one or more electrodes to be placed against the skin of a patient to enable stimulation of one or more target nerves. In some embodiments, the ES device housing is wearable. In some embodiments, the ES device housing comprises an electrode housing that is configured to place the one or more electrodes in contact with a skin of the patient.

FIG. 1 depicts an exemplary functional diagram for one embodiment of the ES device 100 described herein. In some embodiments, the modules and components provided in FIG. 1 are all provided on a single, standalone structure. In some embodiments, certain modules and/or components of an ES device described herein are provided on two or more structures (e.g., FIG. 2).

In some embodiments, with reference to FIG. 1, the ES device comprises a power source 116, a controller 102, a first set of electrodes ("Electrodes A") 104 targeting a first target nerve, a second set of electrodes ("Electrodes B") 106 targeting a second target nerve, and an interface (e.g., a GUI 112). In some embodiments, the power source 116 supplies power to the controller 102. In some embodiments, the controller 102 receives input from the interface 112, such as an amount of electric current to be delivered to a set of electrodes, a stimulation profile of an electric current to be delivered, modifications to a stimulation profile of an electric current to be delivered, etc. In some embodiments, the controller 102 is configured to deliver a pre-determined current or voltage to the two sets of electrodes 104, 106. In some embodiments, each set of electrodes comprises an electrode monitor that monitors the placement of the electrode, and is configured to send an electrode placement status signal to the controller. In some embodiments, each set of electrodes 104, 106 comprises an anode electrode and a cathode electrode. In some embodiments, an alternate to a set of electrodes 104, 106 is a single electrode used instead. For example, an exemplary single electrode that can be used is a bipolar needle.

In some embodiments, the ES device 100 further comprises a device status monitor 108 configured to monitor parameters relating to the ES device, such as battery life remaining, battery charging status, etc. In some embodiments the ES device further comprises a tele-communications module 114 configured to transmit/receive signals from other computing devices, a server, a cloud network, a computer network, and/or another ES device. In some embodiments, the ES device comprises one or more physiological monitors (not shown) configured to measure a physiological parameter. In some embodiments, the one or more physiological monitors are configured to measure pulse rate, blood pressure, mean arterial pressure, neural monitoring (e.g., via EEG), blood oxygenation levels, or a combination thereof. In some embodiments, the one or more physiological parameters are separate from the device, but in communication with the controller.

Each of the device components are further described herein.

Controller

In some embodiments, the controller 102 of the ES device is configured to receive power from the power source 116. In some embodiments the power is received via an electrical signal. In some embodiments, the controller is configured to modulate the power received to deliver a pre-determined stimulation (i.e., electric current or voltage) to the patient via the electrodes (e.g., 104, 106). In some embodiments, as described herein, the controller 102 is in communication with the interface 112 and configured to modulate the current delivered to the sets of electrodes based on input received from a user and/or patient via the interface 112. In one embodiment, the controller comprises a current source, a current sink, a digital-to-analog converter, and/or a microcontroller. In some embodiments, the microcontroller is in operative communication with the interface 112. In some embodiments, the current source receives current from the power source, and provides a fixed amount of a current that is then split between the current sink and the sets of electrodes (e.g., 104, 106) connected to the patient. In some embodiments, as described herein, the current sink receives a fixed current independent of the impedance of the electrodes but controllable by a signal from a digital-to-analog signal converter (DAC). In some embodiments, the difference between the current supplied by the current source and the current that flows into the current sink is passed through the electrodes to the patient. In this manner, the amount of current applied to the patient is controlled. In some embodiments, the current provided by the current source is at least about 0.1 mA, at least about 1 mA, at least about 2.5 mA, at least about 3.5 mA, at least about 5 mA, at least about 10 mA, at least about 25 mA, at least about 50 mA, at least about 75 mA, at least about 100 mA, at least about 200 mA, or at least about 500 mA.

In some embodiments, the current sink is configured to be modulated to vary the current delivered to the patient (i.e. to the sets of electrodes). In some embodiments, the current sink is varied in response to a precise input voltage. In some embodiments, the current sink can vary the current received in the range of, for example, 0 mA to about 10 mA. In some embodiments, the precise input voltage is set by a digital-to-analog signal converter (DAC). In some embodiments, the input voltage is provided via the interface (as described herein) based on a desired current level, wherein the controller would correspond that current level to a voltage signal, which is sent to the DAC to control the amount of current "sunk". In some embodiments, the DAC comprises Texas Instruments DAC7311. In some embodiments, by increasing the current passing into the current sink, less current will be delivered to the patient (via the electrodes). Accordingly, in some embodiments, the current (stimulation) delivered to the patient can range from 0 mA to the current that can be sunk by the current sink. For example, if the current source supplies 4 mA and the current sink can sink between 0 and 10 mA, the range of current applied to the patient can be controlled to be between −6 mA to 4 mA. In some embodiments, the current delivered to the patient is selected to be any value within the range of current supplied from a current source or the amount of current configured to be sunk by the current sink or higher. In some embodiments, the current is configured to be delivered in a negative manner such that the anode and cathode electrodes are switched (as described herein). In some embodiments, the controller is configured to deliver only a specific stimulation profile to each of the sets of electrode, wherein the stimulation profile cannot be adjusted. In such embodiments, the interface may be limited to just power activation, or there may not be an interface included with the device.

As described herein, in some embodiments, the controller 102 is configured to deliver a pre-determined current to the sets of electrodes, and thereby configured to deliver a pre-determined stimulation to one or more target nerves. In some embodiments, each stimulation delivered is based on a stimulation profile. In some embodiments, the stimulation profile comprises delivering a stimulation using electrical signals (e.g., delivering current to the electrodes) according to sine waves, pulses, square waves, triangular waves, sawtooth up or down profiles, a constant current, random values selected (randomized current delivered to the electrodes), or a combination thereof. In some embodiments, each stimulation delivered to a patient is according to a stimulation profile specified by a user or patient (e.g., via the interface in communication with the controller). In some embodiments, each set of electrodes (e.g., 104, 106) may receive a stimulation according to a specific stimulation profile. In some embodiments, the stimulation profile of a stimulation (e.g., current) delivered to a first set of electrodes 104 is the same or different as the stimulation profile of a stimulation delivered to a second set of electrodes 106.

In some embodiments, each stimulation profile comprises one or more stimulation parameters. In some embodiments, the one or more stimulation parameters comprises the corresponding amplitude and/or frequency of a cycle for a stimulation profile being delivered (e.g., amplitude and frequency of a sine wave), the total duration of the cycle to be delivered, the frequency of those durations, minimum pulse width, duty cycle, and/or the total number of cycles to deliver. In some embodiments, as described herein, the one or more stimulation parameters may be modified via input by the user or patient through the interface. For example, in some embodiments, wherein the stimulation profile to be delivered to a set of electrodes comprises a sine wave profile, the user is able to adjust associated stimulation parameters such as the amplitude and frequency of the sine wave, the total duration of the sine wave to be delivered, the frequency of these durations, and/or the total number of sine waves to deliver. In another example, in some embodiments, wherein the stimulation profile to be delivered to a set of electrodes comprises a pulse profile, the user is able to adjust associated stimulation parameters such as pulse width, amplitude, number of pulses, frequency of pulses, total time of stimulation delivered, or a combination thereof.

In some embodiments, the anode and cathode electrodes of a given set of electrodes (e.g., 104, 106) are configured to be alternated between each pulse or cycle, such that the electrical field generated (about the patient) is opposite of that generated by the prior pulse or cycle. In some embodiments, this alternating current profile reduces the sensation felt by the patient being stimulated and may make the stimulation more tolerable at the same amplitude of stimulation being delivered. In another embodiment, the pulse width delivered can be made to be a random value constrained between two predetermined values, such as between 100 microseconds and 1000 microseconds. In some embodiments, the pulse width can be varied to be randomly generated along a normal distribution with a predetermined mean and standard deviation, such as 250 microseconds mean with a 75 microsecond standard deviation. In some embodiments, the frequency of pulse delivery may also be altered on a random or normal distribution such that the period of time between successive pulses is not consistent between any two pulses. In some embodiments, such altered frequency of pulse delivery prevents habituation to the stimulation that may occur with a fixed frequency or fixed pulse width. In some embodiments the stimulation current delivered is adjusted in response to a measured potential difference across two electrodes of a given set of electrodes described herein. For example, the stimulation current may be higher in a first one anode/cathode configuration than another set of electrodes (another anode/cathode configuration) in response to a positive potential difference measured between the first anode/cathode configuration to correct the potential difference back to zero. In some embodiments, the randomization of the frequency or amplitude of the stimulation may be constrained to ensure that the charge applied to the tissue is maintained in a balanced manner. In these embodiments, the controller could calculate the charge applied by analyzing sum of the product of the pulse width and the amplitude over a fixed time period (for example 1 second) and make determinations about the next pulse or series of pulses that should be applied to balance the charge delivered to the tissue. This determination could be further constrained by device programming to limit the maximum or minimum pulse width, frequency, or amplitude delivered.

As described herein, in some embodiments, modulating the one or more stimulation parameters (e.g., the frequency of stimulation and/or minimum pulse width) are driven by limitations of the operational amplifiers used in the current source, current sink and by the communication frequency to the DAC (e.g., the communication frequency to the DAC can range from 0 to about 50 MHz). In some embodiments, stimulation frequencies are lower in the range of 0-1 kHz with pulse widths of 0.1-10 msec.

As described herein, in some embodiments, the controller is configured to specify a stimulation profile for a stimulation to be delivered to a given set of electrodes. In some embodiments, controller is configured to coordinate the timing of electric current being delivered to one or more sets of electrodes, and thereby coordinate the timing of stimulation for specific target nerves that correspond with the one or more sets of electrodes. In some embodiments, the controller is configured to stimulate two or more target nerves simultaneously, in series, a combination thereof, or any coordinate temporal sequence (via coordinated timing of delivering current to the respective sets of electrodes).

In some embodiments, a user manually starts, resumes, or stops current delivery to a set of electrodes via the interface. In some embodiments, the controller is configured to automatically start, resume, or stop delivery of the current to a set of electrodes based on feedback received from the set of electrodes and/or a corresponding electrode monitor. In some embodiments, such feedback acts as an interlock for operation of the device. In some embodiments, feedback from the set of electrodes and/or electrode monitor comprises impedance measured between a set of electrodes (e.g., 104, 106), temperature of an electrode of a set of electrodes, temperature of a patient skin surface corresponding to placement of a set of electrodes, or a combination thereof. In some embodiments, the feedback received from the set of electrodes and/or an electrode monitor is used by the controller to monitor electrode placement and functionality. In some embodiments, wherein the feedback from an electrode monitor suggests improper electrode placement (e.g., due to insufficient contact, as measured via impendence between a set of electrodes for example) or improper functionality, the controller is configured to automatically stop delivery of current to the corresponding set of electrodes. In some embodiments, improper functionality corresponds to the device (as described herein) or electrode monitor (or electrodes themselves) identifying the electrodes as not delivering a proper amount of current due to a higher than expected impedance between electrodes. For example, a patient having dirt or other material (e.g., cosmetics, make-up) on their skin may require the device to provide a larger voltage than the device is capable of delivering so as to deliver a current corresponding to a desired stimulation for a target nerve. Accordingly, in this example, the device may recognize improper functionality and stop delivery of a stimulation. In some embodiments, the device provides an alert or action required, e.g., via the interface, such as indicating to the user to wipe clean the patient's skin. In some embodiments, once the feedback from the set of electrodes and/or an electrode monitor indicates proper electrode placement and/or functionality (for a set of electrodes), the controller is configured to start or resume delivery of current to the corresponding set of electrodes, and thereby start or resume delivery of a stimulation to the associated target nerve(s).

In some embodiments, a plurality of sets of electrodes are configured to stimulate a target nerve. As described herein, in some embodiments, an alternate to a set of electrodes comprises a single electrode (e.g., a bipolar needle). In some embodiments, a plurality of sets of electrodes are located in a target area (site) on the patient, configured to stimulate the same target nerve(s). In some embodiments, the device is configured to measure and monitor resistance between any pair (e.g. set) of electrodes and choose to deliver stimulation between the pair with the least or lesser resistance that is in the target area.

In some embodiments, the microcontroller is in operative communication with the DAC through an isolation circuit (e.g., Silicon Labs S18630). An exemplary microcontroller comprises the (MicroChip ATMega328). In this manner, the grounding of the microcontroller and interface (e.g., GUI) can be kept separate from the grounding of the rest of the controller circuitry, preventing single-fault grounding and isolating the patient from the electrical mains the microcontroller or GUI may use for their power.

In some embodiments, the microcontroller is configured to be in operative communication with a memory component (e.g., a non-volatile memory component) to store different stimulation profiles that can be selected via user input from the interface for the electric current to be delivered to a given set of electrodes. These stimulation profiles can be sent in series through use of a buffer in the firmware of the device. For example, in some embodiments, the controller changes a voltage that alters the current delivered to the corresponding set of electrodes. In some embodiments, this voltage is changed on a MHz frequency such that any stimulation profile can be accomplished. In some embodiments, the buffer enables, for an array of voltage values that are programmed into the memory for example, to be loaded one-by-one (the voltage values) by the controller and passed to the DAC. As each individual point of the stimulation profile is sent to the DAC, a new point of the stimulation profile can be loaded from the memory of the device.

As described herein, in some embodiments, the stimulation profile specified for a stimulation delivered to any set of electrodes is based on factors such as the tolerability of a patient, a physiological monitor measured, etc. In some embodiments, the controller receives input from a user to change a stimulation profile, for example, based on the tolerability of the patient. As described herein, in some embodiments, the input is received by the interface, which may be in the form of a rotating dial, directional arrow buttons, a button cycling through parameters, direct input of parameters, other variations, or a combination thereof. In some embodiments, the input received changes the electrical field generated by the current delivered (to a set of electrodes) to change the sensation felt by the patient during stimulation. In some embodiments, the stimulation profile is adjusted to alter the sensation felt by the patient to a tolerable level for the duration of the simulation (with respect to the current delivered to any of the sets of electrodes). In some embodiments, the input received by the user results in scaling of the pulse width, the current delivered to the patient, or the duty cycle. In one example, the current delivered to the patient is gradually increased by 0.1 mA per level until a patient deems that the electrical stimulation is intolerable due to pain, muscle contraction, or other sensation. In some embodiments, a dial (e.g., on the interface) is adjusted to a level or two lower than the tolerability threshold for the remaining duration of the stimulation protocol. In some embodiments, the controller is configured to scale the stimulation in between each pulse. In some embodiments, the stimulation profile is scaled based on the average value for particular parameters (e.g., the average current delivered is scaled such that there may be instances of stimulation delivery that are both above and below that value). In some embodiments, the stimulation profile is scaled within a pre-defined therapeutic range based on patient tolerability, sensation, or input. In some embodiments, patient tolerability can be assessed by changing a single first parameter while other parameters remain fixed; then, a therapeutic dose can be delivered by modulating a different parameter than the first around an average determined by the first parameter for tolerability.

In some embodiments, the input received by the user (for specifying a stimulation profile of the current delivered to a set of electrodes) is configured to be detected via sensors that capture the result of stimulation. For example, in some embodiments, sensors (e.g., gyroscope, accelerometer, motion detector, etc.) are able to detect muscle contractions at the site of stimulation, such that if stimulation results in unwanted muscular effects, or a lack of a muscular effect, the stimulation parameters are adjusted by the controller automatically. Accordingly, in some embodiments, such sensors, are in communication with the controller. In some embodiments, this capture of muscle contraction is in place for any number of muscle and nerve combinations. In some embodiments, an example of muscle contraction being in place is with respect to the frontals muscle contractions due to unwanted facial nerve stimulation.

Interface

In some embodiments, as described herein, the ES device comprises a user interface that is in operative communication with the controller. In some embodiments, the interface is a graphical user interface (GUI). With reference to FIG. 1, in some embodiments, the GUI 112 is configured to display information received by the controller 102. In some embodiments, the GUI 112 is configured to display information received from one or more physiological monitors, a set of electrodes (104, 106) or and/or a corresponding electrode monitor, the device status monitor 108, the device memory 110, and/or the tele-communications module 114. For example, in some embodiments, the GUI 112 is configured to display the remaining device battery life for the device. In some embodiments, the one or more physiological monitors comprise monitoring pulse rate, blood pressure, mean arterial pressure, neural monitoring (e.g., via EEG), blood oxygenation levels, blood flow velocity and/or pulsatility index, calculations of tissue perfusion, brain functional activity, or a combination thereof. As described herein, in some embodiments, a user, via the GUI, is able to modify and/or specify parameters of the stimulation delivered (current delivered), such as the respective stimulation profile, locations of stimulation, and/or duration of stimulation, and program these components into the controller.

In some embodiments, with reference to FIG. 1, an interface 112 provides an interface between the device and a user (e.g., physician, medical staff, caregiver) and/or the patient. In some embodiments, the GUI 1) allows the user to control the ES device 100, 2) allows the user to provide input to the device (as described herein), 3) displays information about the device current state to the user, 4) displays information sensed from the patient (e.g., physiological parameters as described herein), 5) displays information provided from a remote user (e.g., remote physician of clinician) that is communicated to the local user (e.g., a local physician, clinician or patient), or 6) a combination thereof. In some embodiments, the user is able to select a stimulation profile (via the GUI) relating to the current delivered to a given set of electrodes, and further be able to alter certain stimulation parameters (as described herein). In one embodiment, the GUI allows the user to select from pre-determined stimulation parameters (for a corresponding stimulation profile) stored in the memory of the device, thereby allowing the type of stimulation delivered for a specific target nerve(s) to be specified. In some embodiments, a user is able to input through the GUI information relevant to the progression of the patient's condition or treatment. This information may include time since symptom onset, clinical assessments (such as NIH stroke scale), vitals information (such as blood pressure, heart rate, respiratory rate, blood oximetry, or cerebral oximetry), occlusion location, occlusion etiology, time of reperfusion, planned or conducted treatments, diagnosis (for example acute ischemic stroke, traumatic brain injury, subarachnoid hemorrhage, or hypotension), or any combination thereof. In some embodiments, the device is able to use this information to coordinate stimulation between multiple nerve targets (as described herein) or make suggestions (as described herein, see "Coordination of Multiple Nerve Stimulation Targets" for example) to the user to coordinate stimulation between multiple nerve targets over time in relation to disease progression.

In some embodiments, the GUI displays information about the ES device to the user (e.g., patient or clinician). In some embodiment, the information about the ES device comprises the battery charging status, the battery voltage remaining, the battery life remaining, and/or the estimated time until complete battery discharge, electrode placement status, resistance measured between electrodes, warning indication about high resistance between placed electrodes to indicate poor contact, or a combination thereof. In some embodiments, the GUI displays the current stimulation profile chosen for each set of electrodes, the number of stimulation pulses delivered, the time of delivery, the time remaining of delivery, and/or the number of pulses remaining in the delivery.

In some embodiments, the GUI displays patient specific information collected during an initial evaluation as well as new information collected by the device. In some embodiments, the patient specific information is displayed to the physician (remote or local), the patient, medical staff, and/or caregivers involved in the patients' care. In some embodiments, the patient specific information is received via one or more physiological monitors, as described herein (e.g., near infrared spectroscopy, EEG, pulse oximeter, etc.). In some embodiments, the patient specific information is received via the telecommunication module and/or via manual input. In some embodiments, the patient specific information comprises measurement such as electrode resistance, cerebral blood flow measurements, EEG waves measured, heart rate, blood pressure, pulse oxygen level, cerebral oxygenation, cerebral metabolic rate, blood flow velocity, partial pressure of oxygen in the brain tissue, National Institute of Health stroke scale, contraindications for thrombolytic therapy, relevant stroke patient history, other physiological measures, or a combination thereof Electrodes In some embodiments, as described herein, the ES device 100 comprises one or more sets of electrodes 104, 106 that are configured to be coupled to a patient. In some embodiments, the controller is in operative communication with the electrodes 104, 106. In some embodiments, the controller is configured to deliver electric current to the sets of electrodes. In some embodiments, the controller is configured to specify a stimulation profile for the corresponding current delivered to each set of electrode. In some embodiments, the location of each set of electrodes on a patient is specified to stimulate a corresponding target nerve(s) by receiving electric current from the controller. In some embodiments, more than one set of electrodes may be located on the patient to target the same target nerve(s). In some embodiments, one or more sets of electrodes may be located on the patient to target a first target nerve(s) and one or more sets of different electrodes may be located on the patient to target a second target nerve(s).

In some embodiments, the controller is configured to receive information from the electrodes (e.g., 104, 106) and/or corresponding electrode monitors. In some embodiments, the information received by the controller from the electrodes and/or electrode monitors comprises impedance measured between the electrodes, temperature of the electrode, and/or temperature of a patient skin surface. In some embodiments, the information received by the controller from the electrodes and/or electrode monitors is used by the controller to monitor electrode placement and functionality.

In some embodiments, the ES device delivers the stimulation to the patient transcutaneously through the combination of two or more electrodes placed on the patient's skin. In some embodiments, the electrodes comprise hydrogel material, sponge material, metallic surfaces, and/or are formed from other electrically conductive materials that will promote contact with the patient's skin. In certain configurations, electrode gel may be used to help promote conductive between the electrodes and the patient's skin. In other configurations, the electrodes are contained in a housing (as described herein) that is in contact with the patient's skin. In some embodiments, the housing would contain an electrically conductive component. In some embodiments, the housing comprise hydrogel material, sponge material, metallic surfaces, and/or are formed from other electrically conductive materials that will promote contact with the patient's skin.

In some embodiments, the electrodes deliver the stimulation percutaneously to the patient through the combination of two or more electrodes placed beneath the patient's skin. In some embodiments, the electrodes comprise two or more small needles. In some embodiments, percutaneous placement of the electrodes enables the electrical stimulation to be delivered closer to the target nerve(s).

In some embodiments, the location of the electrode placements relative to the patient is fixed. In some embodiments, wherein the location of the electrodes relative to the patient is fixed, the electrodes are provided and/or integrated with a stimulation device housing. In some embodiments, the ES device housing comprises an elastic headband, a fixed structure headgear, an ear clip, a part of goggles or other wearable eyewear, or a combination thereof. In some embodiments, the stimulation device housing is configured to be adjusted to accommodate different types of patient anatomy. In some embodiments, the electrodes are housed individually on translatable and/or rotatable carriers to allow adjustment relative to the stimulation device housing, thereby helping ensure the electrodes adequately contact the patient skin surface.

In some embodiments, the ES device housing comprises a semi-rigid electrode housing in which the housing is able to flex towards the patient's face while the relative position of the electrodes to each other remains relatively constant. In some embodiments, such configuration to enable the housing to flex towards the patient's face is via providing a housing constructed from a material such as polyurethane rubber. In some embodiments, the housing is constructed from a composite of materials such that a layer of closed-cell foam is bonded to the electrode housing.

In some embodiments, the location of the electrode placements relative to the patient is moveable by a user (e.g., physician) and/or the patient. In some embodiments, wherein the location of the electrodes is moveable, one or more electrodes are provided as individual devices that are adhered directly to the skin surface using an adherent gel or with external fixation (such as tape). In some embodiments, wherein the location of the electrodes is alterable, one or more electrodes are provided as a single device that are adhered directly to the skin surface using an adherent gel or with external fixation (such as tape). In some embodiments, said individual devices comprises a flexible and/or self-adherent pad. For example, in some embodiments, the electrodes are not fixed within a housing and could be placed at one or more target locations as indicated by a user so as to enable stimulation of one or more target nerves. In some embodiments, the electrodes are wired to the same or one or more controllers and power units.

In some embodiments, individual sets of electrodes have their own controller and would interface with a common or dedicated programming unit that coordinates the stimulation between the different sets of electrodes (as described herein). In some embodiments, the electrodes are contained within a layered adhesive strip of which one layer is a conductive material that would promote electrical contact with the patient's skin.

Figure 2:
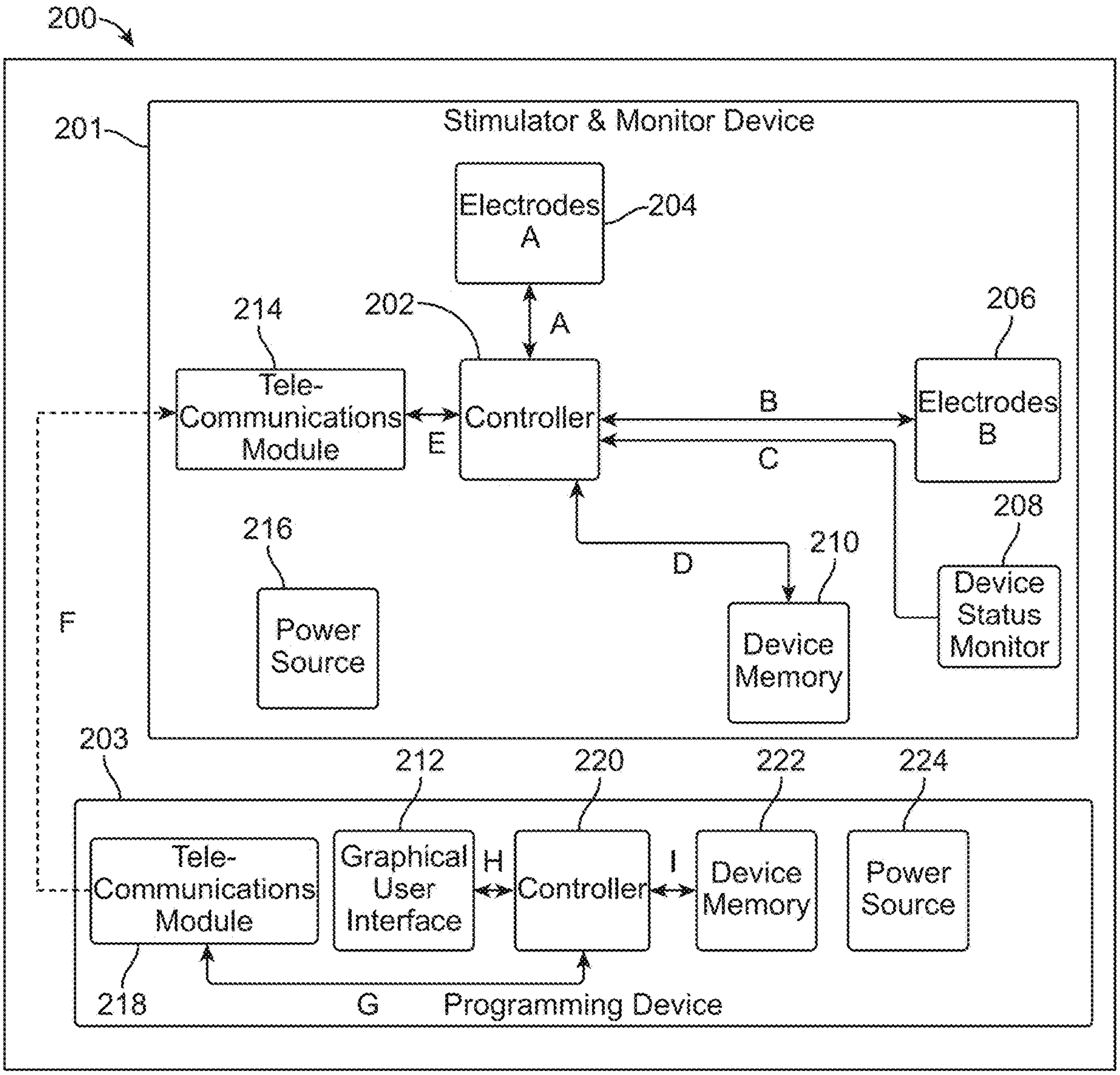
FIG. 2 provides an exemplary functional diagram for components of another embodiment of a stimulation device disclosed herein.

In some embodiments, the locations of the electrodes relative to the patient during operation of the device are set by the corresponding stimulation device housing, the physician, or both. In one example, the stimulation is applied to the supraorbital nerve and the supratrochlear nerve using one or more electrodes applied to the forehead while also applying stimulation to the auricular branch of the vagus nerve using a set of electrodes applied the cymba concha of the ear. Other locations of interest to stimulate could include the auriculotemporal branch of the trigeminal nerve, the frontal nerve, the lacrimal nerve, the nasociliary nerve, infraorbital nerve, superior alveolar nerve, buccal nerve, submandibular ganglion, mental nerve, ophthalmic nerve, anterior ethmoid nerve, trigeminal nerve, pons, trigeminal ganglion, maxillary nerve, mandibular nerve, pterygopalatine ganglion, facial nerve, chorda tympani, inferior alveolar nerve, lingual nerve, mylohyoid nerve, inferior alveolar nerve, posterior auricular nerve, external nasal nerve, zygomaticotemporal, zygomaticofacial, and/or the great auricular nerve. With reference to FIGS. 1-2, in some embodiments the first set of electrodes is located on a device to target the first target nerve at a single location on the patient, and the second set of electrodes is located on the device to target the second target nerve at another single specific location on the patient. In some embodiments, the first set of electrodes comprises one or more electrodes targeting the first target nerve at two or more different locations. For example, wherein the first target nerve comprises the supraorbital nerve, the first set of electrodes comprises one or more electrodes targeting the supraorbital nerve on the left side of the patient head, and one or more electrodes targeting the supraorbital nerve on the right side of the patient head. Similarly, in some embodiments, the second set of electrodes comprises one or more electrodes targeting the second target nerve at two or more different locations. In some embodiments, as described herein, the two or more different locations of a target nerve refer to two or more locations on a single branch of the target nerve and/or one or more locations on two or more different branches of the target nerve.

In some embodiments, the ES device housing and/or electrode housing of different ES device will differ by the target nerves desired to be stimulated, the purpose for the stimulation, and/or location of the patient (e.g., hospital setting). For example, in some embodiments, a patient requiring significant bed rest or monitoring in the hospital, such as for subarachnoid hemorrhage patients, the electrodes are housed within a fixed variation in the form factor of a flat, flexible patch placed over one or more target nerves in the cheek or forehead, or as a visor that sits over the forehead. In these embodiments, an ear clip or an elastic headband may not be included.

FIGS. 6-7 described herein provide exemplary ES device housings with electrodes configured to be located thereon to target one or more target nerves.

Monitoring Components

In some embodiments, the stimulation device comprises one or more physiological monitors configured to measure one or more physiological parameters. In some embodiments, the one or more physiological parameters are relevant to the user (e.g., physician) to determine and/or describe progression of a patient's condition. In some embodiments, the one or more physiological monitors are configured to measure pulse rate, blood pressure, mean arterial pressure, neural monitoring (e.g., via EEG), blood oxygenation levels, or a combination thereof. In some embodiments, the one or more physiological parameters comprises measurements of cortical electrical activity through EEG monitoring, measurements of tissue oxygenation through near-infrared spectroscopy, blood oxygenation through an oximeter, blood flow velocity and/or pulsatility index through transcranial doppler ultrasound, laser speckle imaging, or through diffusion correlation spectroscopy, cerebral metabolism through combination of measures from near-infrared spectroscopy and diffusion correlation spectroscopy, or a combination thereof. In some embodiments, sensors are used to measure muscle contraction on a patient in response to a stimulation received. In some embodiments, such sensors configured to measure muscle contractions comprise an accelerometer, a gyroscope, a motion detector, and/or the like. In some embodiments, any combination of these physiological measurements could be used to generate information relating to the progression of a patient's condition As described herein, in some embodiments, the stimulation device comprises one or more electrode monitors configured to analyze a corresponding set of electrodes (as described herein). In some embodiments, the electrode monitors are configured to measure the impedance between a set of electrodes, to ensure proper functionality. In some embodiments, the electrode monitors are in operative communication with the controller 102.

Device Status

In some embodiments, the ES device 100 comprises a status monitor 108 for monitoring parameters of the ES device. In some embodiments, the controller 102 is in operative communication with the status monitor 108. In some embodiments, the status monitor 108 is configured to monitor and/or record parameters of the ES device. In some embodiments, the controller 102 is configured to receive information from the status monitor 108 relating to the parameters of the ES device. In some embodiments, the parameters of the ES device comprise battery life, charging status, GPS location, elapsed time since the ES device was powered on, or a combination thereof. In some embodiments, the parameters of the device include other clinically relevant timepoints. For example, in some embodiments, clinically relevant time points relating to ischemic stroke comprise time of last known well, time that a thrombolytic agent was administered, the time of last NIHSS assessment, the time the patient enters the hospital.

Memory

In some embodiments, the ES device 100 comprises a memory module 110 for storing and retrieving information. In some embodiments, the controller 102 is in operative communication with the memory module 110. In some embodiments, the controller 102 is configured to store information in the memory module. In some embodiments, the controller 102 is configured to retrieve information from the memory module 110. In some embodiments, the information stored and/or received comprise information received via a graphical user interface (GUI) 112, a telecommunications module 114, the electrodes 104, 106 and/or corresponding electrode monitors, the device status monitor 108, or a combination thereof. In some embodiments, the information from the tele-communication module 114 comprises a desired stimulation profile, past stimulation profiles, or a combination thereof. In some embodiments, the information from the device status monitor 108, the electrodes 104,106 and/or the corresponding electrode monitors comprise information received from said components by the controller 102 as described herein.

Tele-Communications Module

Figure 4:
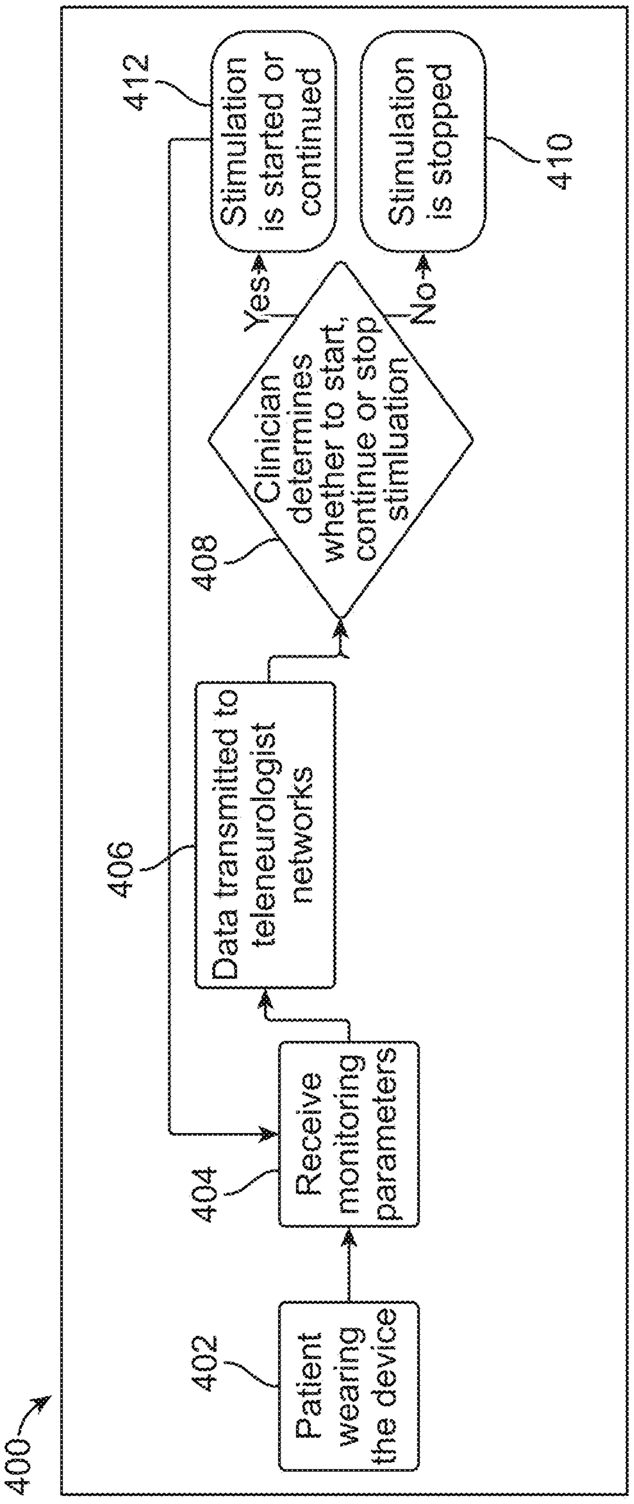
FIG. 4 provides an exemplary flow chart for a telemedicine algorithm for nerve stimulation, for an embodiment disclosed herein.

In some embodiments, the ES device comprises a telecommunications module 114. In some embodiments, the controller 102 is configured to be in operative communication with the tele-communications module 114. In some embodiments, the tele-communications module 114 is in operative communication with a mobile or web application. In some embodiments, the mobile or web application comprises a software application external to the ES device. In some embodiments, the mobile application comprises a smart device (e.g., smart phone, tablet, etc.). In some embodiments, the mobile or web application is stored on a cloud server. In some embodiments, the controller 102 is configured to transmit and/or receive information with the mobile or web application via the tele-communication module 114. In some embodiments, the information sent and/or received with the mobile or web application comprises information sent and/or received from the device status monitor 108, the device memory 110, the tele-communications module 114, the interface 112, and/or electrodes 104, 106 (and/or corresponding electrode monitors), as described herein. In some embodiments, the information sent and/or received with the mobile or web application enables a remote user (e.g., a remote physician) to review and/or modify the device parameters, and/or enable the remote physician to review patient data collected. FIG. 4 depicts an exemplary flowchart of data/information being sent and/or received from a remote user (e.g., physician, clinician). In some embodiments, a device (as described herein) being worn by a patient 402, is configured to receive data/information 404 from one or more physiological parameters or other monitoring information (including for example, electrode monitoring, stimulation delivery, etc.). In some embodiments, the received information is displayed on an interface of the device (as described herein). In some embodiments, the data/information is transmitted 406 to a remove physician (e.g., a tele-neurologist via directly to the tele-neurologist or through a tele-neurologist network). In some embodiments, the physician determines 408 whether to start, continue, or stop delivering a stimulation (via the device) based on the data/information received. In some embodiments, wherein the physician decides the stimulation should be stopped, a signal is sent to the controller of the device (e.g., via the telecommunication module as described herein) to stop delivery of the stimulation 410. In some embodiments, wherein the physician decides the stimulation can start or continue 412, the device continues to deliver a stimulation, or starts delivery (via a signal being sent to the controller, via the tele-communication module). In some embodiments, the remote user (e.g., physician, clinician) provides a message to a local user to start, continue, or stop stimulation delivery based on the information/data received.

In some embodiments, the ES device comprises a fail-safe configuration wherein the tele-communications module is configured to detect a lack or loss of a network connection and/or communication with a remote computing device, and subsequently configured to automatically instruct the controller to stop stimulation (as a result of the detected lack or loss of network connection and/or communication to a remote computing device).

Power Source

In some embodiments, the ES device comprises a power source 116. In some embodiments, the power source stores power, and delivers power to the ES device. In some embodiments, the power source 116 delivers power to the electrodes (104,106), the device status monitor 108, the device memory 110, the interface 112, and/or the controller 102.

In some embodiments, the power source 116 of the ES device supplies power to the controller 102. In some embodiments, the power source comprises batteries, a connection to a power outlet, or both. In some embodiments, the power source 116 comprises a plurality of batteries. For example, in one embodiment, the power source 116 comprises two sets of batteries (for example 4 AA batteries in series per set) to form a bi-polar power supply. In some embodiments, the two sets of batteries are connected in series with each other. In some embodiments, the ground of the controller 102, which may be shared with the ground of the electrodes (104, 106), is electrically connected to the connection between the two sets of batteries. In some embodiments, the voltage from each battery pack (e.g., a set of batteries as disclosed herein) can be stepped up using a boost converter to an amount suitable to drive the controller and deliver the required current to the corresponding sets of electrodes. For example, the voltage from each battery pack may be increased from 6V to 36V. In one embodiment, these batteries of the power source are replaceable and configured for single-use. In some embodiments, the batteries are connected to an in-line voltage monitor that can provide an indication to the user that the batteries need to be replaced (e.g. due to reduced capacity). In some embodiments, the indication to the user is through a signal on the interface 112.

In some embodiments, the batteries of the power source for the device are rechargeable. In some embodiments, the rechargeable batteries comprise a lithium ion battery or batteries in series. In some embodiments, the device comprises an input to receive power to enable recharging of the rechargeable batteries. In some embodiments, the charging is controlled using a chip. An exemplary chip for controlling the charging includes ON Semiconductor NCP1854. In some embodiments, charging of the device provides a signal to the charging controller (e.g., chip), and this signal can be used to prevent the microcontroller from delivering a stimulation to the patient to preserve electrical isolation between the patient and the charging ground. In some embodiments, alternative to using a chip to control the charging, the recharging circuit is electrically isolated from the controller. In some embodiments, the batteries are recharged through inductive charging, which may be electrically isolated from the controller.

In some embodiments, as described herein, the device receives power directly from connection to a wall outlet. In some embodiments, for a device described herein (e.g., device 200 in FIG. 2), the device receives power and/or charging from a separated component of the device (e.g., programming component 203).

Other Stimulation Embodiments

In some embodiments, other types of nerve stimulation, such as through the modulation of thermal receptors, mechanoreceptors, chemoreceptors, or other sensory systems are employed. In some embodiments, the other types of nerve stimulation are used in conjunction with or alternative to the electrical stimulation via the ES device described herein. In some embodiments, the other types of nerve stimulation are used in series or in a pattern with electrical stimulation. In some embodiments, the stimulation device is configured to provide one or more types of the other nerve stimulation, in addition to electrical stimulation as described herein. In some embodiments, modes of the other types of nerve stimulation as provided by the ES device or another device comprise thermal energy via heating or cooling, vibrational forces, diffusion of a chemical compound or medicine from the ES device to contact the patient skin, auditory signals, olfactory stimulus, or a combination thereof.

In some embodiments, the stimulation device is further configured to deliver electrical stimulation, thermal stimulation, mechanical stimulation, chemical stimulation, or a combination thereof to the one or more targeted nerves. In some embodiments, the stimulating device comprises a housing configured to hold one or more stimulating elements to enable such nerve stimulation. In some embodiments, the one or more stimulating elements comprises electrodes, thermal receptors, mechanoreceptors, chemoreceptors, or a combination thereof. In some embodiments, the stimulating device is wearable on a patient. In some embodiments, the stimulating device comprises a wearable portion, and a separate portion in operative communication with the stimulating elements.

Safety/Comfort Features

In some embodiments, the noninvasive or minimally invasive approach for stimulating one or more target nerves, as described herein, provides little patient risk, or substantially reduces or removes patient risk for safety. In some embodiments, the ES device described herein comprises additional safety features such as topical anesthetic delivery and/or localized shut-down for poor contact.

In some embodiments, an anesthetic topical agent is provided with the positioning of the electrodes, such that the anesthetic topical agent comes in contact with the area of stimulation or the area adjacent to the area of stimulation on the patient. In some embodiments, the anesthetic agent is in the form of a gel, emollient, liquid, or other composition. In some embodiments, the anesthetic of choice is any combination or concentration of lidocaine, epinephrine, tetracaine, bupivanor, benzocaine, proparacaine, topicaine, aloe vera, clove oil, plantain, chamomile, capsaicin, menthol, pramoxine, zinc acetate, hydrocortisone, and prilocaine.

In some embodiments, the delivery of an anesthetic agent is timed to be immediately prior to stimulation, concurrent with stimulation, or after stimulation has started. In some embodiments, the delivery mechanisms comprise providing a contact surface of the ES device housing with an anesthetic agent that is configured to contact the skin of a patient. In some embodiments, the contact surface of the ES device comprises a foam or sponge-like component. In some embodiments, the contact surface of the ES-device (e.g., foam or sponge-like component) comprises concentrations of the anesthetic agent that is configured to be delivered in small increments when compressed onto a contact point on the patient skin. In some embodiments, during initial set-up of the ES device housing with respect to the patient, a seal is broken that deploys the anesthetic agent from reservoirs within the housing proximal to target locations for stimulation of one or more target nerves. In some embodiments, the contact surfaces are lined with the anesthetic agent and an adhesive agent covered by a removable tape or sticker that helps in ensuring contact throughout the patient stimulation process.

In some embodiments, as described herein, consistent electrode contact is key to appropriate target nerve activation (stimulation) via desired electric current density at target locations. In some embodiments, during patient movement as a part of standard care, the electrode contact could change from an ideal position. In some embodiments, such change in the electrode contact results in a localized shutdown of stimulation. As described herein, such change in electrode contact is detected via impedance measurement via a set of electrodes and/or corresponding electrode monitors. In some embodiments, electrical impedance measured at individual stimulation sites (locations on the skin corresponding to one or more target nerves) is obtained between each stimulation cycle. In some embodiments, if the impedance change is measured to be above a certain threshold, the controller prevents stimulation from occurring at that location for any future planned cycle. In some embodiments, if the impedance returns within the desired range, the controller is configured to resume/restart stimulation as previously planned. In some embodiments, when a change in electrode contact (such as a loss in contact) is detected, an LED on the ES device housing and/or an indicator on the GUI will indicate where contact has been lost or changed.

ES Device Embodiment with Components on Separate Structures

FIG. 2 depicts a functional diagram for another embodiment of an ES device 200 described herein for nerve stimulation of two or more electrodes. In some embodiments, the device 200 comprises a stimulation/monitoring ("SM") component 201 configured for nerve stimulation and electrode monitoring, as described herein. In some embodiments, the stimulation/monitoring component of the ES device 200 comprises a SM power source 216, a SM controller 202, a first set of SM electrodes ("Electrodes A") 204 targeting a first target nerve, a second set of SM electrodes ("Electrodes B") 206 targeting a second target nerve, and a SM tele-communications module 214.

With continued reference to FIG. 2, in some embodiments the ES device 200 further comprises a programming component 203. In some embodiments, the stimulation/monitoring component 201 is provided separated and standalone from the programming component 203. In some embodiments, the stimulation/monitoring component 201 is in operative communication with the programming component 203. In some embodiments, the stimulation/monitoring component 201 is in operative communication with the programming component 203 via a cable (e.g., wired connection), dock (e.g., docked connection), and/or wirelessly (e.g., via Bluetooth, wi-fi, cellular data, etc.). In some embodiments, the stimulation/monitoring component 201 is detachably coupled to the programming component 203. In some embodiments, the stimulation/monitoring component 201 is detachably coupled to the programming component 203 via the dock or cable.

In some embodiments, the SM tele-communication module 214 of the stimulation/monitoring ("SM") component is in operative communication with a programming tele-communication module 218 of the programming component 203. In some embodiments, a programming controller 220 is in communication with the SM controller 202, and configured to send and/or receive information from the SM controller 202 via the respective SM tele-communication module 214 and programming tele-communication module 218. In some embodiments, the programming controller 220 sends to the SM controller 202 information such as a desired stimulation profile and/or stimulation duration to the stimulation/monitoring component (specifically, for one or both sets of the electrodes (204, 206)). In some embodiments, the programming controller 220 receives information from the controller 202 such as the SM device status, and/or a current programmed stimulation profile.

In some embodiments, the programming component 203 comprises an interface 212. In some embodiments, interface 212 is a graphical user interface (GUI). In some embodiments, the programming controller 220 is in operative communication with the GUI 212. In some embodiments, the GUI is configured to display information received by the programming controller 220, which can include information received by the SM controller 202. Accordingly, in some embodiments, the GUI is configured to display information received from the SM device status monitor 208, the SM device memory 210, SM the tele-communications module 214, and/or the SM electrodes 204,206 (and/or corresponding electrode monitors as described herein). For example, in some embodiments, the GUI 212 is configured to display the remaining device battery life for one or both of the SM component 201 and programming component 203. In some embodiments, a user, via the GUI, is able to modify and/or specify parameters of the stimulation delivered, such as the stimulation profile, locations of stimulation, or duration of stimulation, and program these components into the programming controller 220, and in some instances, the SM controller 202.

In some embodiments, the power source 216 supplies power to the controller 202. In some embodiments, the SM controller 202 receives input from the tele-communications module 214 (as described herein), such as an amount of electric current to be delivered to a set of electrodes, a stimulation profile of an electric current to be delivered, modifications to a stimulation profile of an electric current to be delivered, etc. In some embodiments, the SM controller 202 is configured to deliver a pre-determined current or voltage to the two sets of electrodes 204, 206. In some embodiments, each set of electrodes comprises an electrode monitor that monitors the placement of the electrode, and is configured to send an electrode placement status signal to the controller. In some embodiments, each set of electrodes 204, 206 comprises an anode electrode and a cathode electrode.

In some embodiments, the ES device 200 further comprises a device status monitor 208 configured to monitor parameters relating to the ES device 200, such as battery life remaining, battery charging status, etc.

In some embodiments the SM tele-communications module 214 and/or the programming tele-communications module 218 is configured to transmit/receive signals from other computing devices, a server, a computer network, and/or another ES device. In some embodiments, the ES device 200 comprises one or more physiological monitors (not shown) configured to measure a physiological parameter In some embodiments, the components of the ES device 200 operate in the same way and provide the same function as described for similar components of the ES device 100 in FIG. 1.

In some embodiments, the programming component 203 is provided with a separate structure from the SM structure 201. The term programming component and programming unit are used interchangeably herein. In some configurations, the ES device is transported with the patient from one hospital center to another, such as from a primary stoke center (PSC) to a comprehensive stroke center (CSC). For example, in some embodiments, a patient is transferred from PSCs to CSCs to receive a procedure called mechanical thrombectomy to remove the clot. However such cases could lead to a build-up of device inventory at the CSC. In these cases, it would be desirable for the device to be single-use and disposable at the CSC. In some embodiments, to maximize cost effectiveness between single-use devices, and the ability to re-use devices, a portion of the device may be single-use per patient and disposable (e.g., SM component 201) while another portion of the device (e.g., programming component 203) may be configured to be used for multiple patients.

In some embodiments, the programming component is available at each center the patient is transported to and/or in the transport vehicle. As described herein, in some embodiments, the programming component is configured to be in operative communication with a S/M component (e.g., see S/M component 201 from FIG. 2). In some embodiments, the programming component is in operative communication with the SM component via a direct wired connection, and/or wirelessly via Bluetooth, Wi-Fi, RF, cellular data, and/or other means.

In some embodiments, the programming component enables the user (e.g., physician) to select a stimulation profile to be delivered via the ES device. In some embodiments, the SM component stores the stimulation profile selected by the user in the SM device memory (e.g., see reference character 210). Accordingly, in some embodiments, the SM component is configured to continue delivering a stimulation to the patient even when the programming component is disconnected from SM component, wherein the SM component accesses a stimulation profile stored in the SM device memory. As described herein, in some embodiments, the programming component comprises a programming GUI (e.g., see reference character 212 in FIG. 2) that is configured to perform at least some or all of the functions of the GUI as described herein (e.g., as described with reference character 112 in FIG. 1).

Coordination of Multiple Nerve Stimulation Targets

In some embodiments, the controller of a device described herein comprises one or more pre-determined algorithms of stimulation to coordinate the stimulation between two or more different target nerves. As described herein, in some embodiments, target nerves comprise different nerve branches, and/or difference branches of the same nerve. This may be desirable in cases where different mechanisms of action are more important during different periods of the disease progression. Additionally, in some embodiments, interactions between different targets of stimulation may decrease the effect of stimulation if multiple targets are stimulated at the same time. Accordingly, given these differential mechanisms of actions and windows for effectiveness of stimulation, in some embodiments, coordination of stimulation between different target nerves is desirable and increases the effectiveness of a device described herein. In some embodiments, pre-determined algorithms of stimulation implemented by the controller of the device (as described herein) allow for coordination of stimulation between different target nerves, which, in conjunction with user inputs for the time of stimulation start in relation to symptom onset or the time of specific clinical events (such as a reperfusion event) increases the effectiveness of a device described herein. In some embodiments, the pre-determined algorithms are stored and/or executed via a programming unit (as described herein). In some embodiments, the pre-determined algorithms are stored and/or executed via a computing device in communication with the controller and/or programming unit (e.g., via tele-communications module).

In some embodiments, the pre-determined algorithm (as described herein) automatically determines the appropriate stimulation parameters and/or a coordination of stimulation of one or more target nerves based on the input received (e.g., last known well time, time elapsed since symptom onset, etc.). In some embodiments, the pre-determined algorithm in the device automatically provides one or more suggestions for appropriate stimulation parameters (e.g., via a look up algorithm) and/or a coordination of stimulation of one or more target nerves to the physician via the device GUI (as described herein). For example, in some embodiments, the physician enters into the GUI that the patient is 3 hours since symptom onset and the National Institutes of Health Stroke Scale (NIHSS) is 11. Accordingly, in some embodiments, the device then uses a look-up algorithm to determine a set value of trigeminal nerve stimulation (TNS), and a set value of vagus nerve stimulation (VNS) to be applied (based on the input received), and suggests appropriate stimulation parameters to the physician on the GUI. In some embodiments, the physician can alter these suggested values, or choose to apply them. Alternatively, or in addition to, in some embodiments, instead of set values, the device suggests a time-variant curve of stimulation to be applied (such as is shown in FIG. 10B for example) that the physician could then alter or choose to accept. In some embodiments, the physician communicates to the device (for example, via a button or icon on the GUI) to indicate a reperfusion event has occurred. Accordingly, in some embodiments, the device then suggests to turn off TNS and turn on VNS (as shown in FIG. 10A), which would be suggested to the physician to accept or alter.

In some embodiments, the set values, as described herein, comprise parameters such as pulse width, frequency, and amplitude of the stimulation delivery. In some embodiments, one or more parameters are pre-determined based on the input received. In some embodiments, one or more parameters are configured to be adjusted based on a patient condition. For example, in some embodiments, parameters such as pulse width and frequency are pre-determined, while parameters such as amplitude are configured to be adjusted until a certain point such as pain tolerability of the patient or visible muscle contractions.

As described herein, in some embodiments, the pre-determined algorithm uses patient information (which may be entered into the device, for e.g., via a GUI) to automatically determine or suggest a stimulation for one or more target nerves. In some embodiments, the patient information comprises time elapsed since onset of a symptom, national institutes of health stroke scale level (NIHSS), age, stroke history, stroke location, stroke location vessel size, collateral score, past medical history, blood pressure, blood flow, injury type, or a combination thereof. In some embodiments, stroke location comprises a side of an occluded vessel (left/right) or a side of symptoms for cases in which contralateral or ipsilateral stimulation would be desirable. In some embodiments, past medical history comprises whether the patient has or is planned to receive thrombolysis (tPA) or thrombectomy. In some embodiment, injury type includes any injury type described herein, such as hemorrhagic stroke, ischemic stroke, traumatic brain injury, etc.

Figure 10A:
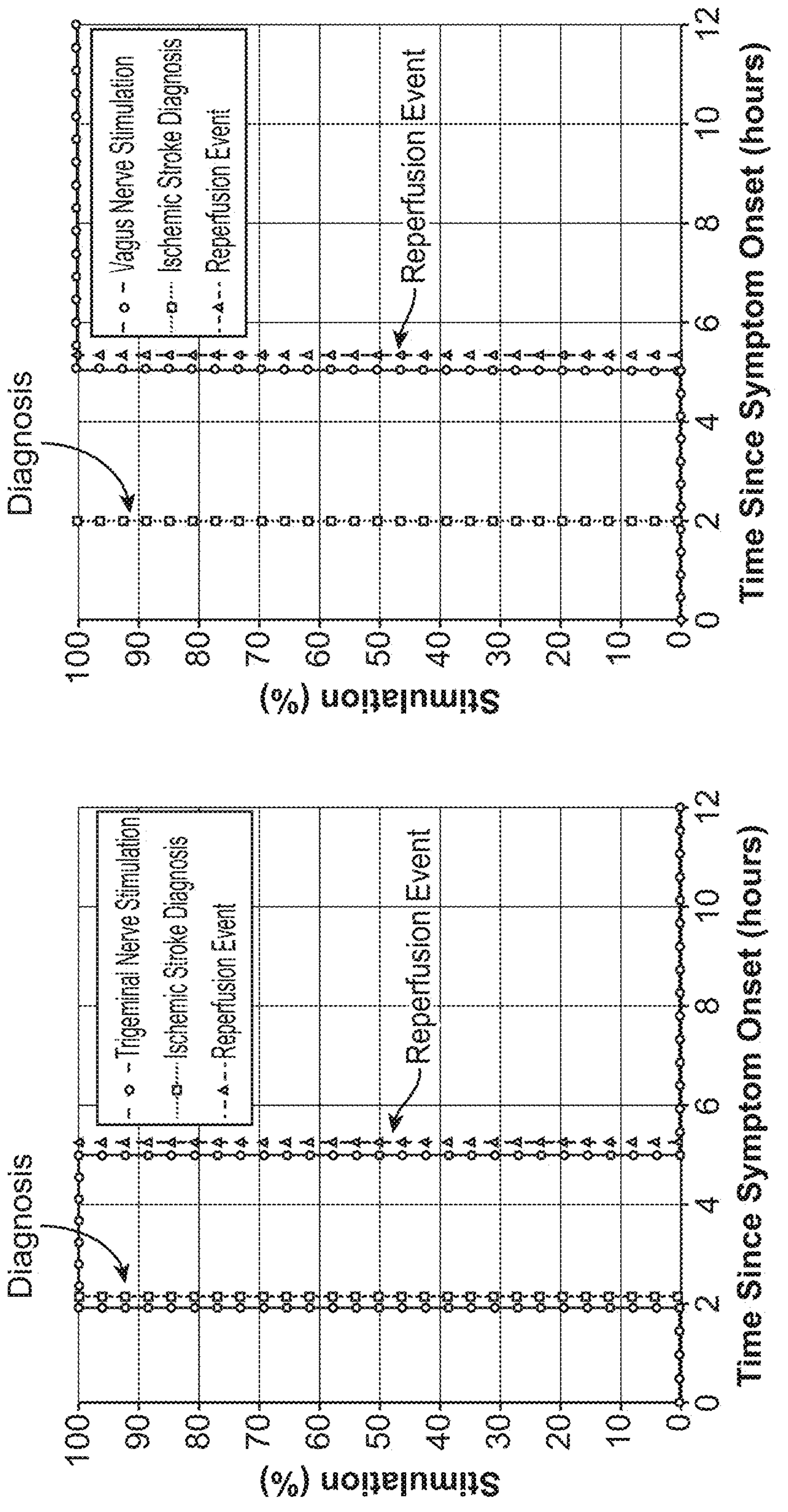
FIG. 10A provides an exemplary depiction of a coordinated stimulation of two target nerves according to an embodiment described herein.
Figure 10B:
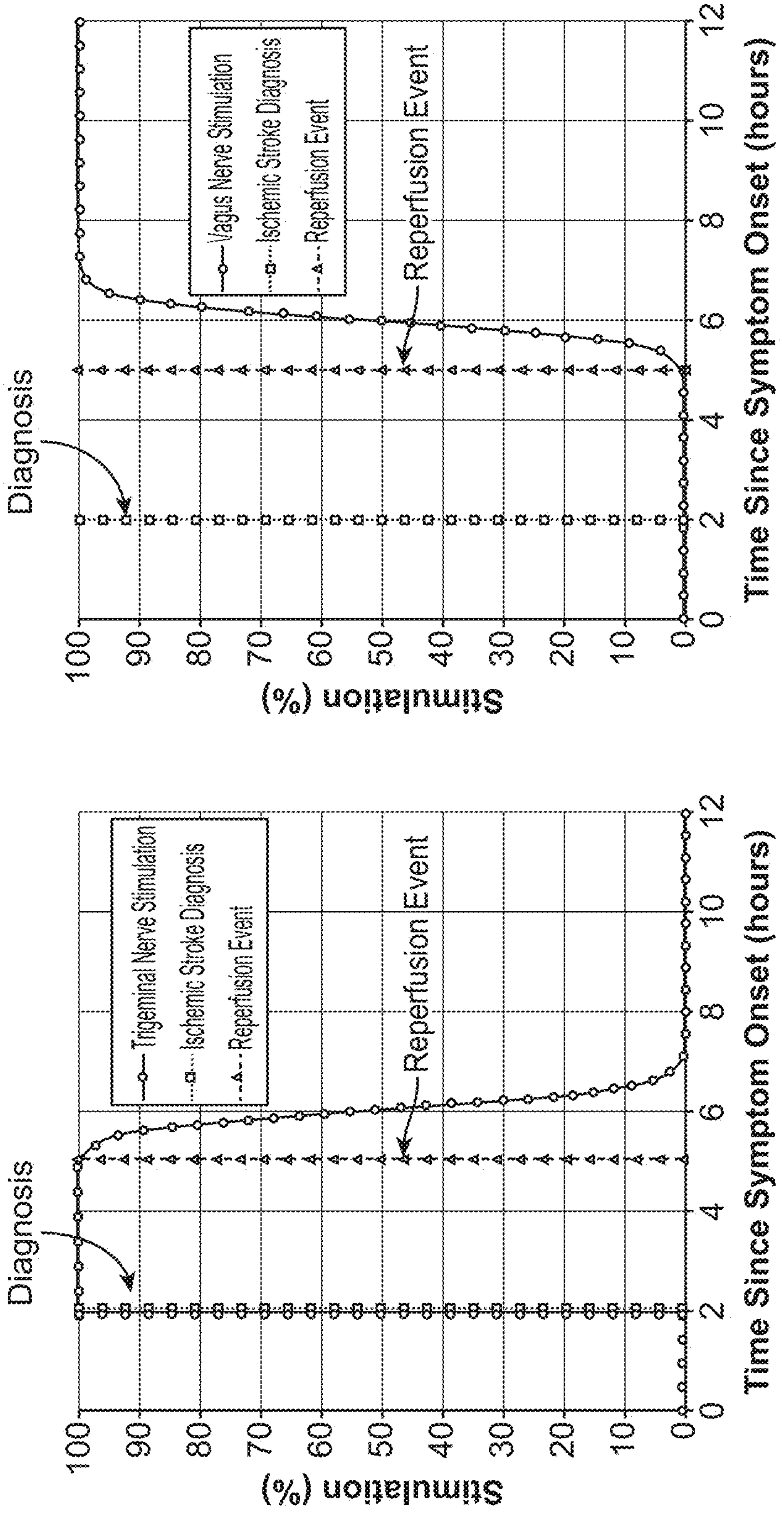
FIG. 10B provides another exemplary depiction of a coordinated stimulation of two target nerves according to an embodiment described herein.

FIG. 10A provides an exemplary flow chart of a method for an embodiment for stimulating two or more target nerves in which trigeminal nerve stimulation occurs from the time of ischemic stroke diagnosis until the time of a reperfusion event, at which point trigeminal nerve stimulation ends and vagus nerve stimulation begins. The change of stimulation targets could alternatively be triggered by a time since symptom onset or by user input in place of the reperfusion event input. In some cases, for example where a cerebral blood vessel is blocked, such as in acute ischemic stroke, a patient may be subjected to reperfusion therapies to reopen the blocked vessel. In some cases, these will be in the form of thrombolysis (ex. tissue plasminogen activator administration) or thrombectomy (ex. mechanical endovascular thrombectomy). In some cases, prior to reperfusion, the aim of treatment is to maximize blood flow and oxygen delivery to the insult region, whereas after reperfusion, the aim of treatment is to limit reperfusion injury and reactive oxygen damage. In this scenario, stimulation of target nerves could be coordinated to maximize the desired aim of treatment prior to reperfusion and after reperfusion. In the embodiment where trigeminal nerve stimulation increases cerebral blood flow, the recruitment of collateral vessels, and/or increases oxygen supply to the damaged tissue, among other effects, and auricular vagus nerve stimulation decreases excitotoxicity, metabolic oxygen demand, and/or reactive oxygen damage, among other effects, stimulation could be coordinated such that trigeminal nerve stimulation occurs in the time period before reperfusion, and vagus nerve stimulation occurs in the time period after reperfusion, as depicted in FIG. 10A. In some embodiments, the time of reperfusion could be communicated to the device through the GUI (as described herein), user inputs on buttons or switches (as described herein), and/or through the tele-communications module of the device (as described herein). In some embodiments, the stimulation of the trigeminal nerve branch occurs from at least about 0 hrs, at least about 0.5 hrs, at least about 1 hr, at least about 1.5 hr, at least about 2 hr, at least about 2.5 hr, at least about 3 hr, at least about 5 hr, at least about 10 hr after system onset. In some embodiments, the duration of the trigeminal nerve branch stimulation is from about 0.1 hr to about 10 hrs. In some embodiments, the duration of the trigeminal nerve branch stimulation is at least about 0 hrs, at least about 0.5 hrs, at least about 1 hr, at least about 1.5 hr, at least about 2 hr, at least about 2.5 hr, at least about 3 hr, at least about 5 hr, at least about 10 hr, at least about 50 hrs. In some embodiments, the duration of the vagus nerve branch stimulation is from about 0.1 hr to about 100 hrs. In some embodiments, the duration of the vagus nerve branch stimulation is at least about 0 hrs, at least about 0.5 hrs, at least about 1 hr, at least about 1.5 hr, at least about 2 hr, at least about 2.5 hr, at least about 3 hr, at least about 5 hr, at least about 10 hr, at least about 50 hrs, at least about 100 hrs.

In other cases, it may be desirable for stimulation of target nerves to be dosed to vary in strength of stimulation in relation to the time since symptom onset to induce different dose-dependent responses corresponding with the disease progression. In some cases, one such clinical scenario is represented by acute ischemic stroke, wherein the time since symptom onset or the time since the patient was last known to be well are important points for clinical decision making, such as whether to administer thrombolysis or to estimate infarct core progression or the presence of salvageable penumbral tissue. In some embodiments, the time since symptom onset or the time since last known well could be programmed into the device by a user through the GUI, user inputs on buttons or switches, and/or through the tele-communications module. In these embodiments, the device would be able to determine which target nerves should be stimulated using predetermined algorithms stored in the device memory. In some embodiments, over time, these target nerves could be adjusted or the relative amplitudes (of the stimulation) between the target nerves could be adjusted to initially induce one mechanism of action while delaying induction of a second mechanism of action until later time points. FIG. 10B provides an exemplary flow chart of a method for an embodiment for stimulating two or more target nerves in which trigeminal nerve stimulation occurs from the time of ischemic stroke diagnosis until the time of a reperfusion event, at which point trigeminal nerve stimulation is decreased over time and vagus nerve stimulation is increased over time. For example, in some cases, such as for an acute ischemic stroke, patient has a last known well time of 2 hours prior to device placement, such that the device may initially prioritize stimulation of branches of the trigeminal nerve to increase cerebral blood flow by setting stimulation parameters to those known to induce this effect, while de-prioritizing vagus nerve stimulation (by reduction of the amplitude or frequency of stimulation). As described herein, in some embodiments, the pre-determined algorithm will look up the stimulation parameters based on the input received (such as including last known well time). As described herein, in some embodiments, some parameters of the stimulation (such as pulse width and frequency) are pre-determined, while other parameters (such as amplitude) could be adjusted based on a patient condition. In some cases, this prioritization schema may last for a fixed duration (such as until between 1 to 48 hours since symptom onset), and then it may be altered such that vagus nerve stimulation is prioritized with parameters known to induce positive effects, while stimulation of branches of the trigeminal nerve is decreased (for example in amplitude or frequency) or ceased completely as depicted in FIG. 10B. In some embodiments, the stimulation of the trigeminal nerve branch occurs from at least about 0 hrs, at least about 0.5 hrs, at least about 1 hr, at least about 1.5 hr, at least about 2 hr, at least about 2.5 hr, at least about 3 hr, at least about 5 hr, at least about 10 hr after system onset. In some embodiments, the duration of the trigeminal nerve branch stimulation is from about 0.1 hr to about 10 hrs. In some embodiments, the duration of the trigeminal nerve branch stimulation is at least about 0 hrs, at least about 0.5 hrs, at least about 1 hr, at least about 1.5 hr, at least about 2 hr, at least about 2.5 hr, at least about 3 hr, at least about 5 hr, at least about 10 hr, at least about 50 hrs. In some embodiments, the duration of the vagus nerve branch stimulation is from about 0.1 hr to about 100 hrs. In some embodiments, the duration of the vagus nerve branch stimulation is at least about 0 hrs, at least about 0.5 hrs, at least about 1 hr, at least about 1.5 hr, at least about 2 hr, at least about 2.5 hr, at least about 3 hr, at least about 5 hr, at least about 10 hr, at least about 50 hrs, at least about 100 hrs.

Alternatively, instead of the device making this decision (as described herein), in some cases, the controller could make a suggestion to the clinician based on the time elapsed since symptom onset and rely on further user input to define the relative amounts of stimulation performed. Alternatively, in some cases, to assist in make this determination or making this recommendation, the device could request further information from the clinician, such as the patient's collateral status, the location of the occlusion, if any reperfusion therapies are planned or have occurred, and/or the patient's clinical status (for example as assessed by the NIH stroke scale).

Figure 10C:
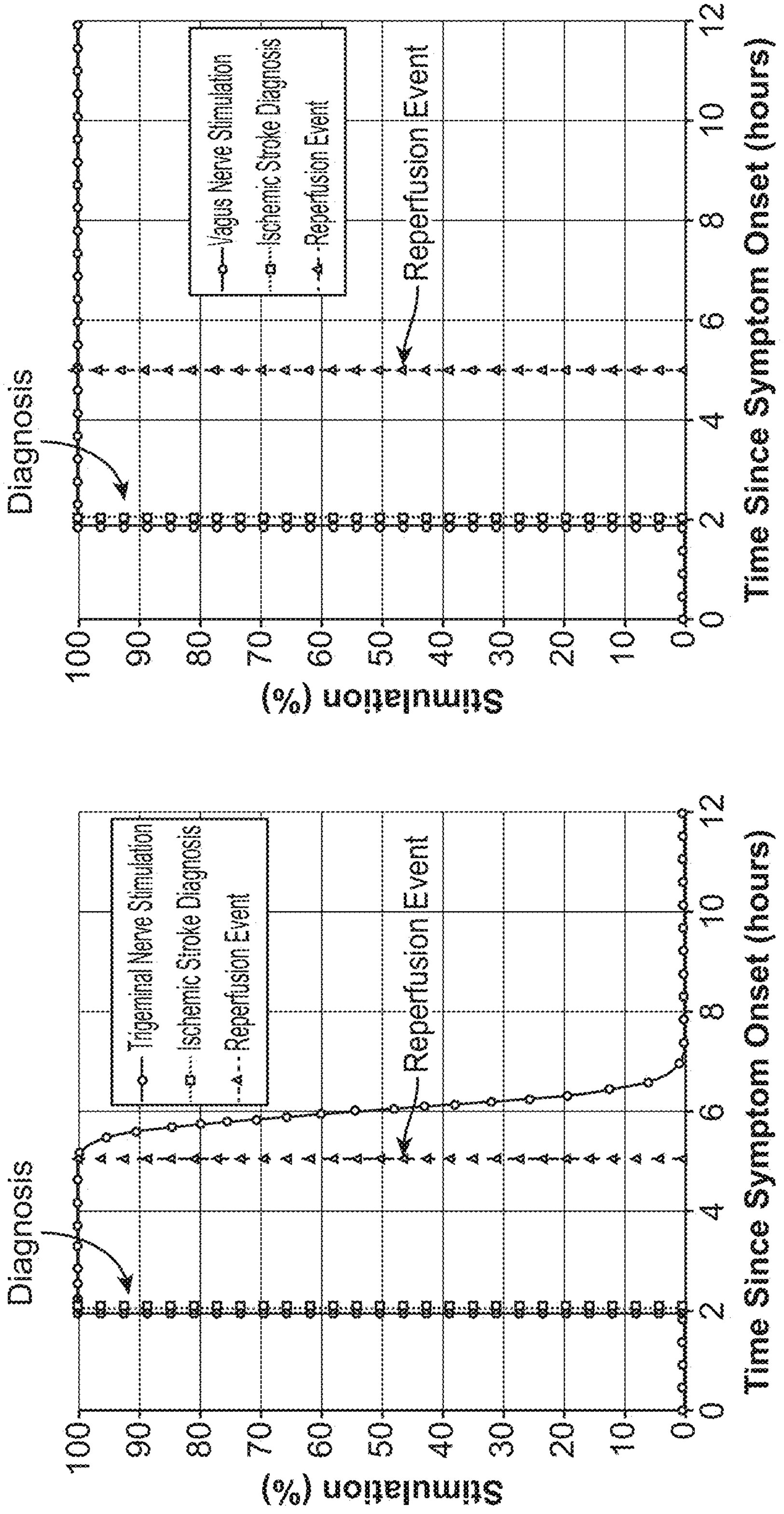
FIG. 10C provides another exemplary depiction of a coordinated stimulation of two target nerves according to an embodiment described herein.

Alternatively, in some cases, any change in stimulation may be restricted to one or more nerve branches while other nerve branch stimulation remains constant throughout treatment as depicted in FIG. 10C. FIG. 10C provides an exemplary flow chart of a method for an embodiment for stimulating two or more target nerves in which trigeminal nerve stimulation and vagus nerve stimulation occur from the time of ischemic stroke diagnosis until the time of a reperfusion event, at which point trigeminal nerve stimulation is decreased over time and vagus nerve stimulation continues over time. In some embodiments, the stimulation of the trigeminal nerve branch occurs from at least about 0 hrs, at least about 0.5 hrs, at least about 1 hr, at least about 1.5 hr, at least about 2 hr, at least about 2.5 hr, at least about 3 hr, at least about 5 hr, at least about 10 hr after system onset. In some embodiments, the duration of the trigeminal nerve branch stimulation is from about 0.1 hr to about 10 hrs. In some embodiments, the duration of the trigeminal nerve branch stimulation is at least about 0 hrs, at least about 0.5 hrs, at least about 1 hr, at least about 1.5 hr, at least about 2 hr, at least about 2.5 hr, at least about 3 hr, at least about 5 hr, at least about 10 hr, at least about 50 hrs. In some embodiments, the duration of the vagus nerve branch stimulation is from about 0.1 hr to about 100 hrs. In some embodiments, the duration of the vagus nerve branch stimulation is at least about 0 hrs, at least about 0.5 hrs, at least about 1 hr, at least about 1.5 hr, at least about 2 hr, at least about 2.5 hr, at least about 3 hr, at least about 5 hr, at least about 10 hr, at least about 50 hrs, at least about 100 hrs.

Figure 10D:
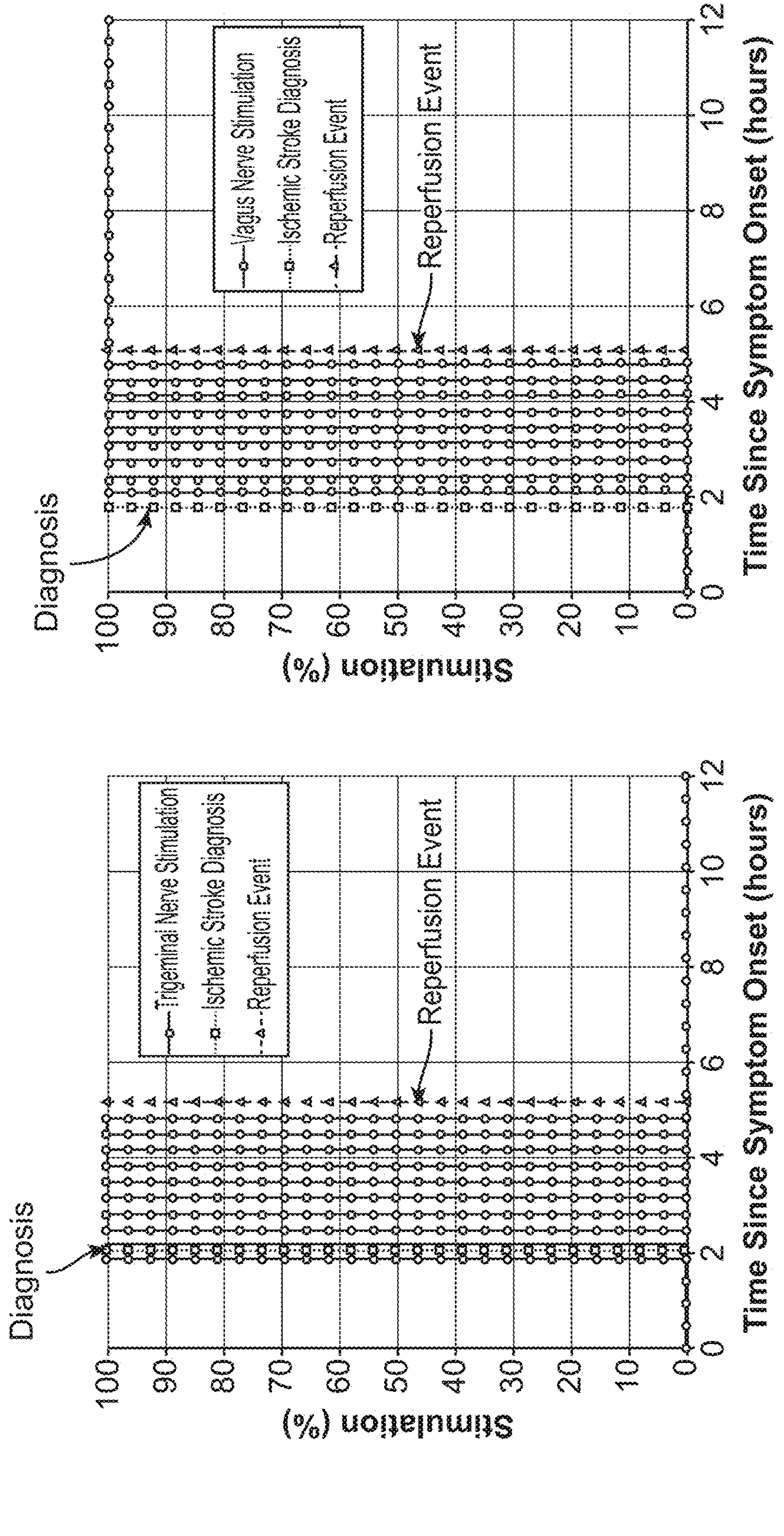
FIG. 10D provides an exemplary depiction of a coordinated stimulation of two target nerves according to an embodiment described herein.

In some cases, such as for acute ischemic stroke or traumatic brain injury, there may be a combination of responses leading to decreased oxygen available to neurons and activation of neuronal cell death mechanisms (e.g., extracellular edema, activation of apoptosis, spreading depolarization waves). In these cases, increase in cerebral blood flow through stimulation of the trigeminal nerve and protecting cells from damage through modulation of the vagus nerve may both be relevant, making simultaneous stimulation necessary. In some embodiments, one method of achieving both responses is to stimulate two or more target nerves (e.g., the trigeminal nerve and the vagus nerve) continuously and simultaneously throughout the entire treatment to induce maximum effect for both nerves. However, in some cases, stimulation of both nerve targets simultaneously may lead to unintended side effects or less efficacious results than could be achieved through stimulation of only one target nerve or the other. Therefore, alternatively, in some embodiments, there could be fluctuations between stimulation of the two or more target nerves, such as the trigeminal and the vagus nerve branches, with intermittent periods of stimulation between the two nerves that maximize individual stimulation and physiological effect for each one, as is depicted in FIG. 10D. For example, the trigeminal nerve branches and the vagus nerve branches may be stimulated in an alternating manner, with each stimulation duration for any prescribed time. In some embodiments, the duration for stimulation of each target nerve individually (in an alternating manner) is from about 1 second to about 2 hours. In some embodiments, the duration for stimulation of each target nerve individually (in an alternating manner) is at least about 0 sec, at least about 1 second, at least about 10 seconds, at least about 30 seconds, at least about 1 minute, at least about 5 minutes, at least about 10 minutes, at least about 30 minutes, at least about 45 minutes, at least about 1 hr. FIG. 10D provides an exemplary flow chart of a method for an embodiment for stimulating two or more target nerves in which trigeminal nerve stimulation and vagus nerve stimulation are intercalated from the time of ischemic stroke diagnosis until the time of a reperfusion event, at which point trigeminal nerve stimulation is ended and vagus nerve stimulation continues over time.

In some embodiments, when a patient is first triaged, a user of the device could select a predetermined type of injury or suspected injury (e.g., acute ischemic stroke, subarachnoid hemorrhage, traumatic brain injury, etc.) on the GUI, user inputs on buttons or switches, and/or through the tele-communications module. In some embodiments, additional input could include time since injury or suspected injury as previously discussed. As a result, the device would begin a stimulation profile coordinating the timing and/or intensity of stimulation at two or more different nerve branches to produce desired end effects relevant for the injury or suspected injury. In a particular use case, a user of the device may select the ischemic stroke suspected injury on the GUI and enter in a time of injury if known. This would result in the controller retrieving the appropriate stimulation profile from the programming unit. In an example embodiment, this stimulation profile could vary the intensity of trigeminal nerve branch stimulation in relation to vagus nerve branch stimulation, such that trigeminal nerve branch stimulation intensity is favored earlier in the disease course, but diminishes over time.

Exemplary Stimulation Delivery

Figure 3A:
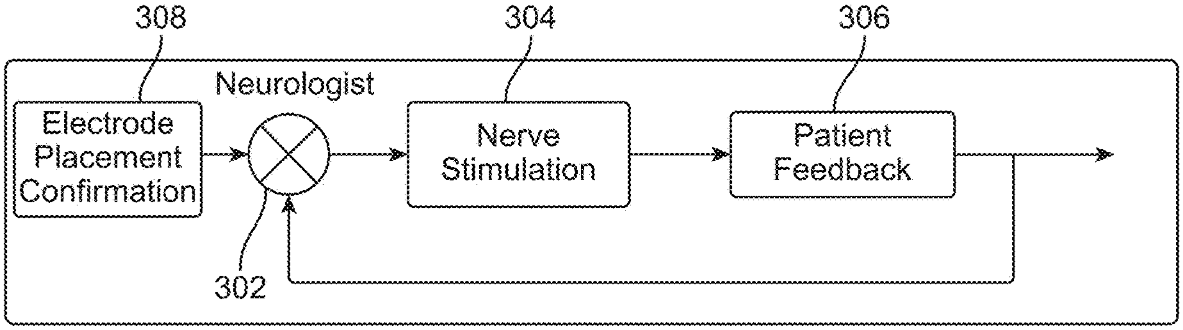
FIG. 3A provides an exemplary flow chart of a stimulation delivery scheme for an embodiment disclosed herein.

FIG. 3A provides an exemplary depiction of an exemplary scheme for specifying and/or modifying a stimulation profile for a current delivered to a set of electrodes on an ES device as described herein (e.g., FIGS. 1-2). In some embodiments the stimulation profile is specified/modified by a user (e.g., physician, clinician).

With reference to FIG. 3A, in some embodiments, the physician (e.g., neurologist) specifies and/or modifies 302 a stimulation profile delivered 304 to a patient. In some embodiments, a physiological measurement or other patient feedback 306 is communicated to the physician (e.g., neurologist), who is then able to determine whether to continue, alter, or stop simulation delivery in order to reach the desired physiological parameter or obtain a desired feedback from the patient. In some embodiments, the physiological parameter is obtained from another device, such as an oximeter measuring blood oxygenation levels. In some embodiments, the patient feedback comprises tolerability of the patient, as noted visually (for e.g., if the patient is grimacing indicating pain, the user can adjust the stimulation profile to alleviate such pain). In some embodiments, the patient feedback comprises muscle contractions, observed for example via sensors (e.g., accelerometer, gyroscope, motion detect, etc.). In some embodiments, the user also receives electrode placement confirmation (status) 308, as described herein, which is also factored with the physician's decision whether to continue, alter, or stop simulation in order to reach the desired physiological parameter. In some embodiments, the depiction in FIG. 3A is for one set of electrode or more than one set of electrodes.

Figure 3B:
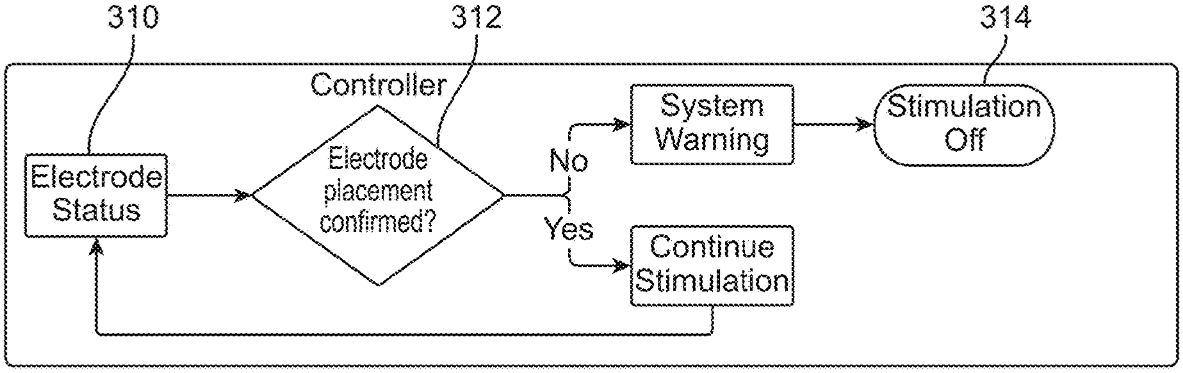
FIG. 3B provides an exemplary flow chart of an electrode placement status scheme for an embodiment disclosed herein.

FIG. 3B depicts an exemplary method for a system or device herein that automatically verifies the electrode placement status 310 by the ES device for one or more electrodes, as described herein, and automatically starts, stops, or resumes delivery of a stimulation based on the electrode status. In some embodiments, a controller 312 of the ES device receives information about the electrode status. As described herein, in some embodiments, information about the electrode status comprises an impedance measurement between at least two electrodes of a set of electrodes, the temperature of the electrodes, and/or whether the electrode is in a non-contact position. In some embodiments, based on the information about the electrode status 310, the controller 312 will 1) allow for a stimulation profile to continue to be delivered and/or the controller 312 will enable commencement of a stimulation profile to be delivered, or 2) provide a system warning and stop the stimulation profile 314 from being delivered. In some embodiments, the system warning will be displayed on the interface for the user (e.g., GUI) and/or on an ES device housing itself.

Exemplary Stimulation Delivery with Telemedicine

FIG. 4 depicts an exemplary method for a telemedicine delivery process 400. In some embodiments, an ES device (as described herein) is placed on a patient 402. In some embodiments, a physiological monitor (e.g., as part of an ES device described herein or separate from the ES device) then reads a physiological status from the patient. As described herein, in some embodiments, the physiological status comprises one or more physiological parameters relating to the patient, such as cerebral blood flow (CBF), infarct core size, heart rate, etc. In some embodiments, the device transmits to the physician 406 the physiological parameters and/or information relating to a stimulation profile being delivered or to be delivered to the patient. In some embodiments, the physician, upon receiving the physiological parameters, stimulation profile information, and/or determines whether the stimulation profile delivered to the patient should be started, stopped, or modified 412, 414. In some embodiments, where the stimulation profile delivery is started or continued, the process continues to measure the physiological status of the patient and provides updates to the physician.

Figure 5A:
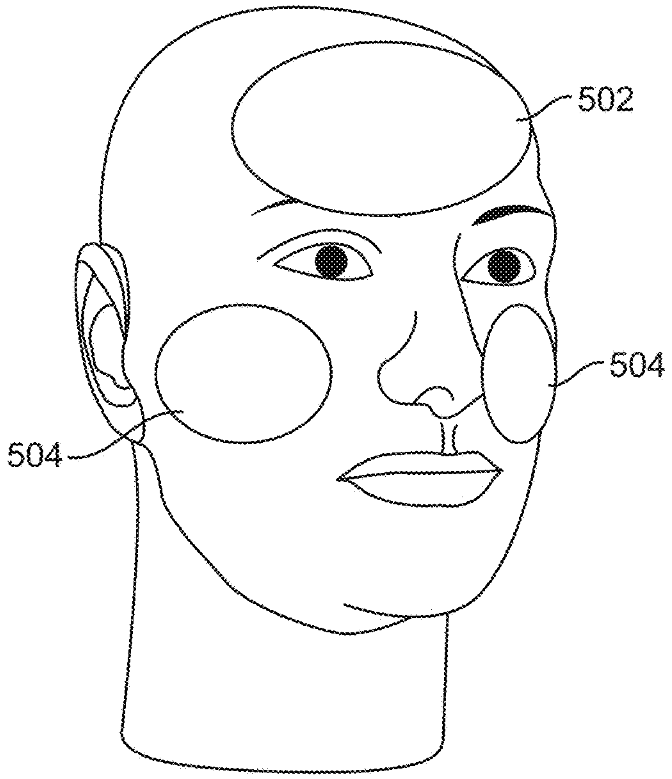
FIGS. 5A-5B provide a depiction of exemplary locations (sites) on a patient that target a corresponding target nerve.
Figure 5B:
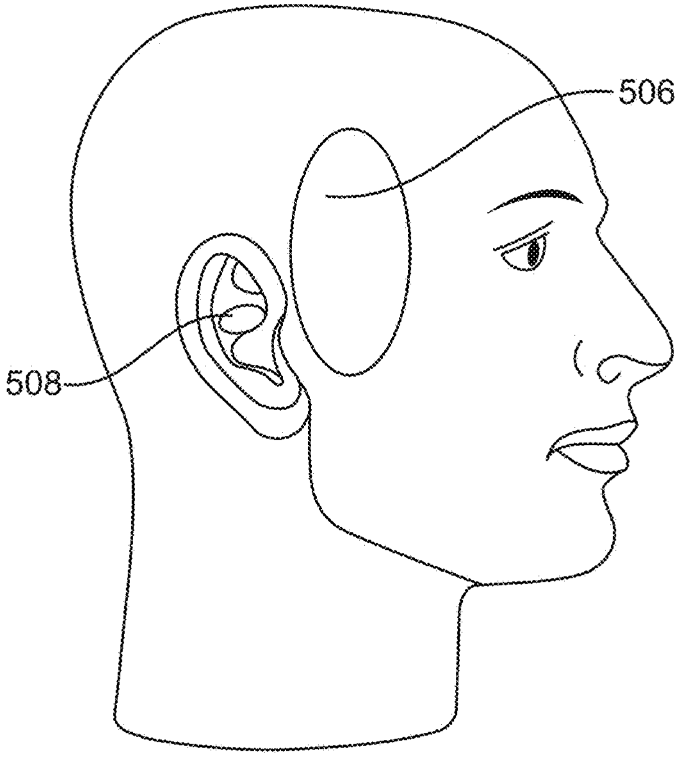

FIGS. 5A-5B depict exemplary locations as to where a stimulation can be delivered to a patient by an ES device as described herein. In some embodiments, the locations refer to locations for one or more electrodes as part of an ES device described herein. In some embodiments, the locations for electrode placement target branches of the trigeminal nerve, such as the supratrochlear, supraorbital, infraorbital, anterior ethmoid branch, and auriculotemporal branches. In some embodiments, the locations for electrode placement target branches of the vagus nerve, such as the auricular branch. For example, reference character 502 depicts an exemplary electrode placement region for stimulation of supraorbital and/or supratrochlear nerves. Reference character 504 depicts an exemplary electrode placement region for stimulation of infraorbital, superior alveolar, buccal, maxillary, mandibular, buccal and/or mental nerve. Reference character 506 depicts an exemplary electrode placement region for stimulation of auriculotemporal nerve. Reference character 508 depicts an exemplary electrode placement region for stimulation of auricular branch of the vagus nerve.

ES Device Housing

In some embodiments, any ES device described herein (e.g., from FIG. 1, FIG. 2) comprises an ES device housing to support the corresponding components (as described herein, e.g., FIGS. 1-2). In some embodiments, the ES device housing comprising a unitary structure to support all the corresponding components. In some embodiments, the ES device housing comprises an assembly comprising two or more structures to support all the corresponding components. For example, in some embodiments, the ES device 200 from FIG. 2 comprises at least one structure for supporting the SM component 201, and at least one housing to support the programming component 203. In some embodiments, an ES device housing comprises a first structure supporting one or more sets of electrodes, and a second structure supporting one or more different sets of electrodes. In some embodiments, the first structure is configured to be positioned against a first portion of patient (e.g., the front facial portion), while the second structure is configured to be positioned against a second portion of the patient (e.g., the ears, rear portion of head, torso, etc.). FIG. 7, as described herein, provides an exemplary ES device housing 700 comprising an electrode housing 704 supporting upper 708 and lower 710 sets of electrodes, and an ear clip supporting electrodes 724, 726.

In some embodiments, as described herein, the ES device housing or at least one structure of a ES device (that has multiple structures as described herein) is wearable. In some embodiments, as described herein, the ES device housing comprises goggles, a hat, a visor, a face mask, or other wearable device. In some embodiments, for any ES device described herein, the ES device housing comprises means for securing the ES device to a patient. In some embodiments, the means comprises a strap, elastic strap, a band, an elastic band, a belt, a string, or other fastening means. In some embodiments, any such means for securing the ES device to the patient is adjustable to help secure the fit of the ES device to the patient, such as tightening or loosing. For example, in some embodiments, the strap or band comprises a buckle or other fastening means (e.g., Velcro®).

In some embodiments the ES device housing comprises one or more electrode housings for supporting one or more sets of electrodes.

In some embodiments, the ES device is configured to enable stimulation at a single site (on a patient) for a single target nerve, at multiple sites targeting different branches of the same target nerve, at a single site targeting multiple target nerves, and/or at multiple sites targeting different target nerves. In some embodiments, the ES device is configured to deliver different stimulation protocols (stimulation profile) at each site. In one example, this could result in 2.5 mA of current being delivered to a stimulation site (corresponding to a set of electrodes) targeting the supraorbital nerve, while 0.5 mA of current is delivered to a site targeting the auricular branch of the vagus nerve. In some embodiments, as described herein, the stimulation parameters can differ across multiple sites receiving stimulation (i.e. multiple sets of electrodes receiving current). For example, stimulation parameters could differ on the pulse width, the current delivered to a patient, the duty cycle, among other parameters.

As described herein, in some embodiments, the delivery of the stimulation at multiple sites can be done in parallel, in series, or in any other coordinated temporal manner. In some embodiments, the timing of stimulation at multiple sites will be determined to maximize the effects, minimize adverse events, and/or other desired combination of effects. In some embodiments, such effects and/or events are determined based on feedback measurements, such patient tolerability, and/or physiological parameters measured by corresponding physiological monitors (e.g., oximeter, mechanoreceptors, others as described herein). In some embodiments, the coordination of timing stimulating two or more target nerves is predetermined or determined at the start of stimulation. In some embodiments, the coordination of stimulation will be done to maximize the innervation at the nucleus tractus solitarius (NTS) sensory nuclei in the brainstem, spinal trigeminal nucleus, the superior salivatory nucleus, and/or the rostral ventromedial medulla. Different nerves or nerve branches have different conduction lengths. Since multiple nerves lead to synapses at the NTS, stimulation of these nerves may be coordinated to optimize the signal reaching the NTS within an ideal temporal window.

Figure 6A:
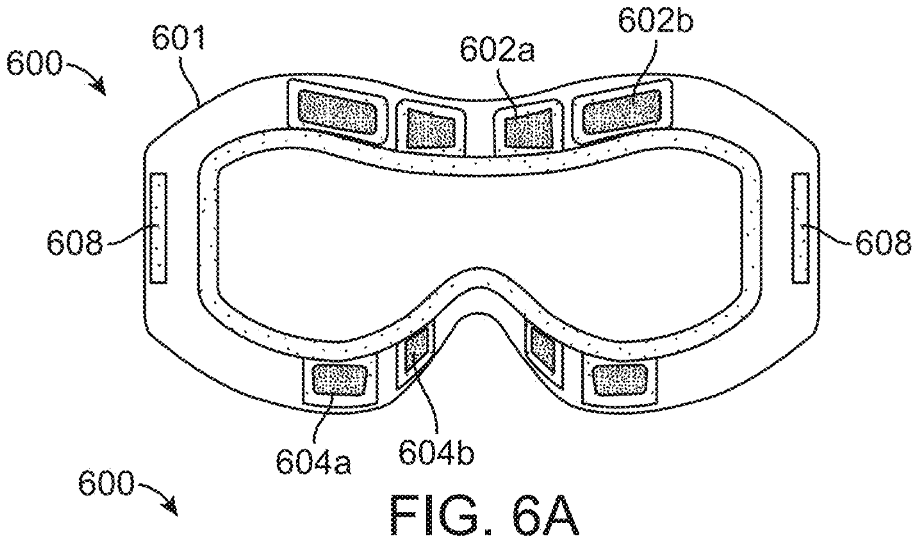
FIG. 6A provides an exemplary front view depiction of a stimulation device housing for an embodiment of a stimulation device disclosed herein.
Figure 6B:
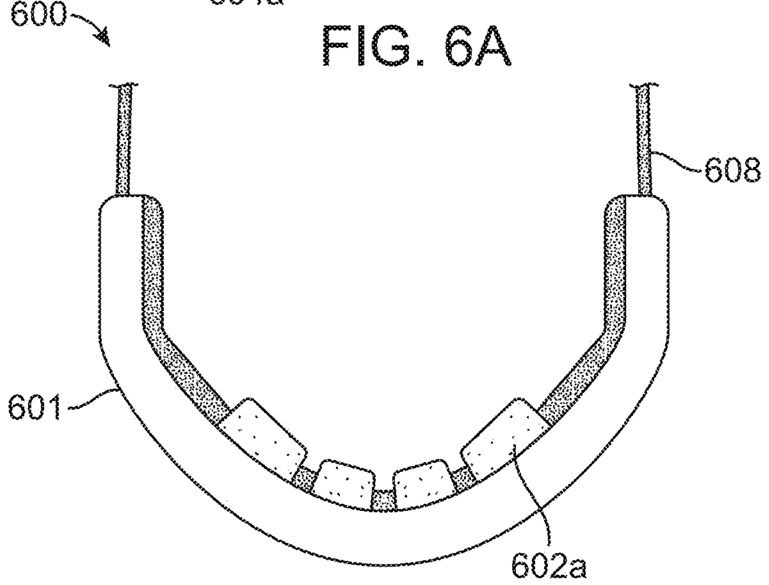
FIG. 6B provides a top view for the stimulation device housing from FIG. 6A.
Figure 6C:
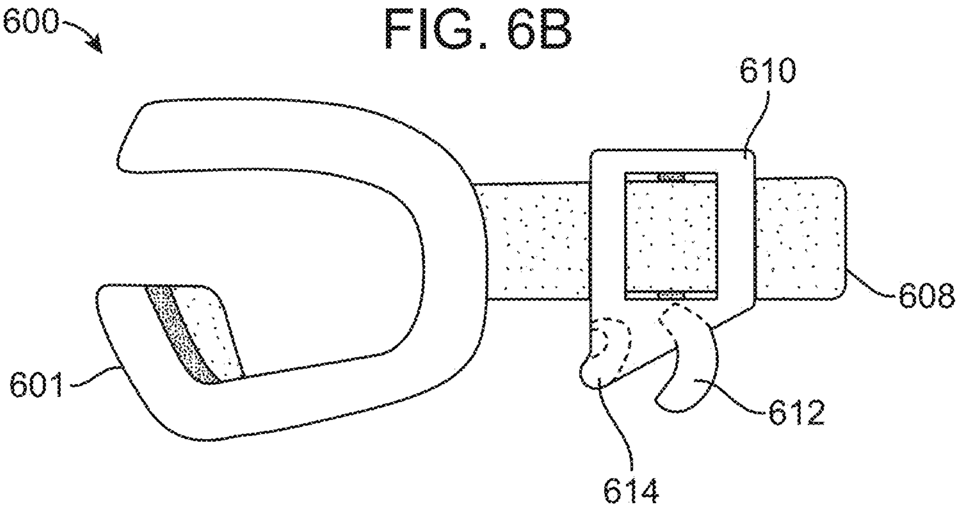
FIG. 6C provides a side view of the stimulation device housing from FIG. 6A FIG. 7A provides a rear perspective view depiction of a stimulation device housing for an embodiment of a stimulation device disclosed herein.

FIGS. 6A-6C depict an exemplary embodiment of an ES device housing for nerve stimulation described herein. FIG. 6A depicts a front view of an interior surface of the device (i.e., the surface that contacts the patient), FIG. 6B depicts a top view of the device, and FIG. 6C depicts a side view of the device. In some embodiments, the device in FIGS. 6A-6C correspond to the ES device described in FIG. 1 and/or FIG. 2. With continue reference to FIGS. 6A-6C, the depicted device is configured to simultaneously stimulate the supraorbital, infraorbital, anterior ethmoid, and/or auriculotemporal branches of the trigeminal nerve, and/or the auricular branch of the vagus nerve, on one or both sides of the patient. In some embodiments, the device comprises a housing 601 that has one or more electrodes 602, 604, 606 disposed at various location on the patient facing surface of the device. As depicted in FIG. 6A, electrodes 602*a-b* and 604*a-b* each comprise a set of electrodes, with one of each set being an anode, and the other being a cathode. In some embodiments, electrodes are provided on both sides of the device to target branches on both sides of a patient for a target nerve (for example, set of electrodes 602 are configured to target stimulation for branches on both sides of a patient face for the supraorbital and supratrochlear nerves).

In some embodiments, the other system/device components, as described herein, are disposed within the electrode housing 601. In some embodiments, the controller, device memory, device status monitor, tele-communications module, power source, and/or interface are disposed within the electrode housing 601. In some embodiments, certain components are provided on a separate housing (e.g., see SM component 201 and programming component 203 in FIG. 2). In some embodiments, one or more physiological monitors, as described herein, are also provided with the ES device 600. In some embodiments, said one or more physiological monitors are provided on a separate housing.

In some embodiments, the housing 601 further allows for the electrode 602, 604, 606 position to be translated into and out of the housing and/or within the housing, as the electrodes contact the patient's skin to ensure electrode contact with the skin. For example, in some embodiments, the electrodes are spring loaded such that translation into and out of the housing (including within the housing) allows for electrode contact with the skin for multiple electrodes. In some embodiments, the electrodes are each individually translatable with respect to the housing and biased (through for example springs) in such a way that they are fully translated out with respect to the housing and translate into the housing (against the force of the spring) upon contact with the patient's skin. This configuration would allow for electrode contact to occur in various face types if the housing were rigid. In some embodiments, the housing 601 is secured around the patients head with an elastic band 608 as shown. FIG. 6A depict the elastic band 608 coupled to either side of the device 600. In some embodiments, a strap or other material is used instead of the elastic band. In some embodiments, a power supply and tele-communications unit (which may include communicative features such as Bluetooth, Wi-Fi receiver), are provided with the device 600. In some embodiments, the power supply and the tele-communications unit are provided in a separate housing that is in operative connection with the electrode housings 612,614 (see FIG. 6C) and the front electrode housing (e.g., 601).

In some embodiments, the device 600 leaves the patient's eyes exposed without a lens so that a physician (e.g., neurologist) is able to visualize the patient's eyes and shine a light without reflection.

FIG. 6C depicts a side view of the device. In some embodiments, the elastic band 608 is placed circumferentially around the patient's head and allows for adjustment for comfort and to ensure electrode contacts of the front electrode housing 601. In some embodiments, a latch/buckle 610 is provided on each side of the device 600 that is configured to enable the elastic band on the device 600 to be secured to a user's head. In some embodiments, the latch/buckle comprises an electrode indicated by reference character 612 configured to contact the skin on the back of the patient's ear opposed to the electrode indicated by reference character 614. In some embodiments, the electrode indicated by reference character 614 contacts the skin of the cymba concha region of the patient's ear that is innervated by the auricular branch of the vagus nerve. In some embodiments, the electrodes 612,614 are in electrical communication with the electrode housing 601.

Figure 7A:
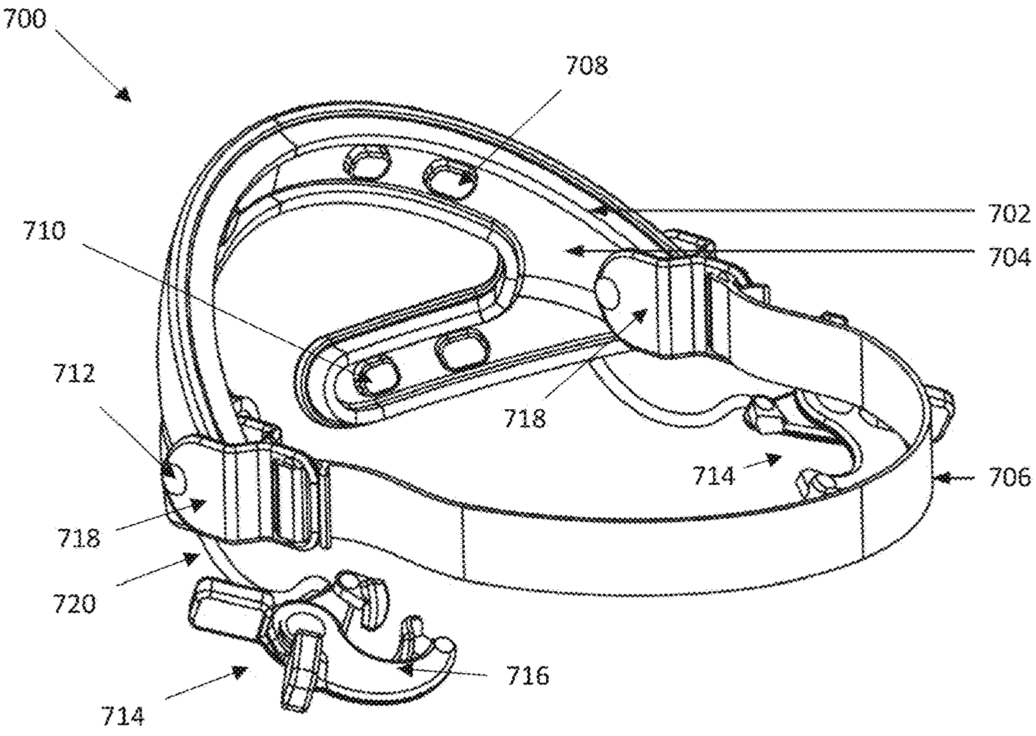
FIG. 7B provides a front perspective view depiction of the stimulation device housing from FIG. 7A.
FIG. 7C provides a side view depiction of the stimulation device housing from FIG. 7A.
FIG. 7D provides a top view depiction of the stimulation device housing from FIG. 7A.
FIG. 7E provides a front view depiction of the patient facing surface of the electrode housing from the stimulation device housing from FIG. 7A.
FIG. 7F provides a perspective view depiction of the ear clip from the stimulation device housing from FIG. 7A.
Figure 7B:
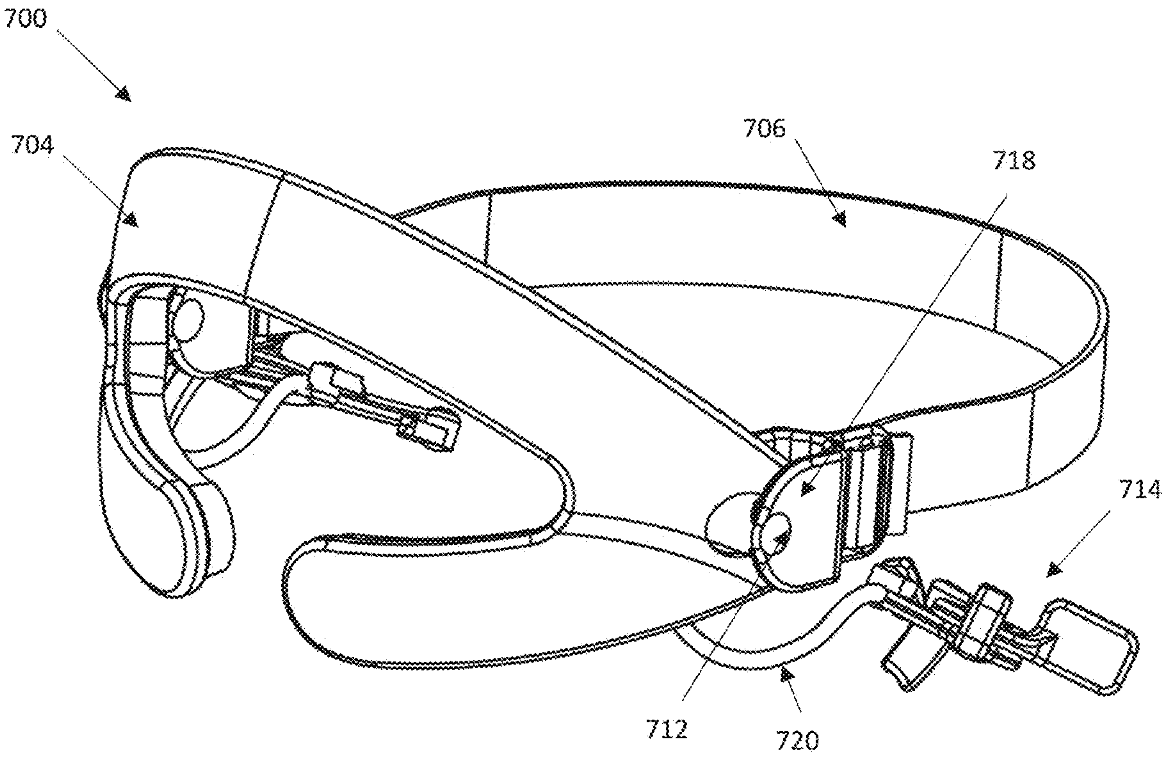
Figure 7C:
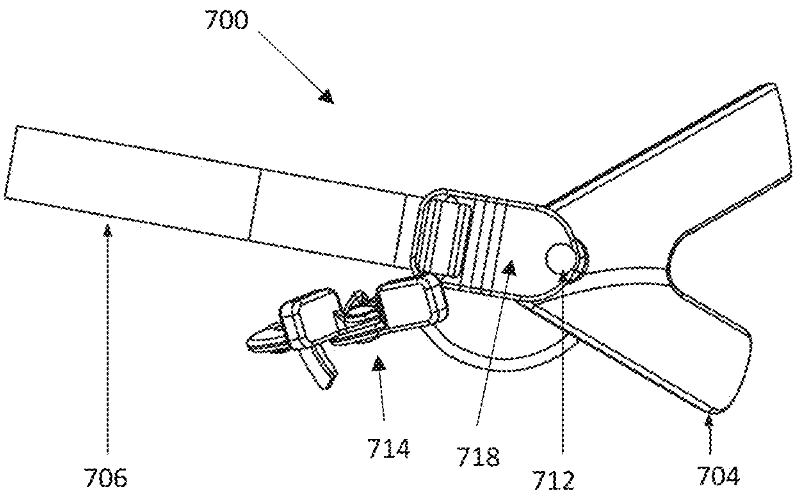
Figure 7D:
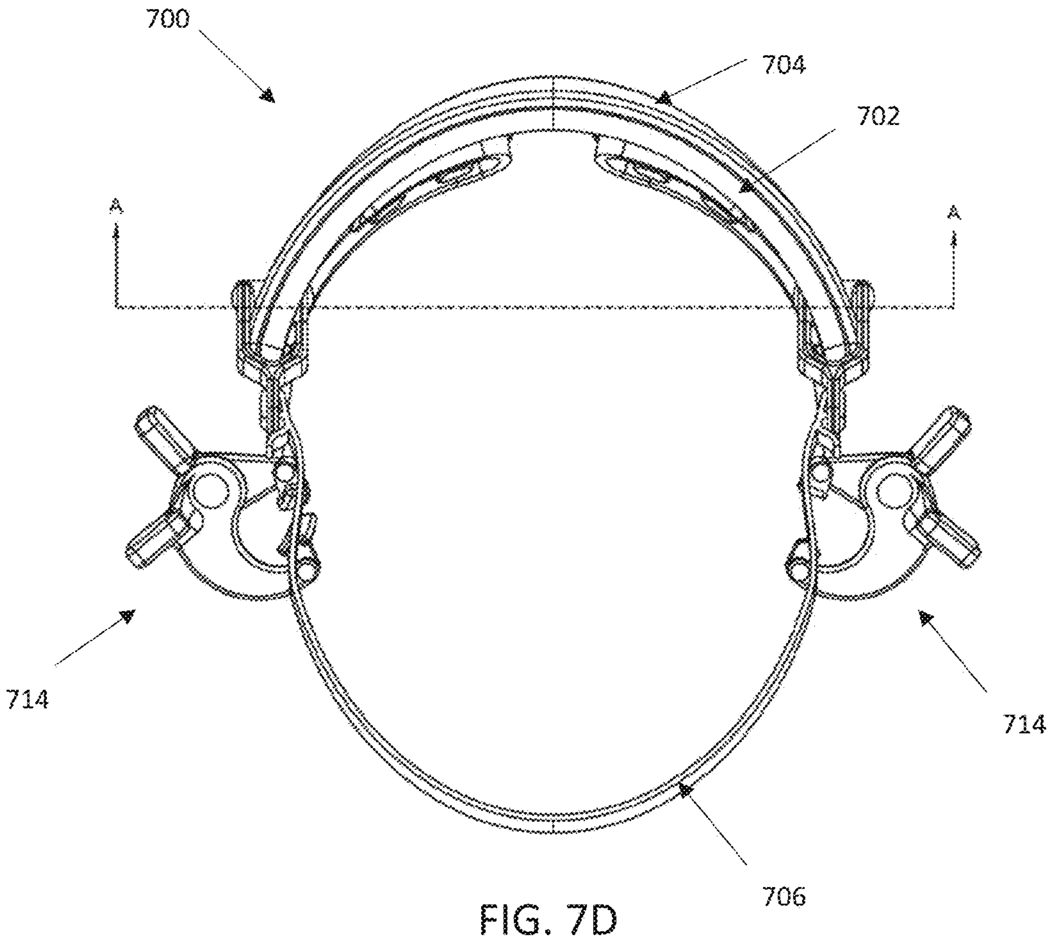

FIGS. 7A-7F depict another exemplary embodiment of an ES device 700 for stimulating one or more target nerves, as described herein. In some embodiments, the ES device is wearable about a patient. FIGS. 7A-7B provide a rear and front perspective view, respectively, of the ES device 700, while FIGS. 7C-7D provides a side and top view, respectively, of the ES device 700. In some embodiments, the ES device 700 comprises a housing having comprising an electrode housing 704, a strap 706, a coupling 718 that couples the strap 706 with the electrode housing 704. In some embodiments, the ES device 700 further comprises an ear clip 714 that is coupled to and in communication with the electrode housing 704 via a wired connection 712. In some embodiments, the ear clip 714 is separated from the electrode housing and in communication with said electrode housing via a wireless connection (e.g., Bluetooth, Wi-Fi, etc.). In some embodiments, the other system/device components, as described herein, are disposed within the electrode housing 704. In some embodiments, the controller, device memory, device status monitor, tele-communications module, power source, and/or interface are disposed within the electrode housing 704. In some embodiments, certain components are provided on a separate housing (e.g., see SM component 201 and programming component 203 in FIG. 2). In some embodiments, one or more physiological monitors, as described herein, are also provided with the ES device 700. In some embodiments, said one or more physiological monitors are provided on a separate housing.

With continued reference to FIGS. 7A-7D, the electrode housing 704 comprises one or more electrodes (e.g., 708, 710) on a patient facing surface of the electrode housing. In some embodiments, the electrodes are provided as sets of electrodes, with each set of electrode comprising a cathode electrode and an anode electrode. In some embodiments, the electrodes (e.g., 708, 710) are spaced along the patient facing surface of the electrode housing 704 so as to target stimulation of one or more target nerves. For example, the upper electrodes 708 are located so as to contact a portion of a patient's face that is proximate to the supratrochlear branch of the trigeminal nerve, while the lower electrodes 710 are located so as to contact a portion of the patient's face that is proximate to the infraorbital nerve. In some embodiments, the housing 704 further allows for the electrode (e.g., 708, 710) position to be translated into and out of the housing and/or within the housing, as the electrodes contact the patient's skin to ensure electrode contact with the skin. For example, in some embodiments, the electrodes are spring loaded such that translation into and out of the housing (including within the housing) allows for electrode contact with the skin for multiple electrodes. In some embodiments, the electrodes are each individually translatable with respect to the housing and biased (through for example springs) in such a way that they are fully translated out with respect to the housing and translate into the housing (against the force of the spring) upon contact with the patient's skin. This configuration would allow for electrode contact to occur in various face types if the housing were rigid.

In some embodiments, and as described herein, the ear clip 714 comprises one or more sets of electrodes to be positioned against a patient, so as to target one or more target nerves, such as auricular branch of the vagus nerve. Accordingly, the ES device 700 is configured to stimulate a plurality of target nerves.

In some embodiments, the strap 706 comprises an elastic strap, an elastic band, or other stretchable material that enables the strap to securely wrap around a patient's head, and thereby enabling a secure and sufficient contact of the electrode housing (and thereby electrodes) and a patient's face. In some embodiments, a foam layer 702 is disposed along the interior surface of the electrode housing 704. In some embodiments, the electrode housing 704 is flexible, and configured to conform with a wide variety of patient face shapes and/or head shapes. As depicted in FIGS. 7A-7D, the ES device comprises a coupling 718 on either side of the electrode housing 704. In some embodiments, each coupling 718 comprises a buckle, thereby enabling the tightness of the strap 706 about the patient's head to be adjusted. In some embodiments, each coupling 718 defines a pivot point 712 that enables the electrode housing 704 to be rotated with respect to the strap 706. In some embodiments, each pivot point is coaxial with each other. In some embodiments, the pivot point 12 of the electrode housing 704 is positioned vertically between the upper (e.g., 708) and lower (e.g., 710) sets of electrodes. In some embodiments, such positioning of the upper and lower sets of electrodes enables the electrode housing 704 to be able to rotate to ensure both the upper and lower electrodes remain in contact with the patient's skin. In some embodiments, if either set of electrodes (upper and/or lower) are not in contact with the patient's skin, a moment is generated about the contacting electrode point with the lever arm (e.g., coupling 718) being the normal distance to the elastic band and the force being generated by the strap 706. Because this moment is not counteracted, the non-contacting electrode set will be forced into contact with the patient's skin.

Figure 7E:
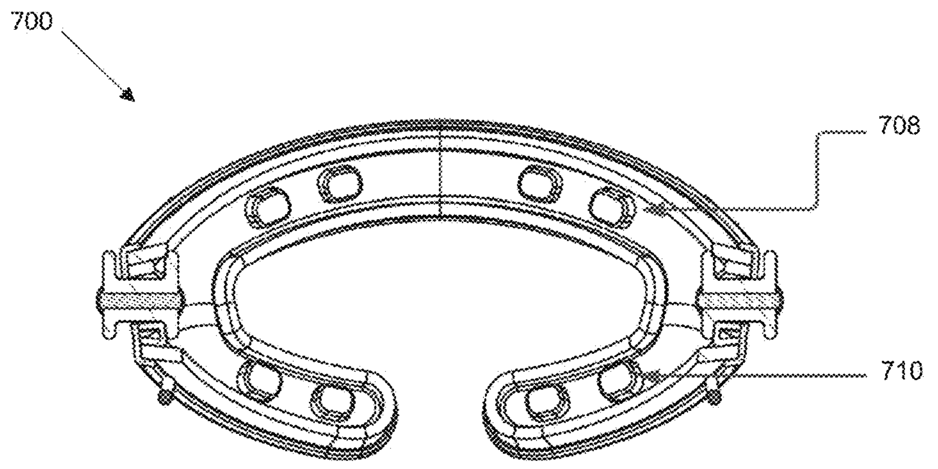

FIG. 7E depicts the patient facing surface of the electrode housing 704, comprising the upper electrodes (708) and the lower electrodes (710). As described herein, in some embodiments, the electrodes are provided as sets of electrodes, wherein either one of the electrodes (for each set of electrodes) can be the anode or cathode. In some embodiments, the anode and cathode of each set of electrode is configured to be modified during stimulation delivery. As depicted in FIG. 7E, the sets of the upper electrodes and the lower electrodes are provided on both sides of the ES device 700 so as to reach both the left and right sets of the respective target nerve branches (as described herein).

Figure 7F:
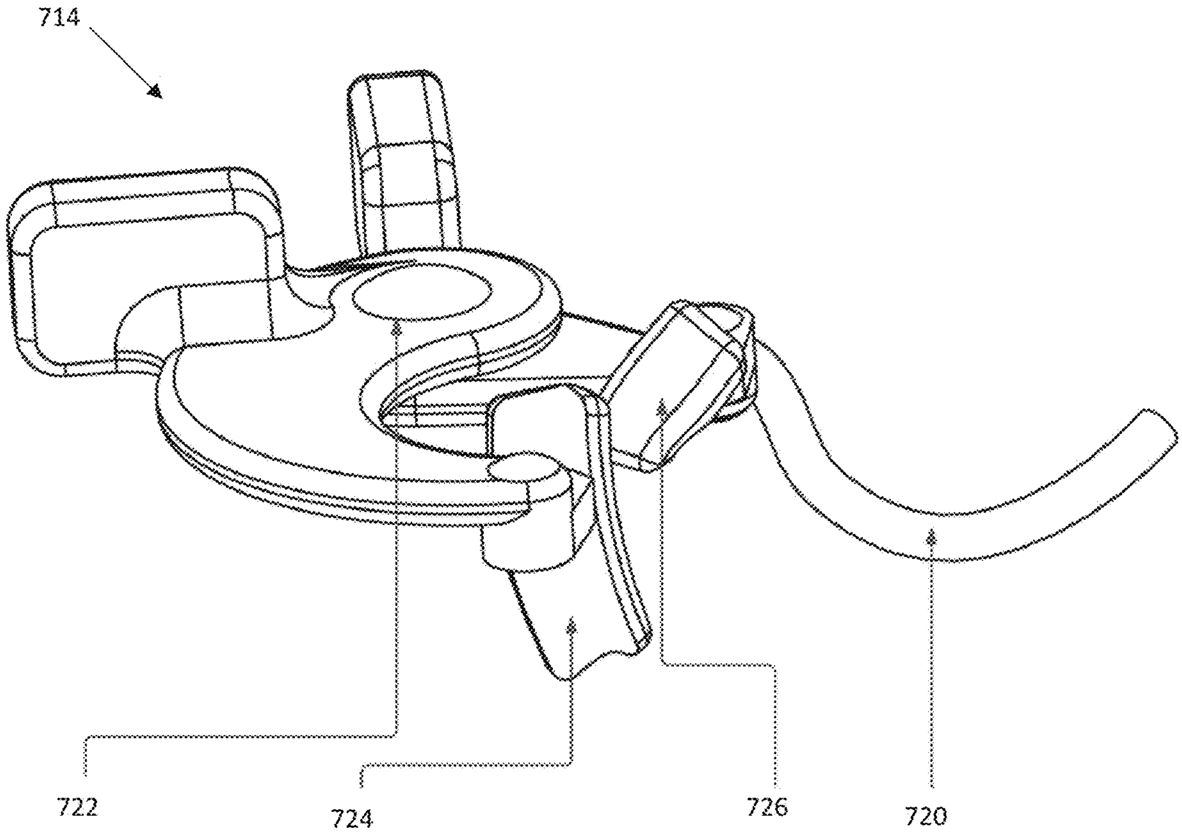

FIG. 7F depicts an exemplary illustration of the ear clip 714 of the ES device 700. In some embodiments, the ear clip 714 is configured to stimulate the auricular branch of the vagus nerve transcutaneously. In some embodiments, the ear clip 714 is spring-loaded and pivots about the joint indicated by reference character 722 such that electrodes (on the ear clip 714) are biased to be in contact or close to in contact with each other when not placed on the patient. In some embodiments, the electrode indicated by reference character 724 contacts the skin on the back of the patient's ear opposed to the electrode indicated by reference character 726. In some embodiments, the electrode indicated by reference character 726 contacts the skin of the cymba concha region of the patient's ear that is innervated by the auricular branch of the vagus nerve. As described herein, in some embodiments, the ear clip 714 is in electrical communication with the electrode housing (not shown) through a wired connection 720 and/or a wireless connection.

Figure 8A:
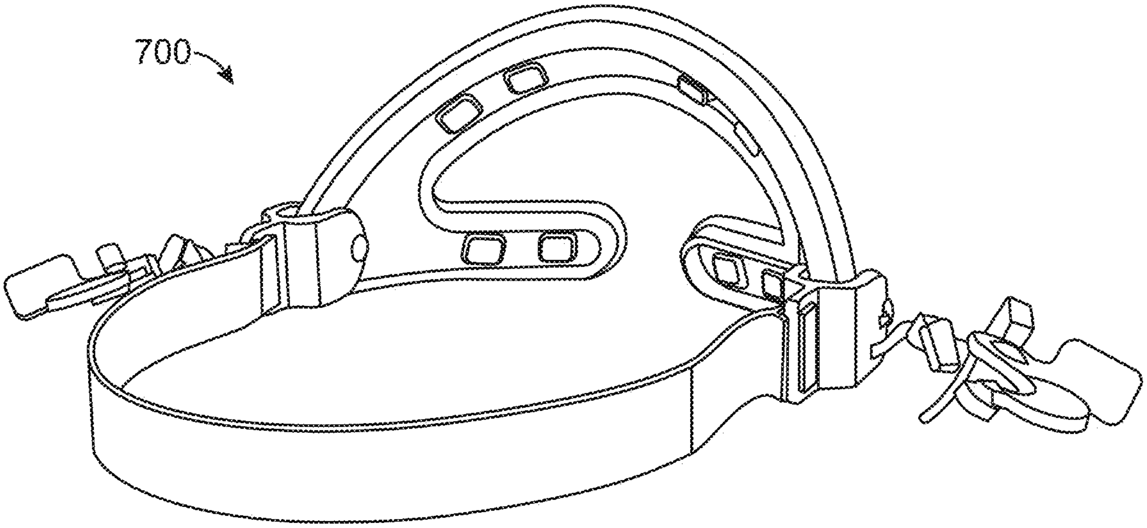
FIG. 8A provides a rear perspective view of an image of the stimulation device housing from FIG. 7A.
Figure 8B:
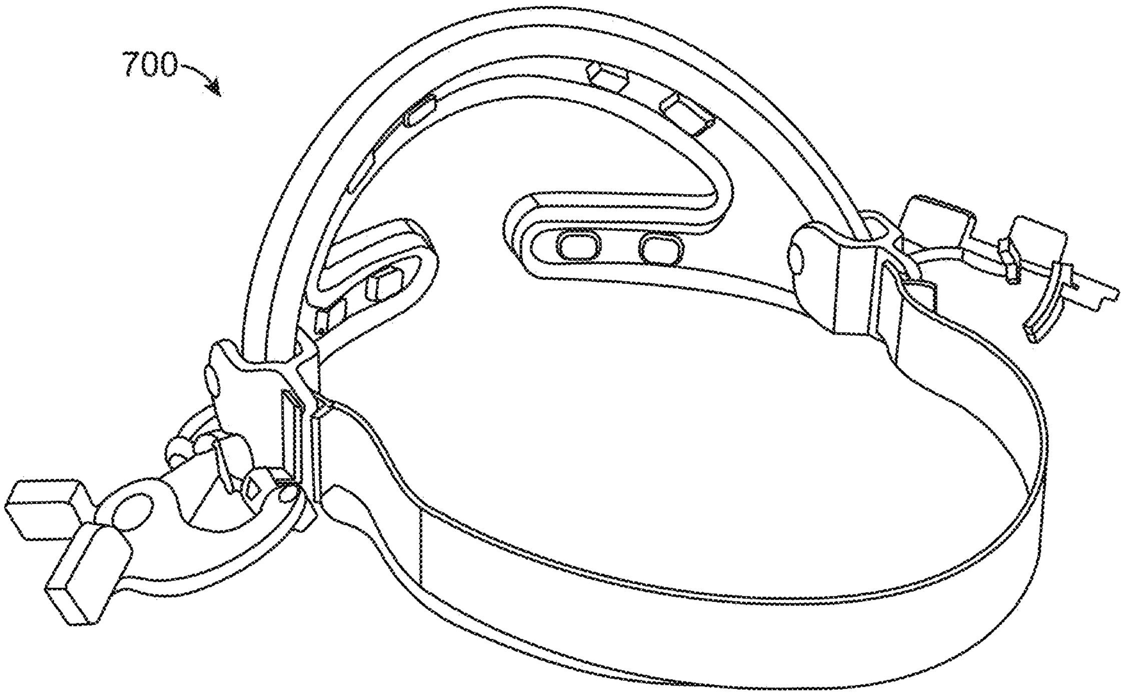
FIG. 8B provides another rear perspective view of an image of the stimulation device housing from FIG. 7A.
Figure 8C:
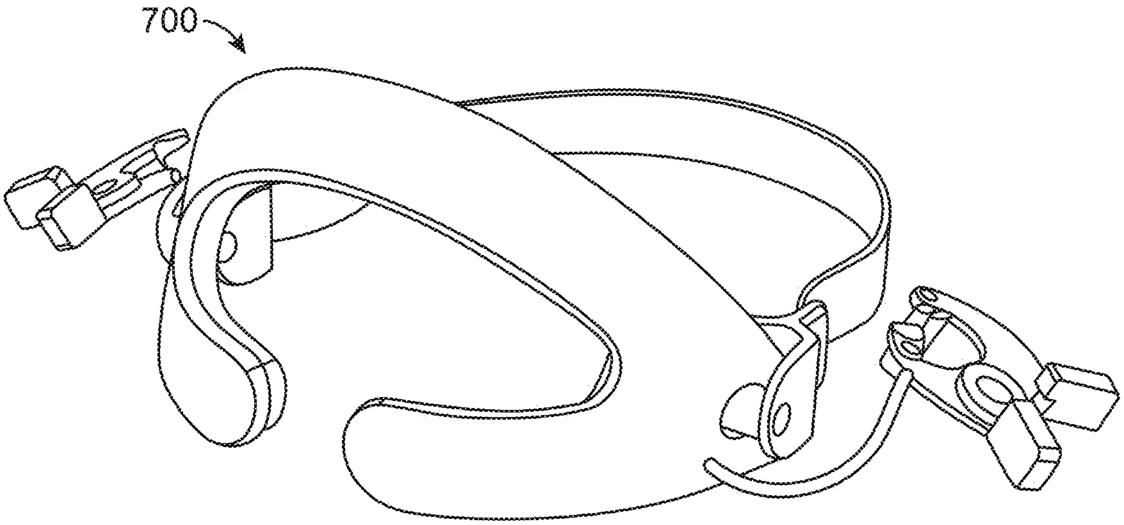
FIG. 8C provides a front perspective view of an image of the stimulation device housing from FIG. 7A.

FIGS. 8A-8C depict exemplary images of the ES Device 700, specifically depicting a rear perspective view, another rear perspective view, and a front perspective view respectively.

Method

Figure 9:
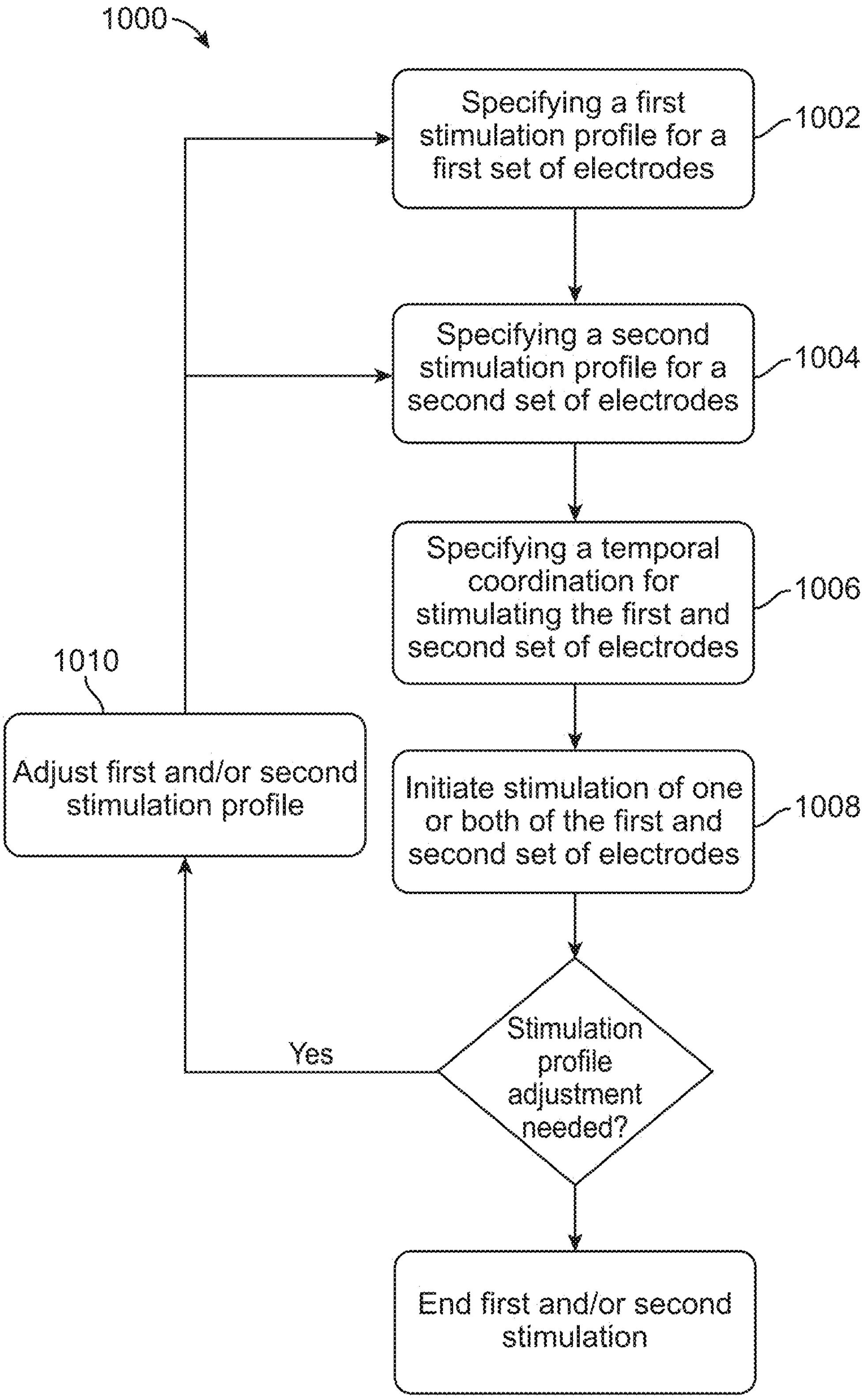
FIG. 9 provides an exemplary flow chart of a method for an embodiment for stimulating two or more target nerves, as disclosed herein.

FIG. 9 depicts an exemplary method for stimulating two or more target nerves, as described herein. In some embodiments, the method comprises using any ES device as described herein. In some embodiments, the ES device comprises one or more sets of electrodes configured to target the two or more target nerves. The exemplary method in FIG. 10 is based a first set of electrodes targeting a first target nerve, and a second set of electrodes targeting a second nerve. As described herein, in some embodiments, the first set of electrodes is placed at a first site on the patient, corresponding to the first target nerve, while the second set of electrodes is placed at a second site on the patient, corresponding to the second target nerve. In some embodiments, as described herein, stimulation of a target nerve occurs at a single site for a single target nerve, at multiple sites targeting different branches of the same target nerve, at a single site targeting multiple target nerves, and/or at multiple sites targeting different target nerves.

With reference to FIG. 9, in some embodiments, a user (e.g., physician, clinician, medical staff, caregiver, etc.) will specify a first stimulation profile 1002 for a stimulation to be delivered to a first target nerve. In some embodiments, the first stimulation profile comprises corresponding stimulation parameters corresponding to a current to be delivered to a first set of electrodes, which are located at a site on the patient that corresponds with the first target nerve (as described herein). The corresponding stimulation parameters for the first stimulation profile can comprise any combination of parameters and specification as described herein. In some embodiments, a user (e.g., physician, clinician, medical staff, caregiver, etc.) will specify a second stimulation profile 1004 for a stimulation to be delivered to a second target nerve. In some embodiments, the second stimulation profile comprises corresponding stimulation parameters corresponding to a current to be delivered to a second set of electrodes, which are located at a site on the patient that corresponds with the second target nerve (as described herein). The corresponding stimulation parameters for the second stimulation profile can comprise any combination of parameters and specification as described herein.

In some embodiments, the first and/or second stimulation profiles are specified via an interface for the ES device, as described herein. In some embodiments, the first and/or second stimulation profiles are selected from pre-existing stimulation profiles stored on a memory on the ES device. In some embodiments, the first and/or second stimulation profiles are specified based on past patient information (e.g., patient tolerability to receiving stimulation, health conditions, or other feedback previously received).

In some embodiments, the first and/or second stimulation profile is configured to deliver the same stimulation profile with the same corresponding stimulation parameters for the duration of the stimulation delivery. In some embodiments, the first and/or second stimulation profiles are configured to randomize the corresponding stimulation parameters (i.e. vary the stimulation parameters) for at least a portion of the stimulation delivery (to the respective target nerve). Randomizing the stimulation parameters may help maintain a target nerve stimulation, and may help avoid habituation by the target nerve (for example, akin to a shirt on a person's back that does not realize it is on after some time). In some embodiments, the stimulation profile for the first and/or second stimulation profile is randomized (e.g., switching from pulse profile to a sine wave profile).

In some embodiments, the first stimulation profile is the same as the second stimulation profile. In some embodiments, the first stimulation profile is different from the second stimulation profile. For example, in some embodiments, a first stimulation profile comprises 2.5 mA of current being delivered to a stimulation site targeting the supraorbital nerve (e.g., a first target nerve), while 0.5 mA of current is delivered to a site targeting the auricular branch of the vagus nerve (e.g., a second target nerve). As described herein, in some embodiments, stimulation parameters differ on the pulse width, the current delivered to a patient, the duty cycle, or other parameters.

In some embodiments, the user specifies a specific temporal coordination 1006 between the stimulation delivered to the first and second target nerves. In some embodiments, as described herein, the temporal coordination comprises stimulation being delivered to the first and second target nerves in parallel, in series, a combination thereof, or any other coordinate temporal manner (e.g., intermittent delivery of stimulation to the first and/or second target nerve that may or may not overlap for at least a portion). In some embodiments, the stimulation is delivered to either the first or second target nerve continuously, while the other target nerve (i.e. the first or second target nerve not receiving stimulation continuously) receives stimulation at intermittent periods (while the continuous stimulation is being delivered to the other target nerve). In some embodiments, the temporal coordination between the stimulation delivered to the first and second target nerves is inherent with the specified stimulation profiles for each set of electrodes. In some embodiments, the timing of stimulation at multiple sites will be determined to maximize the effects, minimize adverse events, and/or other desired combination of effects. As described herein, such effects and/or events are determined by the device's monitoring components and/or other feedback (such as patient tolerability, monitoring from another device, e.g., a physiological monitor) as described herein. In some embodiments, the coordination of temporal stimulation delivery for the first and second target nerves is predetermined or determined at the start of stimulation. In one embodiment, the coordination of stimulation will be done to maximize the innervation at the nucleus tractus solitarius (NTS), sensory nuclei in the brainstem. Different nerves or nerve branches have different conduction lengths. Since multiple nerves lead to synapses at the NTS, stimulation of these nerves can be coordinated to optimize the signal reaching the NTS within an ideal temporal window.

In some embodiments, once the stimulation profiles and/or temporal coordination have been specified, the stimulation delivery is initiated 1008. In some embodiments, as described herein, the ES device is configured to automatically detect adequate electrode placement (e.g., via the impedance measurement between a set of electrodes). In some embodiments, the ES device is further configured to automatically prevent stimulation delivery for a target nerve from commencing if inadequate electrode placement is detected (as described herein). In some embodiments, the ES device is configured to start or re-start stimulation delivery to a target nerve once adequate electrode placement is detected (as described herein).

In some embodiments, a user will receive feedback from the patient based on the stimulation(s) being delivered. In some embodiments, the feedback comprises patient tolerability, as visually observed (such as signs that show the patient in pain, e.g., facial expression, clenched fists, etc.). In some embodiments, the feedback comprises feedback from a physiological monitor (e.g., oximeter measuring blood oxygenation level, sensor detecting muscle contraction (as described herein), etc.).

In some embodiments, the user will adjust the first and/or second stimulation profile 1010 based on the feedback received. For example, the user will adjust the first and/or second stimulation profile so as to remove the pain experienced by the patient, or improve the stimulation sensation to the first and/or second target nerve.

In some embodiments, after a prescribed duration of time has elapsed, the ES device will automatically stop the stimulation to the first and/or second target nerve. In some embodiments, the user will end the stimulation to the first and/or second target nerve after a prescribed duration of time has elapsed, or if the feedback from the patient warrants the end of the stimulation.

Exemplary Clinical Scenarios for Use of Systems, Devices, and Methods Described Herein Ischemic Stroke In some embodiments, ischemic stroke care occurs in a complex continuum funneling patients to more specialized centers based on the triage of a number of different diagnostic factors. In some embodiments, the system organization of stroke care varies by geography with variants including but not limited to hub-and-spoke, direct-to-mothership, drip-and-ship, or drip-and-drive models. These different models may be defined by the flow and timing of transfer of patients or neuro interventionalists from or to primary stroke centers (PSCs) or comprehensive stroke centers (CSCs). In some embodiments, one of the primary tenants of stroke care is speed. In some embodiments, systems, methods, and devices described herein are configured to be utilized in a number of different clinical scenarios and organizational models without interrupting current workflow.

In some embodiments, in an ischemic stroke, blockage of a blood vessel instigates a cascade of events that result in damage to neurons. Over time, different areas of interest develop at and around the site of injury. The first is the infarct core. This is an area close to the site of ischemia where the cascade has progressed the most and likely reflects unsalvageable tissue. Around this area is the penumbra, a zone that reflects tissue at risk. Over time, the infarct core progresses to take up more and more penumbra. A smaller penumbra to infarct core ratio is associated with a worse long term clinical outcome. The progression of the infarct core occurs at different rates and varies between patients. In some embodiments, systems, devices, and methods described herein are configured to slow the rate of progression to limit the amount of unsalvageable tissue. In some embodiments, such slowing the rate of progression is accomplished by different mechanisms of action, such as for example: increasing perfusion through collateral pathways, reducing or stopping spreading depolarization, reducing the inflammatory response, and/or limiting the edema produced.

New Arrival in the Emergency Department: In some embodiments, a path to care involves a patient suspected of stroke arriving at an emergency department via ambulance, walk-in, or any other form of transport. A code “stroke” is typically activated and carried out based on the emergency response structure implemented at the healthcare facility. A typical evaluation will involve an assessment by a neurologist either in person or via tele-neurology capabilities. Among the steps of evaluation are the NIH Stroke Score and a CT scan without contrast of the Head and Brain. These two diagnostics combined with any other exam, test, or component of patient history are sufficient to diagnose ischemic stroke. In some embodiments, immediately after diagnosis, systems, devices, and methods described herein are configured to applied to the patient irrespective of the treatment plan. In some embodiments, systems, devices, and methods described herein will stimulate target nerves with particular stimulation parameters. In some embodiments, a monitoring component of the system or device (as described herein) provides additional information for the user (e.g., physician, clinicians, medical staff, and/or other caregiver). In some embodiments, standard of care treatment including but not limited to transminogen platelet activator (tPA) can be administered intravenously simultaneously.

Code Stroke in Care Setting: In an alternative scenario, where a patient is already inpatient at a care facility, in some embodiments, systems, devices, and methods described herein are configured to be applied to stimulate target nerves with particular parameters after the diagnosis of ischemic stroke is made. In some embodiments, the monitoring component of the device can provide additional information for the user (e.g., clinicians, etc.). In some embodiments, standard of care treatment for the ischemic stroke or for other non-acute diagnoses can be performed simultaneously with the implementation of our device.

Transfer from PSC to CSC: In some cases, a subset of ischemic stroke patients will require transfer from a PSC to a CSC for more specialized care, including but not limited to endovascular thrombectomy (EVT). These patients may have already received tPA, are receiving tPA, or will not receive tPA. In some embodiments, systems and devices, as described herein, applied to the patient after ischemic stroke diagnosis, can be left in place on the patient during transfers in the hospital but also for longer transfers between care facilities. In some embodiments, the device housing (or assembly) containing the stimulation device (as described herein) as well as any monitoring components can be left in place about the patient’s head, and maintain sufficient stimulation signal for the intended effect. In some embodiments, at the accepting CSC, the device can remain in place, continuing any stimulation parameters while the patient is undergoing further treatment.

In another embodiment, a component of the device (as described herein), such as a programming component, as described herein (e.g., see FIG. 2, reference character 203), could be present at each care facility and/or on a transport vehicle. In some embodiments, a stimulation and monitoring component, as described herein (e.g., see FIG. 2, reference character 201) could interface with each programming unit in the separate care settings.

In some embodiments, during a transfer between hospitals, the device (as described herein) can connect with tele neurology networks to transmit patient location, physiological markers, or disease progression, among any other pertinent information, to accepting clinicians at a CSC. As systems currently exist, clinicians lack “eyes on a patient” during these transfer periods. In some embodiments, systems and devices described herein incorporate features such as GPS and accurate relay of timestamps to assist care teams at receiving facilities. In some embodiments, this information can assist in the triage and preparation of resources at the new facility. In some embodiments, this same information may be transmitted back to clinicians at PSCs enabling changes in instructions, assisting documentation, or communicating patient status, among other benefits.

In some embodiments, information on physiological markers or disease progression enable clinicians to make decisions on patient care when previously not possible. When patients are transferred, they enter a black box where the last information that is known to care teams is often the time point immediately prior to transfer. In some embodiments, the monitoring components included with the device described herein provide advanced warning necessary to quickly care for patients with worrisome disease progressions.

Mobile Stroke Transfers: Mobile stroke units (MSUs) are ambulances fitted with the capability to complete mobile imaging techniques that enable the diagnosis of ischemic stroke in the field. In these scenarios, treatment with tPA can be started prior to arrival at the appropriate care facility. In some embodiments, the systems and devices described herein are configured to be applied to the patient during this initial transit period prior to arrival at the appropriate care facility. In some embodiments, the device remains with the patient during the remainder of their clinical journey.

Last Known Well: In some embodiments, the standard of care intervention employed after ischemic stroke diagnosis is based on the time since the patient was last known to be well. This divides care into different early or late time windows. In some embodiments, systems and devices described herein are configured to be used in any acute window and does not have to be applied immediately at the time of diagnosis. For instance, in the previously described scenarios above, the device could be applied at the CSC after transfer from a PSC. In some embodiments, for optimal effect on outcome, earlier intervention with a device described herein would be ideal. In some embodiments, a device described herein is applied after starting or completing other standard of care treatments as a supplement to care.

For Patients without Definitive Treatment Options: In some embodiments, EVT or tPA are the primary treatment options for patients diagnosed with ischemic stroke, but they are only offered to patients that meet certain criteria, with time windows and the amount of salvageable tissue being key determinants. In some embodiments, for other patients, medical management is the mainstay. In some embodiments, for these patients, systems and devices described herein are configured to supplement care by working to slow infarct progression giving other medications, conservative management, and the body's own response more time to act and stabilize care. In some embodiments, additional modulation of the inflammatory response could also lead to improved outcomes in these patients.

Application in Relation to the Angiography Suite: In some embodiments, EVT requires the angiography suite where clinicians visualize the vasculature through fluoroscopy. In some embodiments, stimulation using a device described herein is configured to be applied in this setting to increase cerebral or central blood flow during a procedure. In some embodiments, this is in the form of increased flow velocity or through more localized vasodilation. In some embodiments, this change in vascular tone or flow is visualized through existing fluoroscopy technology and a physician may alter the stimulation based on the desired response. In some embodiments, use during the angio suite reduces the chance of vasospasm or treat vasospasm that occurs. In some embodiments, use during EVT also allows capture of more distal clots in smaller vessels than is currently achievable. In some embodiments, the use of a device described herein for this purpose could be for procedures other than EVT. In some embodiments, the device could then remain in place stimulating, monitoring, or both, after the patient's procedure is complete, during transfer from the angio suite, and/or after reaching the next clinical care area.

Post-Acute Treatment: In some embodiments, a device described herein is configured to monitor physiological markers and stimulate target nerves with particular parameters after acute treatment. In some embodiments, continuation of use into the post-acute phase helps modulate the inflammatory response and improve rehabilitation, among other effects.

Suspected Diagnosis: In some embodiments, in any situation where ischemic stroke is suspected but not definitely diagnosed, a device described herein is configured to be applied to a patient to stimulate target nerves with particular stimulation parameters. In some embodiments, this is done in the back of an ambulance that is not a mobile stroke unit, in the emergency department, and/or another clinical scenario where ischemic stroke is suspected. In some embodiments, the device is available for home use where patients at risk of stroke or caretakers of patients at risk place the device on the patient when stroke-like symptoms are suspected. In some embodiments, the monitoring component(s) of the device (as described herein) provide additional diagnostic information on physiological parameters, including but not limited to the oxygen utilization, cerebral blood flow, and/or neuronal signaling. In some embodiments, stimulation parameters (delivered to the patient via the device) enable treatment and management of neurological diagnoses other than ischemic stroke, such as hemorrhagic stroke, traumatic brain injury, epilepsy, transient ischemic attack, or migraine, among others. In some embodiments, diagnoses with suspected inflammatory responses are modulated through our device as well.

Treating Ischemic Stroke

In this example, a subject suffering from an ischemic stroke and reperfusion injury is treated using the devices and methods described herein. A subject presents to the emergency department showing one or more symptoms of an ischemic stroke and is diagnosed with an ischemic stroke.

Following the initial presentation and diagnose of ischemic stroke, a portion of the subject's brain tissue is at risk of ischemic injury resulting from lack of oxygen delivered to the tissue from the flow of oxygenated blood. There is at least a portion of the subject brain tissue which is permanently damaged due to prolonged lack of oxygen—the infract core. Surrounding the infract core there is a portion of tissue also at risk of permanent ischemic injury—the penumbral tissue. In order to minimize the amount of penumbral tissue permanently damaged and converted to an infarct core (e.g., neuron death or loss of function resulting from lack of oxygen), it is desirable to increase the flow of blood to the brain and increase the oxygenation of the tissue until such time as a reperfusion therapy can be administered to the subject to restore normal blood flow to the at risk tissue.

Shortly following diagnosis, the subject is fitted with the device assembly described herein configured to apply transcutaneous electrical stimulation to the supraorbital branch of the trigeminal nerve, and the auricular branch of the vagal nerve, electrically stimulating each target nerve concurrently. The device comprises a plurality of transcutaneous electrodes in contact with the subject's skin, and applies transcutaneous electrical stimulation to the target nerves. Stimulating the first target nerve and the second target nerve comprises administering a pulse frequency from about 20 Hz to about 60 Hz; administering a current from about 6 mA to about 8 mA; administering a pulse width of about 350 us; and administering a non-alternating biphasic current. Stimulating the first target nerve and the second target nerve further comprises administering a recovery pulse comprising an equal charge, of about 40% leading pulse amplitude, or administering a recovery pulse comprising from about 20% to about 60% of leading pulse amplitude.

Shortly following diagnosis and in the pre-reperfusion therapy stage, stimulating the first target nerve and the second target nerve comprises administering about a 20% trigeminal nerve stimulation duty cycle and about a 10% vagus nerve duty cycle constantly or continuously until reperfusion. Stimulating the target nerves as described herein increases the flow of blood to the brain, increase the oxygenation level of penumbral tissue, and reduces the amount of penumbral tissue ultimately converted to an infarct core, improving patient outcomes.

Treating Ischemic Stroke and Reperfusion Injury

In this example, a subject suffering from an ischemic stroke and a reperfusion injury is treated using the devices and methods described herein. A subject presents to the emergency department showing one or more symptoms of an ischemic stroke and is diagnosed with an ischemic stroke, and is treated as described in the above example entitled "Treating Ischemic Stroke." Once a reperfusion therapy is administered, the penumbral tissue of subject is then at risk from a reperfusion injury resulting from the rapid reoxygenation of the ischemic tissue, which may include oxidative damage, induction of oxidative stress, and inflammation.

Following administration of treatment as described above, in the above example entitled "Treating Ischemic Stroke," blood flow and oxygen is restored to the penumbral tissue, which is now at risk of a reperfusion injury.

Following administration of a reperfusion therapy, stimulating the first target nerve and the second target nerve comprises administering about a 10% trigeminal nerve stimulation duty cycle about every 4 hours and about a 10% vagus duty cycle about every 4 hours after reperfusion, and ceasing trigeminal nerve stimulation duty cycle after 24 hours post reperfusion. Stimulating the target nerves as described herein decreases the flow of blood to the brain, reduces the rate at which the oxygenation level of penumbral tissue increases or is restored, and reduces the amount of penumbral tissue experiencing a reperfusion injury, or reduces or mitigates a symptom of the reperfusion injury by reducing a differential increase of the oxygenation of the penumbral tissue, improving patient outcomes. In some embodiments, an amount of the penumbral tissue experiences reduce inflammation, oxidative stress, oxidative damage, resulting from reperfusion.

Treating Reperfusion Injury

In this example, a subject suffering from a reperfusion injury is treated using the devices and methods described herein. A subject presents to the emergency department showing one or more symptoms of an ischemic stroke and is diagnosed with an ischemic stroke, and is administered a reperfusion therapy.

Following administration of a reperfusion therapy, stimulating the first target nerve and the second target nerve comprises administering about a 10% trigeminal nerve stimulation duty cycle about every 4 hours and about a 10% vagus duty cycle about every 4 hours after reperfusion, and ceasing trigeminal nerve stimulation duty cycle after 24 hours post reperfusion. Stimulating the target nerves as described herein decreases the flow of blood to the brain, reduces the rate at which the oxygenation level of penumbral tissue increases or is restored, and reduces the amount of penumbral tissue experiencing a reperfusion injury, or reduces or mitigates a symptom of the reperfusion injury by reducing a differential increase of the oxygenation of the penumbral tissue, improving patient outcomes. In some embodiments, an amount of the penumbral tissue experiences reduce inflammation, oxidative stress, oxidative damage, resulting from reperfusion.

Treating Ischemic Stroke or Reperfusion Injury with a Randomized Electrical Stimulation Pattern In this example, a subject suffering from an ischemic stroke and/or a reperfusion injury is treated using the devices and methods described herein. In attempting to increase or decrease blood flow using the devices and methods described herein, repeating the same electrical stimulation parameters may result in habituation, or a reduced effect of the electrical stimulation upon flow of blood to the brain.

A subject presents to the emergency department showing one or more symptoms of an ischemic stroke and is diagnosed with an ischemic stroke, and is treated as described in the above example entitled "Treating Ischemic Stroke," "Treating Ischemic Stroke Reperfusion Injury," or "Treating Reperfusion Injury." However, in place of the electrical stimulation parameters described above, a randomized electrical stimulation pattern is applied.

Figure 11A:
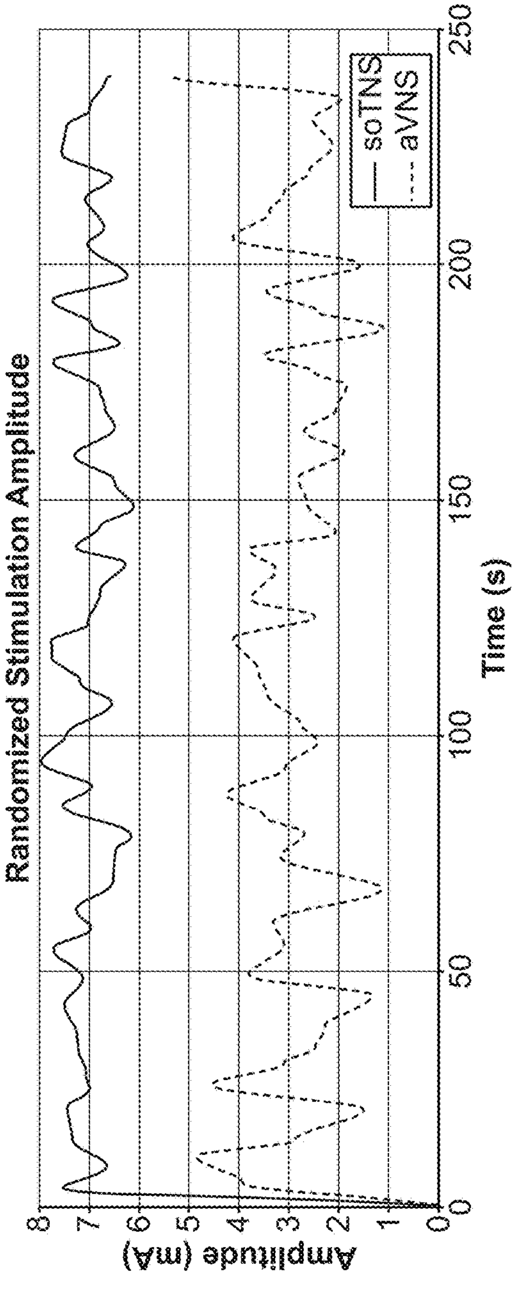
FIG. 11A provides an exemplary depiction of a randomized stimulation amplitude pattern of two target nerves according to an embodiment described herein.
Figure 11B:
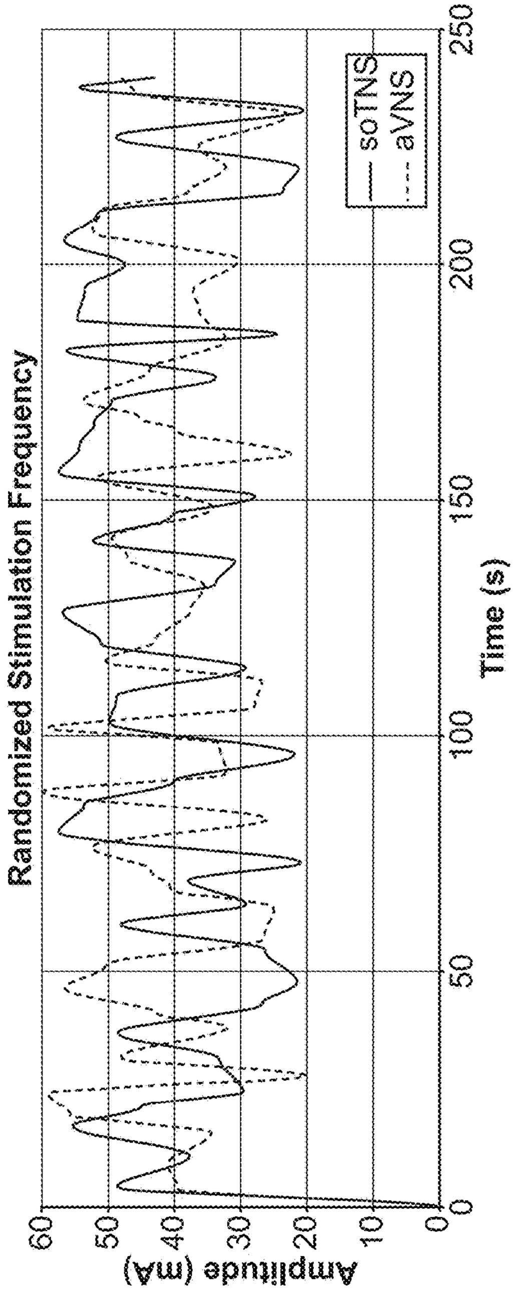
FIG. 11B provides an exemplary depiction of a randomized stimulation frequency pattern of two target nerves according to an embodiment described herein.

The randomized pattern is shown in FIGS. 11A and 11B, and show randomized stimulation amplitude (FIG. 11A) and randomized stimulation frequency (FIG. 11B). Stimulating the first target nerve and the second target nerve comprises administering a pulse frequency from about 20 Hz to about 60 Hz; administering a current from about 6 mA to about 8 mA; administering a pulse width of about 350 us; and administering a non-alternating biphasic current. Stimulating the first target nerve and the second target nerve further comprises administering a recovery pulse comprising an equal charge, of about 40% leading pulse amplitude, or administering a recovery pulse comprising from about 20% to about 60% of leading pulse amplitude.

The randomized pattern includes varying a current amplitude and a pulse frequency over a period of time, and varying a current amplitude and a pulse frequency over a period of time between an upper limit and a lower limit defined for the current amplitude and the pulse frequency. A first upper limit and a first lower limit, and a second upper limit and a second lower limit are defined for the current amplitude and the pulse frequency at the first target nerve and the second target nerve. The randomized pattern includes selecting a target amplitude and a target pulse frequency between the upper limit and the lower limit. The randomized pattern includes increasing or decreasing the current amplitude or the pulse frequency upwards or downwards to the target amplitude or the target pulse frequency. The randomized pattern includes randomly selecting a slope or a differential value within a predefined range to increase or decrease the current amplitude or the pulse frequency upwards or downwards to the target amplitude or the target pulse frequency. The randomized pattern further includes selecting a second target amplitude or a second target pulse frequency after the target amplitude or the target pulse frequency is reached. The randomized pattern further includes randomly selecting a slope or a differential value within a predefined range to increase or decrease the current amplitude or the pulse frequency upwards or downwards to the second target amplitude or the second target pulse frequency. The randomized pattern includes changing the current amplitude and the pulse frequency simultaneously or concurrently.

Shortly following diagnosis and in the pre-reperfusion therapy stage, stimulating the first target nerve and the second target nerve comprises administering about a 20% trigeminal nerve stimulation duty cycle and about a 10% vagus nerve duty cycle constantly or continuously until reperfusion using the randomized pattern described herein. Stimulating the target nerves as described herein increases the flow of blood to the brain, increase the oxygenation level of penumbral tissue, and reduces the amount of penumbral tissue ultimately converted to an infarct core, improving patient outcomes. Following administration of a reperfusion therapy, stimulating the first target nerve and the second target nerve comprises administering about a 10% trigeminal nerve stimulation duty cycle about every 4 hours and about a 10% vagus duty cycle about every 4 hours after reperfusion, and ceasing trigeminal nerve stimulation duty cycle after 24 hours post reperfusion, using the randomized pattern described herein. Stimulating the target nerves as described herein decreases the flow of blood to the brain, reduces the rate at which the oxygenation level of penumbral tissue increases or is restored, and reduces the amount of penumbral tissue experiencing a reperfusion injury, or reduces or mitigates a symptom of the reperfusion injury by reducing a differential increase of the oxygenation of the penumbral tissue, improving patient outcomes. In some embodiments, an amount of the penumbral tissue experiences reduce inflammation, oxidative stress, oxidative damage, resulting from reperfusion.

Stimulating the target nerves as described herein to treat ischemic stroke with a randomized electrical stimulation pattern increases the flow of blood to the brain, increase the oxygenation level of penumbral tissue, and reduces the amount of penumbral tissue ultimately converted to an infarct core, improving patient outcomes. When compared to stimulation of the target nerves with a non-randomized pattern, the randomized electrical stimulation pattern increases the flow of blood to the brain when administered using the pre-reperfusion therapy stage wave forms. In some cases, the increases the flow of blood to the brain when administered using the randomized electrical stimulation pattern comprises about 25% to about 50% increase over a non-randomized electrical stimulation pattern.

Stimulating the target nerves as described herein to treat reperfusion injury decreases the flow of blood to the brain, reduces the rate at which the oxygenation level of penumbral tissue increases or is restored, and reduces the amount of penumbral tissue experiencing a reperfusion injury, or reduces or mitigates a symptom of the reperfusion injury by reducing a differential increase of the oxygenation of the penumbral tissue, improving patient outcomes. In some embodiments, an amount of the penumbral tissue experiences reduce inflammation, oxidative stress, oxidative damage, resulting from reperfusion. When compared to stimulation of the target nerves with a non-randomized pattern, the randomized pattern randomized electrical stimulation pattern decrease the flow of blood to the brain and/or the rate of reoxygenation of the penumbral tissue when administered using the post-reperfusion therapy stage wave forms.

Treating Ischemic Stroke with Increased Trigeminal Nerve Stimulation

In this example, a subject suffering from an ischemic stroke and a reperfusion injury is treated using the devices and methods described herein. A subject presents to the emergency department showing one or more symptoms of an ischemic stroke and is diagnosed with an ischemic stroke, and is treated as described in the above example entitled "Treating Ischemic Stroke." However, differing trigeminal and vagus nerve duty stimulation parameters are applied.

Shortly following diagnosis and in the pre-reperfusion therapy stage, stimulating the first target nerve and the second target nerve comprises administering about a 100% trigeminal nerve stimulation duty cycle and about a 10% vagus nerve duty cycle constantly or continuously for the first hour of therapy, or until reperfusion. Thereafter, stimulating the first target nerve and the second target nerve comprises administering about a 5-20% trigeminal nerve stimulation duty cycle and about a 10% vagus nerve duty cycle constantly or continuously, or every 4 hours. Vagus duty cycle comprises maintaining the 10% duty cycle continuously, and then transitioning to 10% every 2-4 hours following reperfusion, or stopping after reperfusion. Stimulating the target nerves as described herein increases the flow of blood to the brain, increase the oxygenation level of penumbral tissue, and reduces the amount of penumbral tissue ultimately converted to an infarct core, improving patient outcomes.

Treating Ischemic Stroke with Increased Trigeminal and Vagus Nerve Stimulation

In this example, a subject suffering from an ischemic stroke and a reperfusion injury is treated using the devices and methods described herein. A subject presents to the emergency department showing one or more symptoms of an ischemic stroke and is diagnosed with an ischemic stroke, and is treated as described in the above example entitled "Treating Ischemic Stroke." However, differing trigeminal and vagus nerve duty stimulation parameters are applied.

Shortly following diagnosis and in the pre-reperfusion therapy stage, stimulating the first target nerve and the second target nerve comprises administering about a 100% trigeminal nerve stimulation duty cycle and about a 100% vagus nerve duty cycle constantly or continuously for treatment blocks between 1 minute to 4 hours, or until after reperfusion. Thereafter, stimulating the first target nerve and the second target nerve comprises administering about a 5-20% trigeminal nerve stimulation duty cycle and about a 10% vagus nerve duty cycle constantly or continuously, or every 4 hours; or another duty cycle detailed herein. Stimulating the target nerves as described herein increases the flow of blood to the brain, increase the oxygenation level of penumbral tissue, and reduces the amount of penumbral tissue ultimately converted to an infarct core, improving patient outcomes.

Treating Ischemic Stroke with Moderated Trigeminal and Vagus Nerve Stimulation

In this example, a subject suffering from an ischemic stroke and a reperfusion injury is treated using the devices and methods described herein. A subject presents to the emergency department showing one or more symptoms of an ischemic stroke and is diagnosed with an ischemic stroke, and is treated as described in the above example entitled "Treating Ischemic Stroke." However, differing trigeminal and vagus nerve duty stimulation parameters are applied.

Shortly following diagnosis and in the pre-reperfusion therapy stage, stimulating the first target nerve and the second target nerve comprises administering about a 20% trigeminal nerve stimulation duty cycle and about a 10% vagus nerve duty cycle constantly or continuously for treatment blocks between 1 to 24 hours, until after reperfusion, or until the patient is discharged from the hospital. Vagus nerve duty cycle continues at 10% vagus nerve duty cycle continuously, or comprises an initial duty cycle of 10% vagus nerve duty cycle continuously until reperfusion, and then transitions to a 10% vagus nerve duty cycle on an interval between 1 to 24 hours. Stimulating the target nerves as described herein increases the flow of blood to the brain, increase the oxygenation level of penumbral tissue, and reduces the amount of penumbral tissue ultimately converted to an infarct core, improving patient outcomes.

Other Exemplary Clinical Scenarios

Outside of the stroke workflow described in the previous sections, in some embodiments, a device described herein may also have utility in other clinical scenarios. In some embodiments, two additional use cases within the neurological fields comprise cases of traumatic brain injury (TBI) and subarachnoid hemorrhage (SAH) associated vasospasm. In some embodiments, clinical indications such as those requiring inflammation modulation, increasing central or cerebral blood flow, managing pain, for monitoring and prevention of complications, and/or clearance of unwanted metabolites/proteins, among others, are appropriate use cases for systems and devices described herein to intervene.

Traumatic Brain Injury

Traumatic Brain Injury (TBI) is an active process that progresses over time. The injured tissue may manifest as hemorrhage followed by edema resulting in increased intracranial pressure (ICP). Elevated ICP is a perfusion concern and causes secondary brain ischemia, leading to a similar cascade of events as stroke. In some embodiments, stimulation of target nerves described herein has demonstrated neuroprotective effects in TBI animal models. Accordingly, in some embodiments, utilization of a system or device described herein improve outcomes by mitigating secondary ischemia among other complications. Additionally, in some embodiments, through the monitoring component of the device (as described herein), the device is configured to follow patient progression through changes in perfusion or other physiological parameters.

Subarachnoid Hemorrhage

Subarachnoid Hemorrhage (SAH), bleeding between the brain and the surrounding membranes, is commonly caused by either a ruptured aneurysm or leaking from an arteriovenous malformation. SAH commonly causes arterial spasm in the vessels nearest to the bleeding site. Spasm can lead to focal ischemia and can precipitate a secondary stroke. During treatment, patients are being observed closely in the ICU and may require multiple days of management before spasm resolves. In some embodiments, a device described herein is configured to increase cerebral blood flow and modulate vessels to limit the effects of vasospasm in this patient population.

Inflammation

Inflammatory modulation could be used to reduce an acute inflammatory response in an emergency setting, in a sub-acute period of care, or for chronic management. In some embodiments, this is through modulation of cytokine release by the innate immune system during time of inflammation. In some embodiments, examples of conditions that could be managed in this manner include rheumatoid arthritis, irritable bowel syndrome, sepsis, renal ischemia, trauma/hemorrhagic shock, and acute lung injury, among others. The inflammatory modulation could be used to mediate hyperinflammation brought on during a cytokine storm for pathogens such as COVID-19.

Hypotension

In some embodiments, for cases of decreased central pressure found in forms of shock, peripheral vasoconstriction and central vasodilation mediated by a device described herein provides a more immediate central conservation of perfusion. In some embodiments, this limits acute organ injury to key organs such as the heart, kidney, brain, and liver, among others. In an emergency situation where a patient requires central access or other access to deliver vasopressors, in some embodiments, the device described herein acts as a faster onset stop-gap to maintain perfusion.

Disorders of Consciousness

Disorders of consciousness are a term used to describe damage to the brain that has resulted in alterations in a patient's consciousness. In some embodiments, stimulation delivered using a system or device described herein to a patient helps reactivate ascending pathways, activate the thalamus, and modulate neurotransmitters, among other mechanisms.

Headache/Pain

In some embodiments, facial pain associated with particular cranial nerves, such as the trigeminal, or other headaches, such as cluster headaches, tension headaches, or migraine, could be treated using a device described herein through stimulation of target nerve(s) (as described herein) and by improving blood flow to the area.

Intraprocedural Complications

In many vascular, cardiac, cardiothoracic, transplant, or other surgical specialty procedures, there is concern for complications that may compromise blood flow and perfusion to the brain. This could be in the form of clots that are released distally, by drops in cerebral blood pressure, or as a side effect of medications given. In some embodiments, a device described herein supplements blood flow as needed to decrease the rate of long term sequelae.

Glymphatic Clearance

The glial-lymphatic or glymphatic pathway is a clearance pathway that assists in the clearance of extracellular waste, metabolites, proteins, and fluid. The glymphatic clearance pathway fits within the broader cerebrospinal fluid (CSF) clearance system and plays a relevant role in stroke but also for other diseases, such as Alzheimer's Disease (AD). Buildup of protein complexes such as tau play a key role in pathogenesis in AD. In some embodiments, removal of such protein complexes via modulation of the clearance pathway provide a new management tool for AD and other neurodegenerative techniques. In some embodiments, target nerve(s) stimulation using a device described herein modulates these important flow pathways.

Glymphatic clearance can also be utilized for control drug availability in the CNS. Drug dosing for the CNS is difficult due to concerns of toxicity and the challenges of bypassing the body's natural protection mechanisms, like the blood brain barrier. The glymphatic clearance pathway consisting of para-arterial cerebrospinal fluid influx and a para-venous interstitial fluid clearance along with aquaporin channels, acts as a waste clearance mechanism. This can be harnessed for more controlled drug dosing.

Blood-Brain Barrier Modulation

The blood brain barrier forms a key protective mechanism, critical in regulating homeostasis in the central nervous system (CNS). It mediates what molecules are able to affect the brain and essentially forms the first line of defense against toxins, microorganisms, and inflammatory cells, among others. As a barrier, it also presents a significant hurdle to the delivery of drugs and therapeutics to the brain. Studies have demonstrated the potential effectiveness of attenuating the breakdown of the blood brain barrier through neurostimulation. In some embodiments, a device described herein is configured to modulate the blood brain barrier to reduce harmful effects of barrier disruption that occurs during traumatic events. Additionally, in some embodiments, when the blood brain barrier is disrupted for therapeutic delivery, such as through focused ultrasound, the device (as described herein) is configured to promote subsequent recovery and to attenuate the disruption.

While this disclosure has been described with reference to illustrative embodiments, this description is not intended to be construed in a limiting sense. Various modifications and combinations of illustrative embodiments, as well as other embodiments of the invention, will be apparent to persons skilled in the art upon reference to the description. It is therefore intended that the appended claims encompass such modifications and enhancements.

Mild Cognitive Impairment

Mild Cognitive Impairment (MCI) is associated with early stages of dementia and has been characterized by deficits in regional hypoperfusion in areas of the brain. If MCI progresses to a form of dementia (e.g., Alzheimer's Disease), areas of hypoperfusion can become atrophied contributing to the dementia pathology. In some embodiments, stimulation of target nerves described herein provides protection for a patient with MCI, mitigating odds of disease progression and neurological degeneration. Additionally, in some embodiments, through the monitoring component of the device (as described herein), the device is configured to follow patient progression, enabling a clinician to change stimulation dosing or treatment paradigms.

What is claimed is:

1. A method of stimulating a plurality of target nerves in a subject to treat a medical condition, wherein the medical condition is one or more of ischemic stroke, cerebral brain damage due to ischemic stroke, hemorrhagic stroke, cerebral brain damage due to hemorrhagic stroke, a reperfusion injury, the method comprising:

transcutaneously delivering a first stimulation energy to a supraorbital branch of a trigeminal nerve;

transcutaneously delivering a second stimulation energy to an auricular branch of a vagal nerve;

wherein the first and second stimulation energies are delivered in combination to treat the medical condition so that the first and second stimulation energies are delivered at a first ratio of first to second stimulation energy for a first time period, wherein the first and second stimulation energies are delivered at a second ratio of first to second stimulation energy for a second time period, wherein the first and second ratios are different, and wherein the second time period is after the first time period; and measuring an oxygenation level of the subject.

2. The method of claim 1, wherein one or more of the first or second stimulation energies are delivered by one or more of a wearable or adherable stimulation device.

3. The method of claim 1, wherein one or more of the first or second stimulation energies are electrical.

4. The method of claim 1, wherein one or more of the first or second stimulation energies are one or more of electrical, mechanical, vibratory, acoustic, optical, or thermal.

5. The method of claim 1, wherein the first and second stimulation energies are delivered simultaneously.

6. The method of claim 1, wherein the first and second stimulation energies are delivered sequentially.

7. The method of claim 1, wherein one or more of the first or second stimulation energies are provided at a frequency between 0.2 and 500 Hz.

8. The method of claim 1, wherein one or more of the first or second stimulation energies are provided at an amplitude of between 0.1 and 200 mA.

9. The method of claim 1, wherein one or more of the first or second stimulation energies are provided at a pulse width between 1 μs and 2 s.

10. The method of claim 1, wherein one or more of the first or second stimulation energies provide a charge of between 0.5 mC to 200 mC.

11. The method of claim 1, wherein one or more of the first or second stimulation energies are biphasic.

12. The method of claim 1, wherein one or more of the first or second stimulation energies are delivered with one or more randomized stimulation parameters, the one or more stimulation parameters comprising one or more of pulse width; frequency; amplitude; pulse train duration; a delay between pulse trains; interphase duration; time between biphasic pulses; ratio of a recovery pulse to a depolarization pulse; an amount of time between altering a parameter; or a relative timing of stimulation pulse delivery between location, if using a fixed frequency.

13. The method of claim 1, wherein the first and second stimulation energies are delivered within 24 hours of an insult to the subject.

14. The method of claim 13, wherein the insult is a stroke.

15. The method of claim 1, further comprising determining whether reperfusion has occurred in the subject.

16. The method of claim 1, further comprising changing a rate of delivering one or more of the first or second stimulation energies in response to an occurrence of reperfusion in the subject.

17. The method of claim 1, wherein the first or second stimulation energies are delivered simultaneously at a first point, and sequentially at a second point.

18. The method of claim 1, wherein the first and second stimulations are delivered in an amount therapeutically effective to treat the medical condition.

19. The method of claim 1, further comprising adjusting one or more of the first stimulation energy or the second stimulation energy in response to the measured oxygenation level.

20. The method of claim 1, wherein the oxygenation level is measured with one or more near-infrared monitors.

21. The method of claim 1, wherein the first and second stimulation energies are delivered within 3 to 5 days of the insult to the subject.

22. The method of claim 21, wherein the insult is a stroke.

23. The method of claim 1, wherein the measured oxygenation level comprises a blood oxygenation level of the subject.

24. The method of claim 1, wherein the measured oxygenation level comprises a cerebral oxygenation level of the subject.

25. The method of claim 1, wherein measuring the oxygenation level of the subject comprises measuring one or more of a motion, a muscle contraction, a spasm, a verbal input, a visual input, a gesture, a facial expression, a cerebral oxygenation, a partial pressure of oxygen in brain tissue, a cerebral metabolic rate, a pulse rate, a blood pressure, a blood flow velocity, a pulsatility, a tissue perfusion reading, a neural activity, an electroencephalography (EEG) reading, or an electrode resistance from the subject.

* * * * *